(12) United States Patent
Winters et al.

(10) Patent No.: US 8,822,460 B2
(45) Date of Patent: Sep. 2, 2014

(54) FUSED CYCLOPENTYL ANTAGONISTS OF CCR2

(71) Applicant: Janssen Pharmaceutica, NV, Beerse (BE)

(72) Inventors: Michael P. Winters, Morgantown, PA (US); Nagy E. Fawzy, Piscataway, NJ (US); Fu-An Kang, Collegeville, PA (US); Zhihua Sui, Norristown, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 13/856,666

(22) Filed: Apr. 4, 2013

(65) Prior Publication Data

US 2014/0018356 A1 Jan. 16, 2014

Related U.S. Application Data

(60) Provisional application No. 61/621,138, filed on Apr. 6, 2012.

(51) Int. Cl.
*C07D 405/14* (2006.01)
*A61K 31/41* (2006.01)
(52) U.S. Cl.
USPC ............... 514/230.5; 514/252.2; 514/253.11; 514/256; 514/300; 514/307; 514/338; 544/90; 544/295; 544/332; 544/364; 546/123; 546/146; 546/276.7; 549/418; 549/465
(58) Field of Classification Search
None
See application file for complete search history.

(56) References Cited

FOREIGN PATENT DOCUMENTS

| WO | WO 0119360 | 3/2001 |
|---|---|---|
| WO | WO 03/093266 | 11/2003 |
| WO | WO 2005/079496 | 9/2005 |
| WO | WO 2005/120505 | 12/2005 |
| WO | WO 2006012396 | 2/2006 |
| WO | WO 2006/098959 | 9/2006 |
| WO | WO 2009033281 | 3/2009 |

OTHER PUBLICATIONS

International Search Report, PCT.US2013/050665, Dated, Oct. 21, 2013.
International Search Report, PCT/US2013/035396, Dated Aug. 8, 2013.
Dawson J, et al., Targeting monocyte chemoattractant protein-1 signaling in disease, *Expert Opin. Ther. Targets*, Feb. 2003 7 (1):35-48.
Rollins B J, Monocyte chemoattractant protein 1: a potential regulator of monocyte recruitment in inflammatory disease, *Mol. Med. Today*, 1996, 2:198.
Cho B T, et al., Catalytic Enantioselective Reactions. Part 15. Oxazaborolidine-Catalyzed Asymmetric Reduction of α-Keto Acetals with N,N-Diethylaniline-Borane (DEANB) Complex, *Bull. Korean Chem Soc.*, 1999, 20:397.
Corey E J, et al., Highly Enantioselective Borane Reduction of Ketones Catalyzed by Chiral Oxazaborilidines. Mechanism and Synthetic Implications, *J. Am. Chem. Soc.*, 1987, 109:5551-5553.
Tanaka, K.; et. al., "A New Approach for the Total Synthesis of L-γ-Carboxyglutamic Acid: Utility of Ruthenium Tetroxide Oxidation" Nitta, Y. *Chem. Pharm. Bull.* 1986, 34(9), 3879-84.
Nordmann, R.; et. al., "115. Synthesis and Conformation of (5R,8R,10R)-8-(Methylthiomethyl)ergoline-6-carboxamidine", *Helv. Chim. Acta*, 1985, 68(4), 1025-32.
Smith, M. E. B. et. al., "Highly selective directed hydrogenation of enantiopure 4-(tert-butoxycarbonylamino_cyclopent-1-enecarboxylic acid methyl esters" *Tetrahedron Lett.* 2001, 42(7), 1347-50.
Garbrecht, W. L. et. al., "The Synthesis of Certain 5-Aminotetrazole Derivatives", *J. Org. Chem.*, 1953, 18, 1003-1013.
Regainia, Z. et al., "Synthesis of 1,2,5-Thiadiazolidines 1,1-dioxides (Cyclosulfamides) Starting from Amino acids and Chlorosulfonyl Isocyanate", *Tetrahedron* 2000, 56(3), 381-7.
Sarges, R.; et al., "Sulfamylurea Hypoglycemic Agents. 6. High-Potency Derivatives", *J. Med. Chem.* 1976, 19(5), 695-709.
Abdaoui, M. et al., "Synthese et Structure de 2-chloroethylnitrososulfamides (CENS) derives D'Aminoacides. Partie 5", *Tetrahedron* 2000, 56(16), 2427-35.
Gillaspy, M. et al., "A Simple Method for the Formation of Cyclopropylamines: The First Synthesis of Tricyclopropylamine", *Tetrahedron Lett.* 1995, 36(41), 7399-402.
Lyons, T. W. et. al., "Palladium-Catalyzed Ligand-Directed C-H Functionalization Reactions", *Chem. Rev.* 2010, 110(2), 1147-69.
Levins, C. et. al., "Efficient Phosphonium-Mediated Synthesis of 2-Amino-1,3,4-oxadiazoles", *Org. Lett.* 2008, 10(9), 1755-1758.
Hiltmann, R. et al., "Stereochemische Untersuchungen uber Arzneimittel. 4. Mitt. (*)", *Eur. J. Med. Chem.* 1977, 12(1), 63-8.
Hackler, R. E. et. al., "Synthetic Communications: An International Journal for Rapid Communication of Synthetic Organic Chemistry", *Syn. Comm.* 1975, 5(2), 143-6.
King, J. A. et. al., "The Preparation of Some a-Benzylamino-B,B-dialkoxypropionic Acid Derivatives", *J. Amer. Chem. Soc.* 1950, 72, 1236-40.
Rembarz, G. et al., "Reaktionen mit Natriumdicyanimid", *J. fuer Prak. Chem*, 1964, 26(5-6), 314-8.

*Primary Examiner* — Zinna Northington Davis
(74) *Attorney, Agent, or Firm* — Mary A. Appollina

(57) ABSTRACT

The present invention comprises compounds of Formula (I).

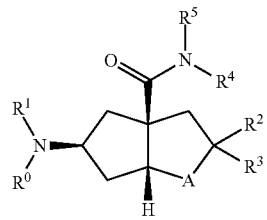

Formula (I)

wherein: $R^0$, $R^1$, $R^2$, $R^3$, $R^4$, $R^5$, and A are as defined in the specification. The invention also comprises a method of preventing, treating or ameliorating a syndrome, disorder or disease, wherein said syndrome, disorder or disease is type II diabetes, obesity and asthma. The invention also comprises a method of inhibiting CCR2 activity in a mammal by administration of a therapeutically effective amount of at least one compound of Formula (I).

18 Claims, 5 Drawing Sheets

FUSED CYCLOPENTYL ANTAGONISTS OF CCR2

CROSS REFERENCE TO RELATED APPLICATION

This application claims priority from U.S. Provisional Application Ser. No. 61/621,138 filed Apr. 6, 2012, the contents of which are hereby incorporated by reference in their entirety.

FIELD OF THE INVENTION

The invention is directed to substituted fused cyclopentyl compounds, which are antagonists to the chemoattractant cytokine receptor 2 (CCR2), pharmaceutical compositions, and methods for use thereof. More particularly, the CCR2 antagonists are compounds useful for preventing, treating or ameliorating a CCR2 mediated syndrome, disorder or disease. The present invention is further directed to a crystalline succinate salt of ((3aS,5S,6aR)-5-(((3S,4S)-3-methoxytetrahydro-2H-pyran-4-yl)amino)hexahydro-2H-cyclopenta[b]furan-3a-yl)(3-(trifluoromethyl)-7,8-dihydro-1,6-naphthyridin-6(5H)-yl)methanone, pharmaceutical compositions containing said salt and the use of said salt in the treatment of disorders, such as type II diabetes, obesity and asthma. The present invention is further directed to a novel process for the preparation of said crystalline succinate salt.

BACKGROUND OF THE INVENTION

CCR2 is a member of the GPCR family of receptors, as are all known chemokine receptors, and are expressed by monocytes and memory T-lymphocytes. The CCR2 signaling cascade involves activation of phospholipases (PLCβ2), protein kinases (PKC), and lipid kinases (PI-3 kinase).

Chemoattractant cytokines (i.e., chemokines) are relatively small proteins (8-10 kD), which stimulate the migration of cells. The chemokine family is divided into four sub-families based on the number of amino acid residues between the first and second highly conserved cysteines.

Monocyte chemotactic protein-1 (MCP-1) is a member of the CC chemokine subfamily (wherein CC represents the subfamily having adjacent first and second cysteines) and binds to the cell-surface chemokine receptor 2 (CCR2). MCP-1 is a potent chemotactic factor, which, after binding to CCR2, mediates monocyte and lymphocyte migration (i.e., chemotaxis) toward a site of inflammation. MCP-1 is also expressed by cardiac muscle cells, blood vessel endothelial cells, fibroblasts, chondrocytes, smooth muscle cells, mesangial cells, alveolar cells, T-lymphocytes, marcophages, and the like.

After monocytes enter the inflammatory tissue and differentiate into macrophages, monocyte differentiation provides a secondary source of several proinflammatory modulators, including tumor necrosis factor-α (TNF-α), interleukin-1 (IL-1), IL-8 (a member of the CXC chemokine subfamily, wherein CXC represents one amino acid residue between the first and second cysteines), IL-12, arachidonic acid metabolites (e.g., PGE$_2$ and LTB$_4$), oxygen-derived free radicals, matrix metalloproteinases, and complement components.

Animal model studies of chronic inflammatory diseases have demonstrated that inhibition of binding between MCP-1 and CCR2 by an antagonist suppresses the inflammatory response. The interaction between MCP-1 and CCR2 has been implicated (see Rollins B J, Monocyte chemoattractant protein 1: a potential regulator of monocyte recruitment in inflammatory disease, *Mol. Med. Today,* 1996, 2:198; and Dawson J, et al., Targeting monocyte chemoattractant protein-1 signaling in disease, *Expert Opin. Ther. Targets,* 2003 Feb. 7 (1):35-48) in inflammatory disease pathologies such as psoriasis, uveitis, atherosclerosis, rheumatoid arthritis (RA), multiple sclerosis, Crohn's Disease, nephritis, organ allograft rejection, fibroid lung, renal insufficiency, type II diabetes and diabetic complications, diabetic nephropathy, diabetic retinopathy, diabetic retinitis, diabetic microangiopathy, tuberculosis, sarcoidosis, invasive staphylococcia, inflammation after cataract surgery, allergic rhinitis, allergic conjunctivitis, chronic urticaria, Chronic Obstructive Pulmonary Disease (COPD), allergic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, and stomach.

Monocyte migration is inhibited by MCP-1 antagonists (either antibodies or soluble, inactive fragments of MCP-1), which have been shown to inhibit the development of arthritis, asthma, and uveitis. Both MCP-1 and CCR2 knockout (KO) mice have demonstrated that monocyte infiltration into inflammatory lesions is significantly decreased. In addition, such KO mice are resistant to the development of experimental allergic encephalomyelitis (EAE, a model of human MS), cockroach allergen-induced asthma, atherosclerosis, and uveitis. Rheumatoid arthritis and Crohn's Disease patients have improved during treatment with TNF-α antagonists (e.g., monoclonal antibodies and soluble receptors) at dose levels correlated with decreases in MCP-1 expression and the number of infiltrating macrophages.

MCP-1 has been implicated in the pathogenesis of seasonal and chronic allergic rhinitis, having been found in the nasal mucosa of most patients with dust mite allergies. MCP-1 has also been found to induce histamine release from basophils in vitro. During allergic conditions, both allergens and histamines have been shown to trigger (i.e. to up-regulate) the expression of MCP-1 and other chemokines in the nasal mucosa of people with allergic rhinitis, suggesting the presence of a positive feedback loop in such patients.

There remains a need for small molecule CCR2 antagonists for preventing, treating or ameliorating a CCR2 mediated inflammatory syndrome, disorder or disease resulting from MCP-1 induced monocyte and lymphocyte migration to a site of inflammation.

All documents cited herein are incorporated by reference.

SUMMARY OF THE INVENTION

The present invention relates to compounds of Formula (I)

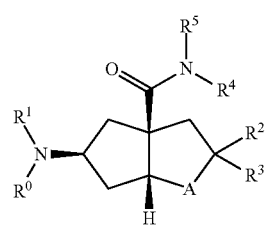

Formula (I)

wherein:

A is O, or S;

$R^0$ is H, or $C_{(1-4)}$alkyl;

wherein said $C_{(1-4)}$alkyl is optionally substituted with OH, $C_{(1-4)}$alkyl-$(OCH_2CH_2)_n$—$OCH_3$, $OCH_3$, $CO_2H$, $C(O)NH_2$, $SO_2NH_2$, or $CO_2C_{(1-4)}$alkyl;

n is 1, 2, or 3;

$R^1$ is cyclohexyl, or tetrahydropyranyl;

wherein said cyclohexyl or tetrahydropyranyl may be optionally substituted with one substituent selected from the group consisting of $OCH_3$, OH, $CH_2CH_3$, —CN, $NH_2$, $NH(CH_3)$, $N(CH_3)_2$, and $OCF_3$;

alternatively, $R^0$ and $R^1$ are taken together with their attached nitrogen to form a ring selected from the group consisting of

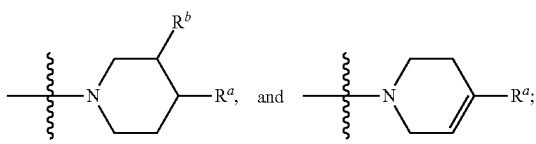

$R^a$ is phenyl; wherein the phenyl is optionally substituted with $C(O)NH_2$, $C(O)NHC_{(1-4)}$alkyl, $SO_2NH_2$, $C(O)N(C_{(1-4)}$alkyl$)_2$, $OCH_3$, $CO_2CH_3$, or $CO_2H$;

$R^b$ is $C_{(1-4)}$alkyl, or $OC_{(1-4)}$alkyl;

$R^2$ is selected from the group consisting of H, $C_{(1-4)}$alkyl, cyclopropyl, cyclohexyl, phenyl, pyridyl, pyrimidyl, pyrazyl, pyrazolyl, imidazolyl, isoxazolyl, thiazolyl, furyl, and thiophenyl;

wherein said phenyl, pyridyl, pyrimidyl, pyrazyl, pyrazolyl, imidazolyl, oxazolyl, isoxazolyl, thiazolyl, furyl, or thiophenyl is optionally substituted with one substituent selected from the group consisting of $NH_2$, $NHC_{(1-3)}$alkyl, $N(C_{(1-3)}$alkyl$)_2$, $C_{(1-3)}$alkyl, —CN, —CH=$CH_2$, —$CONH_2$, —$CO_2H$, —$NO_2$, —$CONHC_{(1-4)}$alkyl, $CON(C_{(1-4)}$alkyl$)_2$, $C_{(1-4)}$alkyl$CONH_2$, —$NHCOC_{(1-4)}$alkyl, —$CO_2C_{(1-4)}$alkyl, $CF_3$, $SO_2C_{(1-4)}$alkyl, —$SO_2NH_2$, —$SO_2NH(C_{(1-4)}$alkyl), and —$SO_2N(C_{(1-4)}$alkyl$)_2$;

$R^3$ is H, or $CH_3$;

alternatively, $R^3$ and $R^2$ are taken together with their attached carbon to form

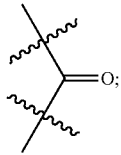 [SMILES: *C(*)=O]

$R^4$ is

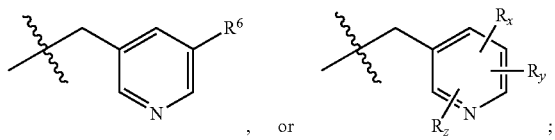

$R^5$ is H, or $CH_3$;

alternatively, $R^4$ and $R^5$ are taken together with their attached nitrogen to form a ring selected from the group consisting of

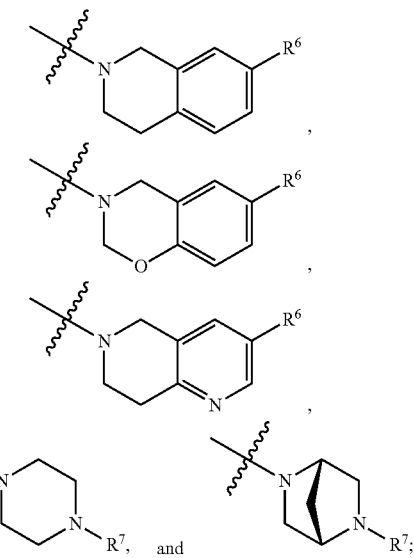

$R^6$ is $CF_3$, or $OCF_3$;

$R^7$ is a $CF_3$ substituted heteroaryl, provided that $R^7$ is not

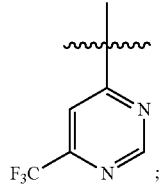

$R_x$ is $CF_3$, F, Cl, CN, or $OCH_3$;

$R_y$ is H, F, Cl, or $CF_3$;

$R_z$ is H, or F;

and pharmaceutically acceptable salts thereof.

The present invention is further directed to a succinate salt of a compound of formula (I-S)

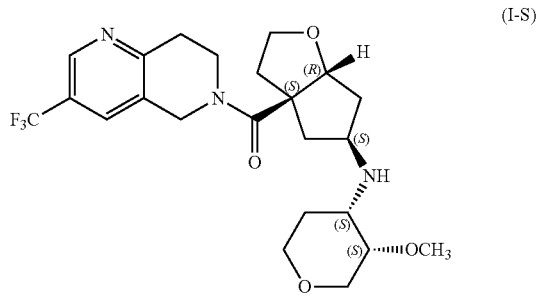

(I-S)

also known as ((3aS,5S,6aR)-5-(((3S,4S)-3-methoxytetrahydro-2H-pyran-4-yl)amino)hexahydro-2H-cyclopenta[b]furan-3a-yl)(3-(trifluoromethyl)-7,8-dihydro-1,6-naphthyridin-6(5H)-yl)methanone. In an embodiment of the present invention, the succinate salt of the compound of formula (I-S) is crystalline. In another embodiment, the present invention is directed to a succinate salt of the compound of formula (I-S), wherein the salt is crystalline hydrate form; preferably, the hydrate contains about 0.6 moles water per mole of the compound of formula (I-S). In yet another embodiment of the present invention, the succinate salt of the compound of formula (I-S) is crystalline hydrate form containing about 0.6 moles water per mole of the compound of formula (I-S) and is further hygroscopic.

The present invention is further directed to a process for the preparation of a succinate salt of the compound of formula (I-S), preferably a crystalline succinate salt of the compound of formula (I-S), as described in more detail hereinafter.

DETAILED DESCRIPTION OF THE INVENTION

Figure 1:
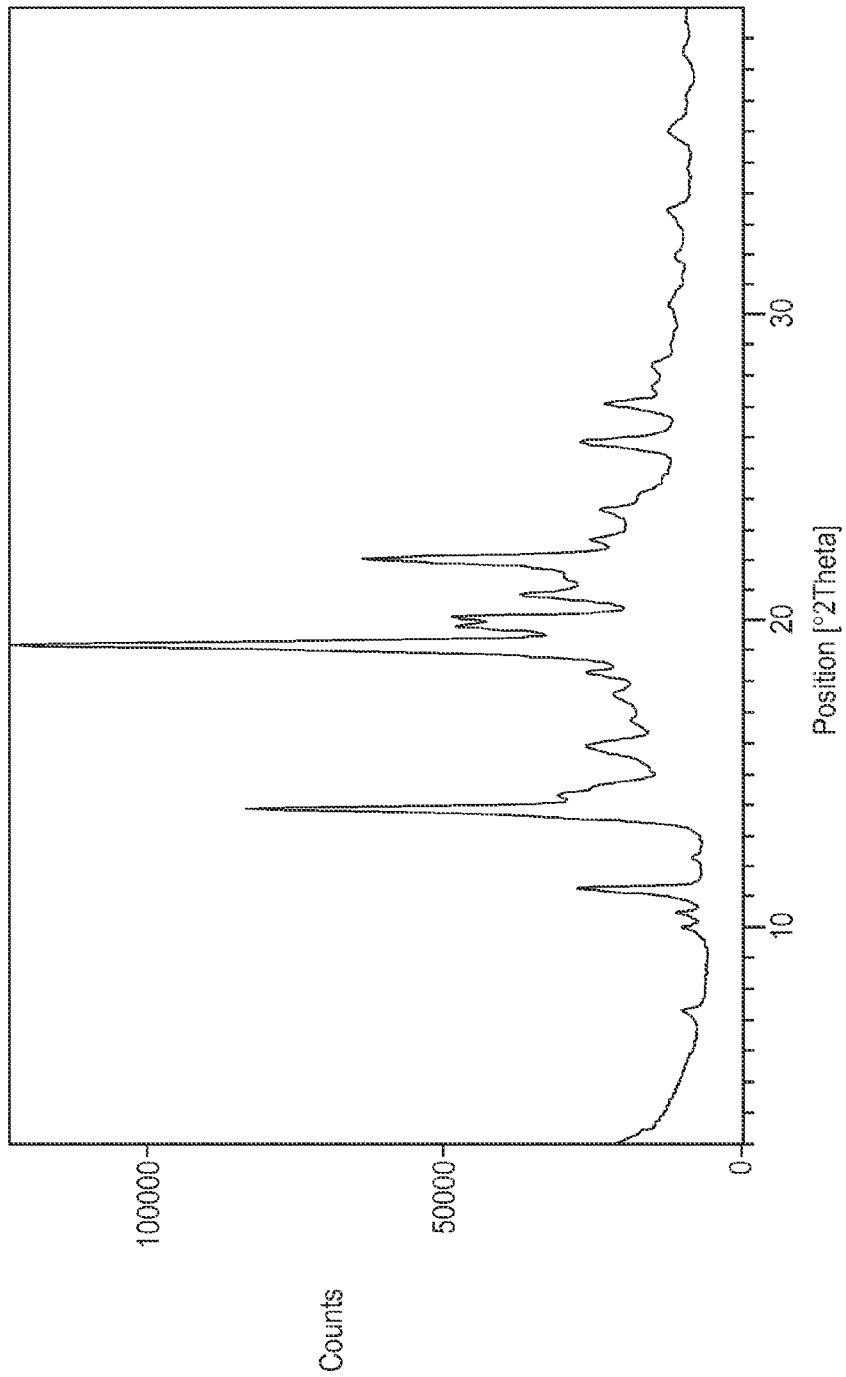
FIG. 1 illustrates a representative pXRD spectrum for the crystalline succinate salt of the compound of formula (I-S).

The present invention relates to the compounds of Formula (I)

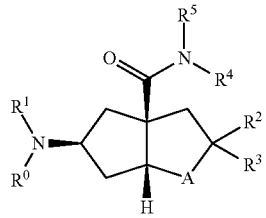

Formula (I)

wherein:

A, $R^0$, $R^1$, $R^2$, $R^3$, $R^4$ and $R^5$ are as defined above.

In an embodiment, the invention is directed to compounds of formula (I) wherein A is O.

In another embodiment, the invention is directed to compounds of formula (I) wherein A is O, or S;

$R^0$ is H, or $C_{(1-4)}$alkyl;

wherein said $C_{(1-4)}$alkyl is optionally substituted with OH, $C_{(1-4)}$alkyl-$(OCH_2CH_2)_n$—$OCH_3$, or $OCH_3$;

n is 1, 2, or 3;

$R^1$ is cyclohexyl, 1-methoxy cyclohex-2-yl, tetrahydropyran-4-yl, or 3-methoxy tetrahydropyran-4-yl;

alternatively, $R^0$ and $R^1$ are taken together with their attached nitrogen to form a ring selected from the group consisting of

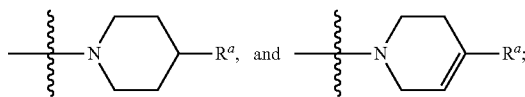

$R^a$ is phenyl;

wherein the phenyl is optionally substituted with $C(O)NH_2$, $C(O)NHCH_3$, $SO_2NH_2$, $C(O)N(CH_3)_2$, $OCH_3$, $CO_2CH_3$, or $CO_2H$;

$R^2$ is selected from the group consisting of H, $C_{(1-4)}$alkyl, cyclopropyl, cyclohexyl, phenyl, pyridyl, pyrimidyl, pyrazyl, pyrazolyl, imidazolyl, isoxazolyl, thiazolyl, furyl, and thiophenyl;

wherein said phenyl, pyridyl, pyrimidyl, pyrazyl, pyrazolyl, imidazolyl, oxazolyl, isoxazolyl, thiazolyl, furyl, or thiophenyl is optionally substituted with one substituent selected from the group consisting of $NH_2$, $NHC_{(1-3)}$alkyl, $N(C_{(1-3)}$alkyl$)_2$, $C_{(1-3)}$alkyl, —CN, —CH=$CH_2$, —$CONH_2$, —$CO_2H$, —$NO_2$, —$CONHC_{(1-4)}$alkyl, $CON(C_{(1-4)}$alkyl$)_2$, $C_{(1-4)}$alkyl$CONH_2$, —$NHCOC_{(1-4)}$alkyl, —$CO_2C_{(1-4)}$alkyl, $CF_3$, $SO_2C_{(1-4)}$alkyl, —$SO_2NH_2$, —$SO_2NH(C_{(1-4)}$alkyl), and —$SO_2N(C_{(1-4)}$alkyl$)_2$;

$R^3$ is H, or $CH_3$;

alternatively, $R^3$ and $R^2$ are taken together with their attached carbon to form

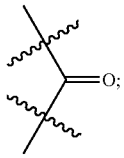 [SMILES: *C(*)=O]

$R^4$ and $R^5$ are taken together with their attached nitrogen to form a ring selected from the group consisting of

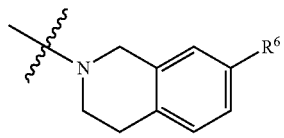

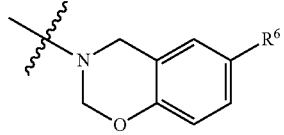

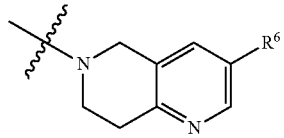

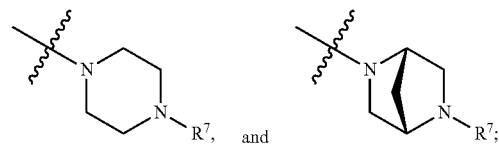

$R^6$ is $CF_3$, or $OCF_3$;

$R^7$ is

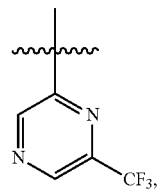 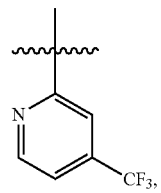

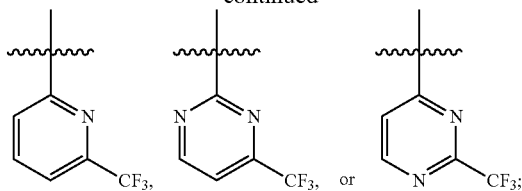

and pharmaceutically acceptable salts thereof.

In another embodiment of the invention

A is O, or S;

$R^0$ is H, $CH_3$, $CH_2CH_2CH_2OH$, $CH_2CH_2OH$, $CH_2CH_2CH_2(OCH_2CH_2)_3OCH_3$, or $CH_2CH_2OCH_3$;

$R^1$ is tetrahydropyran-4-yl, or 3-methoxy tetrahydropyran-4-yl;

alternatively, $R^0$ and $R^1$ are taken together with their attached nitrogen to form a ring selected from the group consisting of

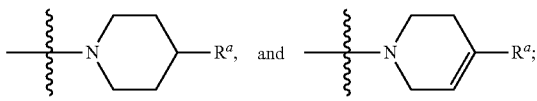

$R^a$ is phenyl;

wherein the phenyl is optionally substituted with $C(O)N(CH_3)_2$, $OCH_3$, or $CO_2H$;

$R^2$ is H, $C_{(1-4)}$alkyl, cyclopropyl, cyclohexyl, thiazol-2-yl, 1-methyl-imidazol-2-yl, 1-methyl-pyrazol-5-yl, or phenyl;

$R^3$ is H, or $CH_3$;

alternatively, $R^3$ and $R^2$ are taken together with their attached carbon to form

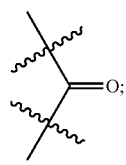

$R^4$ and $R^5$ are taken together with their attached nitrogen to form a ring selected from the group consisting of

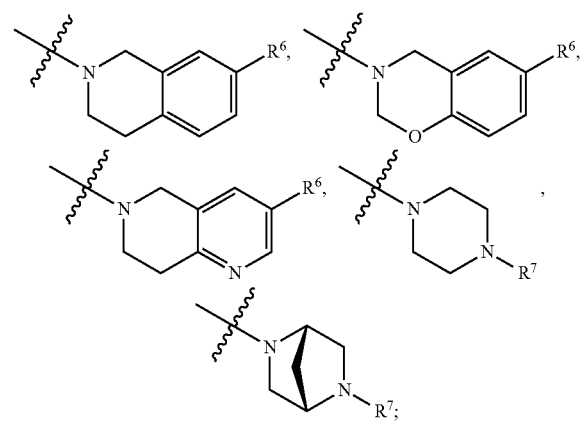

$R^6$ is $CF_3$, or $OCF_3$;

$R^7$ is

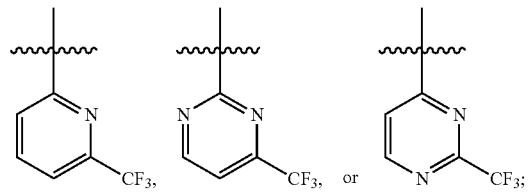

and pharmaceutically acceptable salts thereof.

In another embodiment, the present invention is directed to compounds of formula (I) wherein A is O;

$R^0$ is H, $CH_3$, $CH_2CH_2CH_2OH$, $CH_2CH_2OH$, $CH_2CH_2CH_2(OCH_2CH_2)_3OCH_3$, or $CH_2CH_2OCH_3$;

$R^1$ is tetrahydropyran-4-yl, or 3-methoxy tetrahydropyran-4-yl;

alternatively, $R^0$ and $R^1$ may be taken together with their attached nitrogen to form a ring selected from the group consisting of

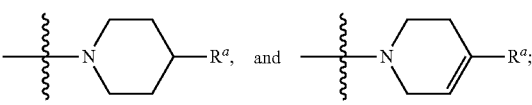

$R^a$ is phenyl;

wherein the phenyl is optionally substituted with $C(O)N(CH_3)_2$, $OCH_3$, or $CO_2H$;

$R^2$ is H, $C_{(1-4)}$alkyl, cyclopropyl, cyclohexyl, thiazol-2-yl, 1-methyl-imidazol-2-yl, 1-methyl-pyrazol-5-yl, or phenyl;

$R^3$ is H, or $CH_3$;

alternatively, $R^3$ and $R^2$ are taken together with their attached carbon to form

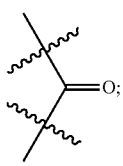 [SMILES: *C(*)=O]

$R^4$ and $R^5$ are taken together with their attached nitrogen to form a ring selected from the group consisting of

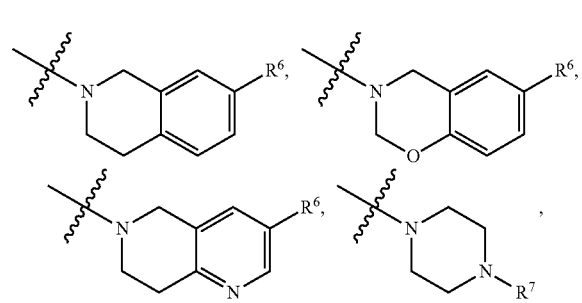

-continued
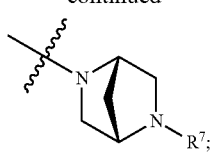
R⁶ is CF₃, or OCF₃;
R⁷ is
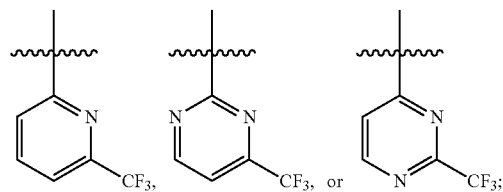
and pharmaceutically acceptable salts thereof.
In another embodiment, the present invention is directed to any one or more compounds, independently selected from the group consisting of:
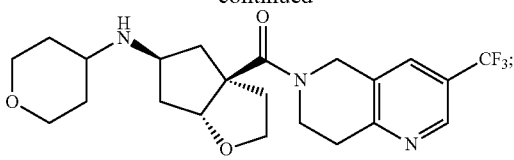
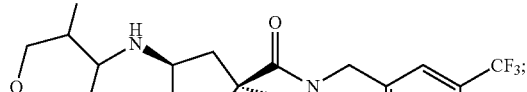
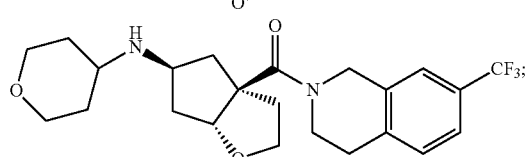
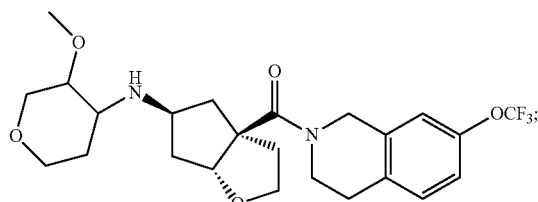
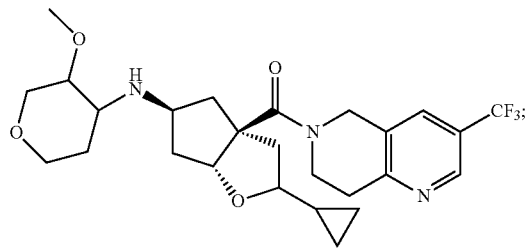
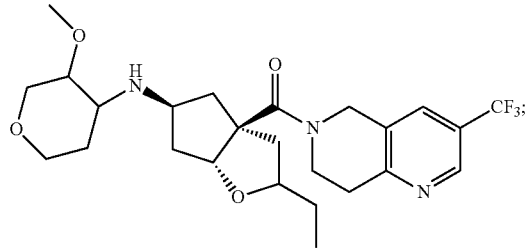
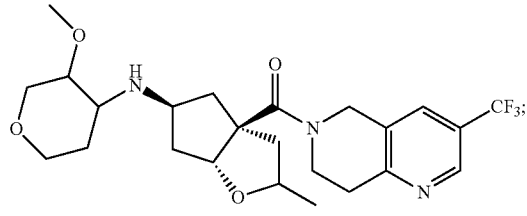
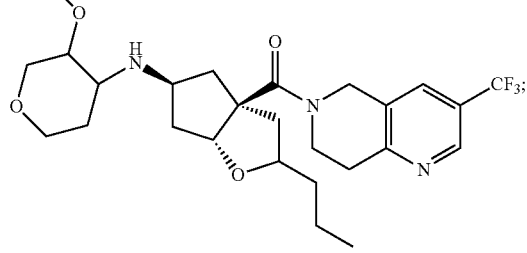

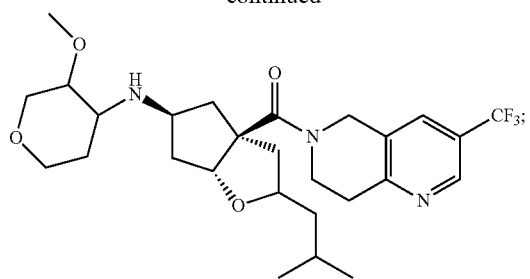
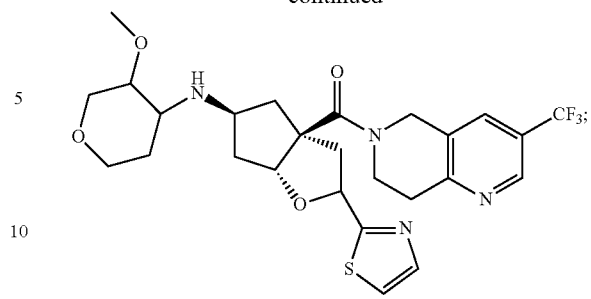
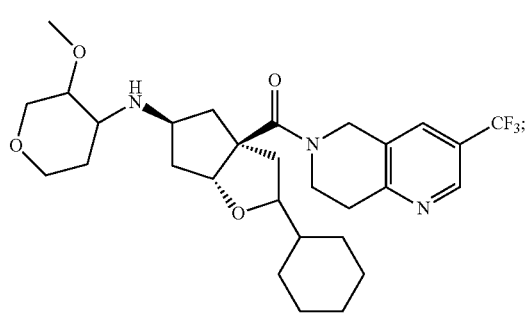
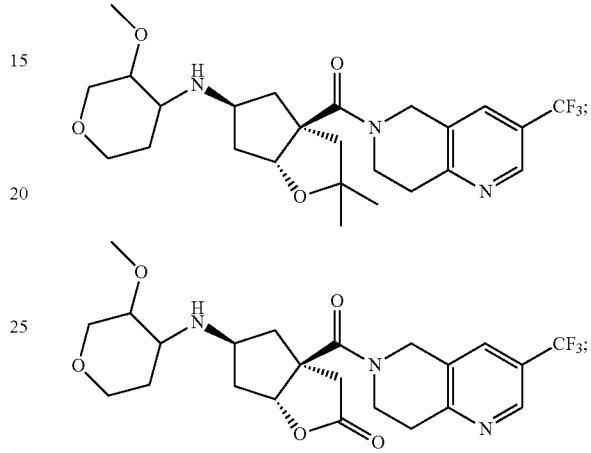
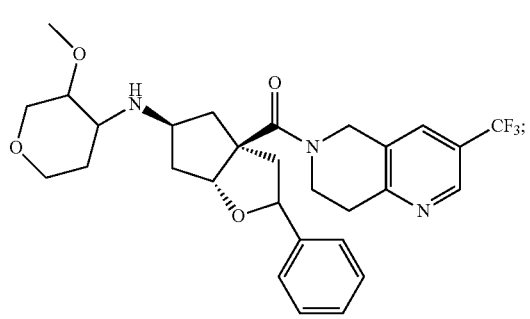
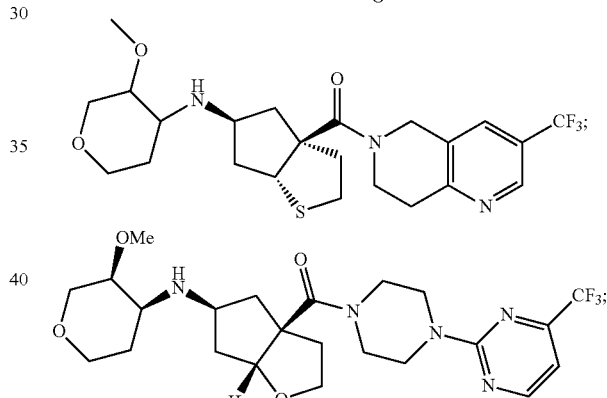
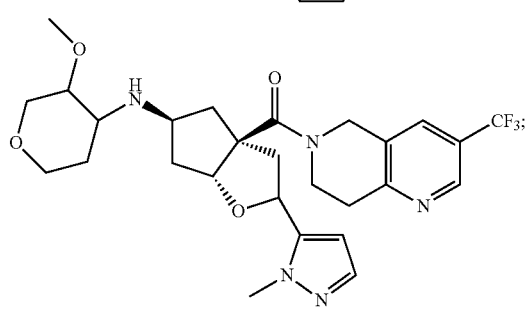
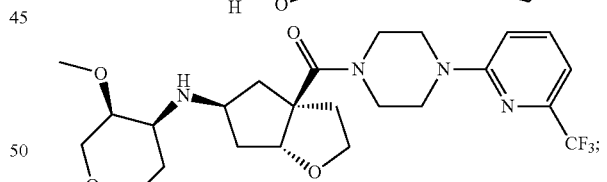
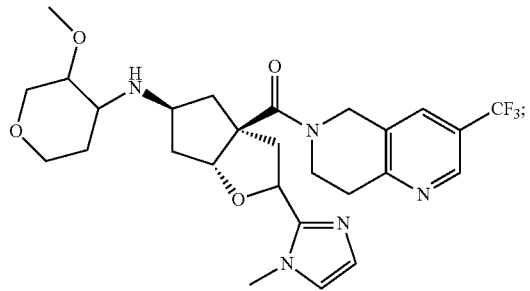
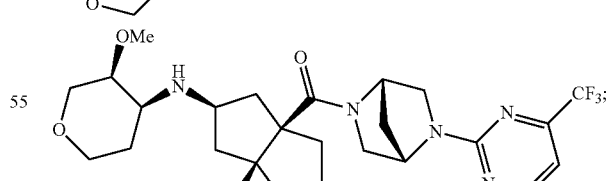
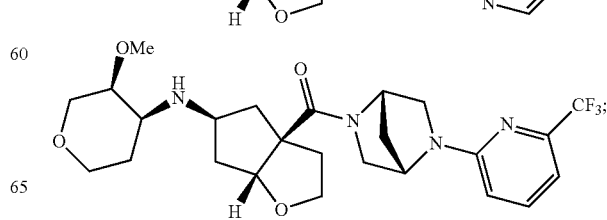

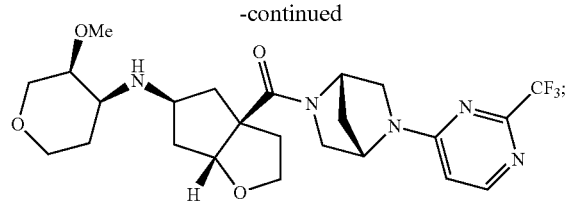
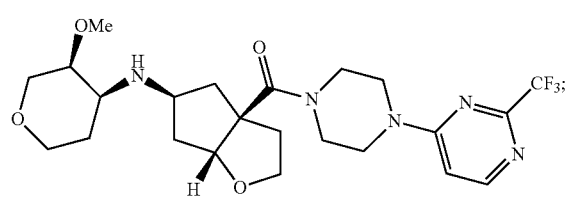
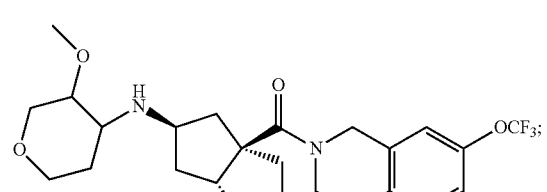
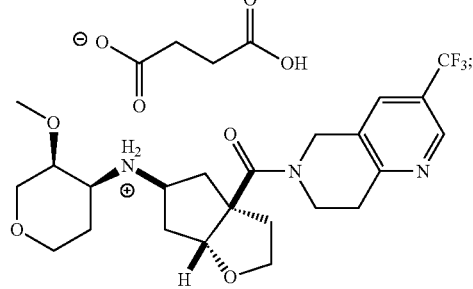
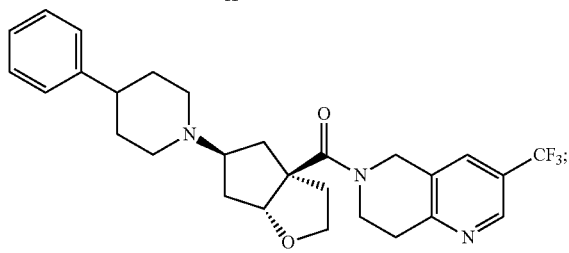
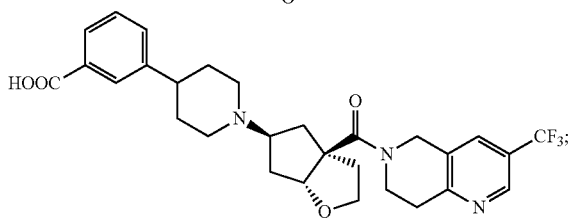
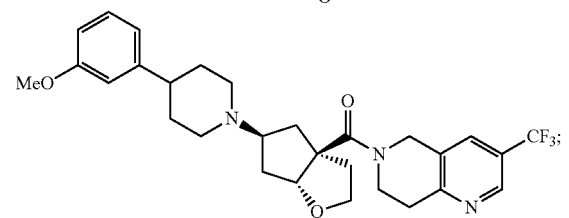
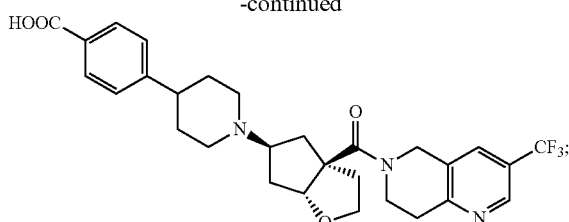
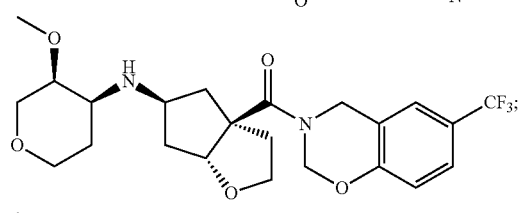
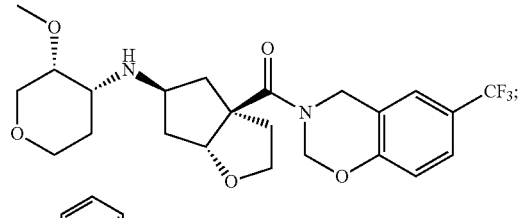
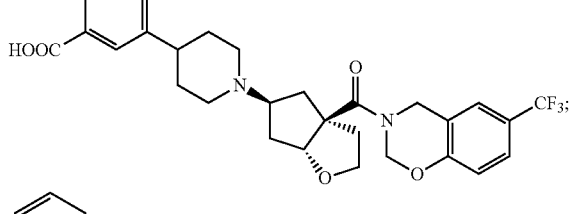
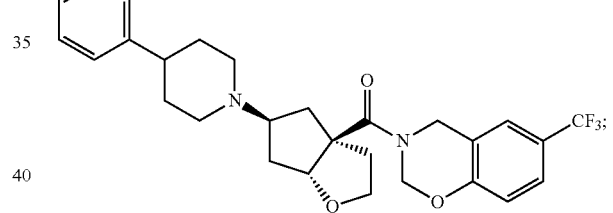
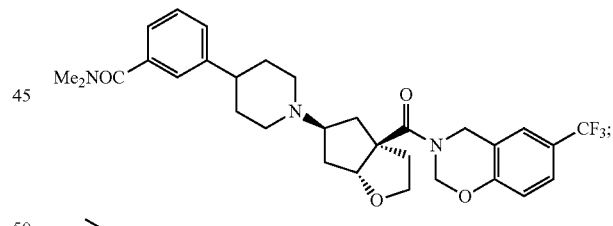
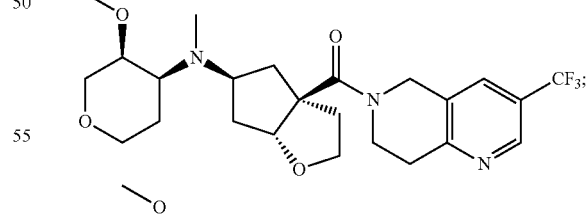
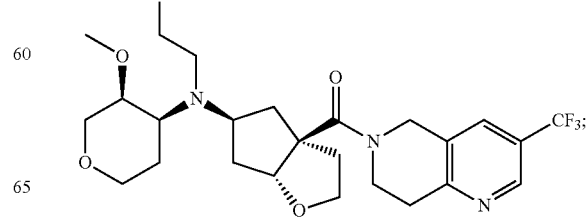

-continued

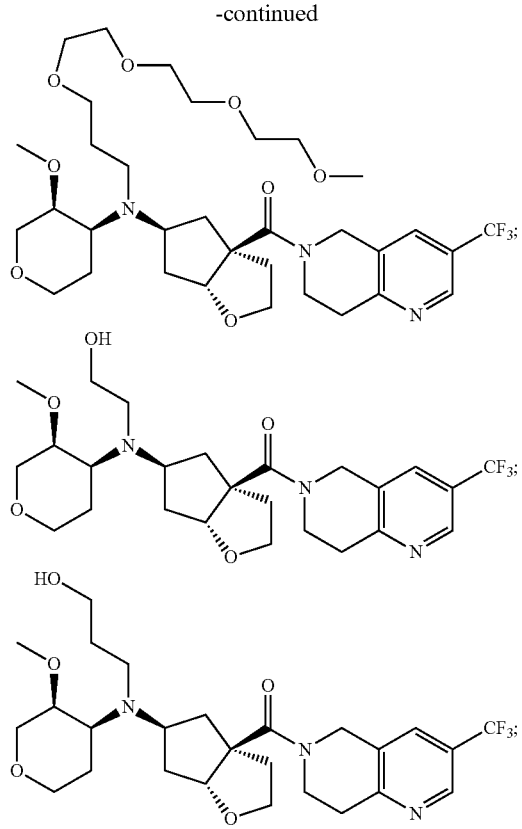

and pharmaceutically acceptable salts thereof.

In another embodiment, the present invention is directed to a compound of the formula

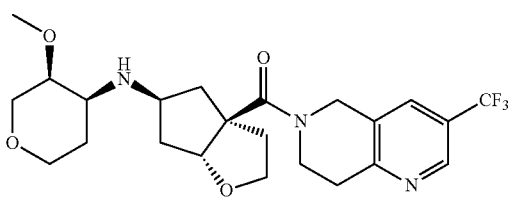 [SMILES: CO[C@@H]1COCC[C@@H]1N[C@@H]1C[C@H]2OCC[C@@]2(C(=O)N2CCc3ncc(C(F)(F)F)cc3C2)C1]

or a pharmaceutically acceptable salt thereof.

In another embodiment, the invention relates to a pharmaceutical composition, comprising a compound of formula (I) and a pharmaceutically acceptable carrier.

In another embodiment, the invention relates to a pharmaceutical composition made by mixing a compound of formula (I) and a pharmaceutically acceptable carrier.

In another embodiment, the invention relates to a process for making a pharmaceutical composition comprising mixing a compound of formula (I) and a pharmaceutically acceptable carrier.

The present invention is further directed to a product prepared according to any of the processes described herein. In another embodiment, the invention relates to the product prepared according to the process as described in Example 31, which follows herein.

In another embodiment, the present invention is directed to a process for the preparation of a compound of formula (I), as described in more detail in the Schemes and Examples which follow herein. In another embodiment, the present invention is directed to a process for the preparation of a compound of formula (I) as described in more detail in Example 31, which follows herein.

In another embodiment, the present invention relates to a compound selected from the group consisting of

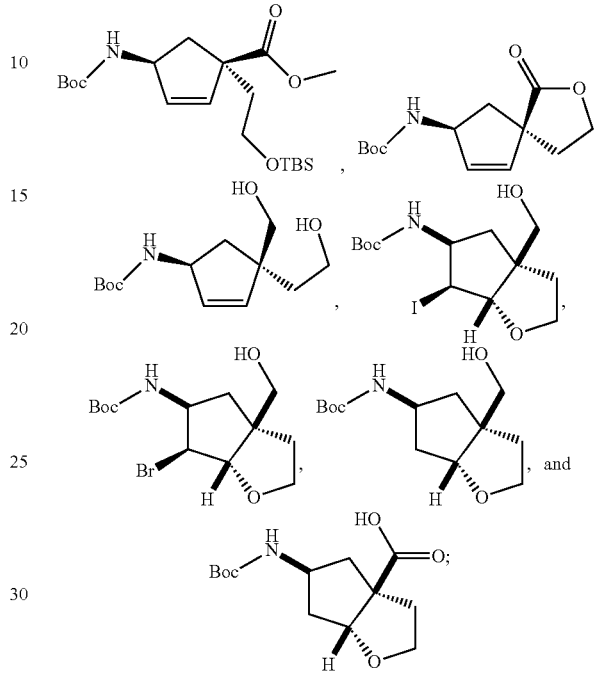

these compounds are useful as intermediates for the preparation of compounds of formula (I).

In another embodiment, the invention relates to intermediates useful for the preparation of a compound of formula (I), more particularly, compounds of formula (XIX)

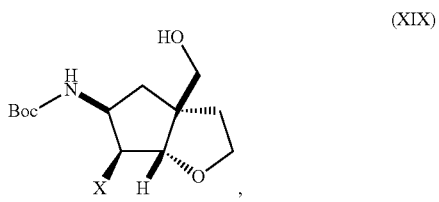

(XIX)

wherein X is Br, PhSe, or I.

In another embodiment, the present invention relates to a compound of formula (XXI)

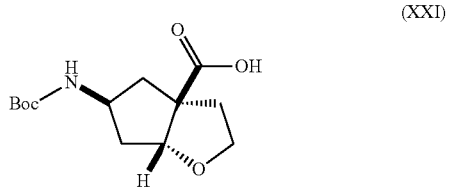 [SMILES: CC(C)(C)OC(=O)N[C@@H]1C[C@H]2OCC[C@@]2(C(=O)O)C1]

(XXI)

useful as an intermediate for the preparation of compounds of formula (I).

In another embodiment, the present invention relates to the process for making (S)-4,4-dimethoxytetrahydro-2H-pyran-3-ol comprising

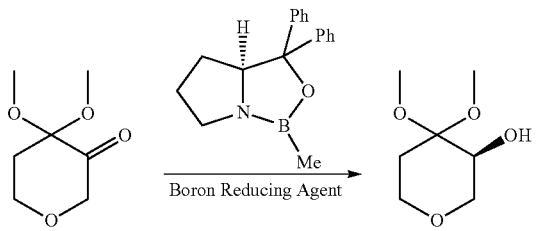 [SMILES: COC1(OC)CCOCC1=O ; CB1OC(c2ccccc2)(c2ccccc2)[C@@H]2CCCN12 ; COC1(OC)CCOC[C@@H]1O]

reacting 4,4-dimethoxydihydro-2H-pyran-3(4H)-one with a boron reducing agent and R-(+)-2-methyl-CBS-oxazaborolidine, over a period of at least six hours to provide the (S)-4,4-dimethoxytetrahydro-2H-pyran-3-ol in at least 60% enantiomeric excess.

In another embodiment, the present invention relates to the process for making (S)-4,4-dimethoxytetrahydro-2H-pyran-3-ol comprising

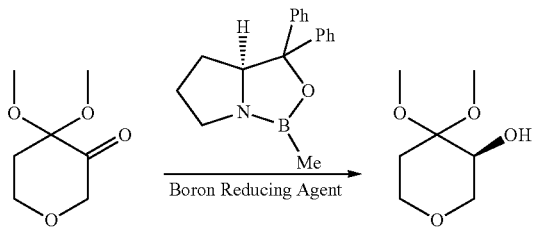 [SMILES: COC1(OC)CCOCC1=O ; CB1OC(c2ccccc2)(c2ccccc2)[C@@H]2CCCN12 ; COC1(OC)CCOC[C@@H]1O]

reacting 4,4-dimethoxydihydro-2H-pyran-3(4H)-one with a boron reducing agent and R-(+)-2-methyl-CBS-oxazaborolidine, over a period of at least six hours to provide the (S)-4,4-dimethoxytetrahydro-2H-pyran-3-ol in at least 90% enantiomeric excess.

In another embodiment, the present invention relates to the processes for making (S)-4,4-dimethoxytetrahydro-2H-pyran-3-ol, as described above, wherein the borane reducing complex is selected from borane-dimethylsulfide complex or borane-N,N-diethylaniline complex.

In another embodiment, the present invention relates to the processes for making (S)-4,4-dimethoxytetrahydro-2H-pyran-3-ol, as described above, wherein a THF solution of said borane-reducing complex and R-(+)-2-methyl-CBS-oxazaborolidine is added to a solution of the 4-dimethoxydihydro-2H-pyran-3(4H)-one in THF.

In another embodiment, the present invention relates to any of the processes for making (S)-4,4-dimethoxytetrahydro-2H-pyran-3-ol, as described above, wherein the reaction is carried out in an inert environment; in another embodiment of the invention, the inert environment is nitrogen gas.

In another embodiment, the present invention relates to any of the processes for making (S)-4,4-dimethoxytetrahydro-2H-pyran-3-ol, as described above, further comprising reacting the (S)-4,4-dimethoxytetrahydro-2H-pyran-3-ol with dimethyl sulfate to provide (R)-3,4,4-trimethoxytetrahydro-2H-pyran.

In another embodiment, the present invention relates to any of the processes for making (S)-4,4-dimethoxytetrahydro-2H-pyran-3-ol, as described above, further comprising reacting the (R)-3,4,4-trimethoxytetrahydro-2H-pyran with acid to provide (R)-3-methoxydihydro-2H-pyran-4(3H)-one. In another embodiment, the acid is concentrated hydrochloric acid.

In another embodiment, the present invention relates to the process for making (S)-4,4-dimethoxytetrahydro-2H-pyran-3-ol comprising

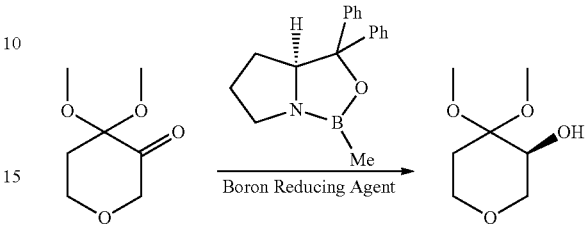

reacting 4,4-dimethoxydihydro-2H-pyran-3(4H)-one with a boron reducing agent and R-(+)-2-methyl-CBS-oxazaborolidine, over a period of at least six hours to provide the (S)-4,4-dimethoxytetrahydro-2H-pyran-3-ol in at least 60% enantiomeric excess, wherein the reaction is run at a temperature range from 20° C. to 60° C.

In another embodiment, the present invention relates to the process for making (R)-4,4-dimethoxytetrahydro-2H-pyran-3-ol comprising

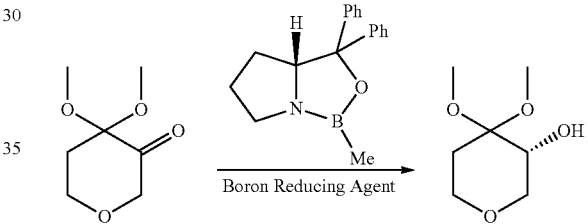

reacting 4,4-dimethoxydihydro-2H-pyran-3(4H)-one with a boron reducing agent and S-(−)-2-methyl-CBS-oxazaborolidine, over a period of at least six hours to provide the (R)-4,4-dimethoxytetrahydro-2H-pyran-3-ol in at least 60% enantiomeric excess.

In another embodiment, the present invention relates to the process for making (R)-4,4-dimethoxytetrahydro-2H-pyran-3-ol comprising

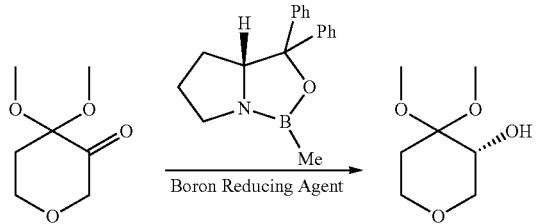 [SMILES: COC1(OC)CCOCC1=O ; CB1OC(c2ccccc2)(c2ccccc2)[C@H]2CCCN12 ; COC1(OC)CCOC[C@H]1O]

reacting 4,4-dimethoxydihydro-2H-pyran-3(4H)-one with a boron reducing agent and S-(−)-2-methyl-CBS-oxazaborolidine, over a period of at least six hours to provide the (R)-4,4-dimethoxytetrahydro-2H-pyran-3-ol, wherein (R)-4,4-dimethoxytetrahydro-2H-pyran-3-ol is formed in at least 90% enantiomeric excess.

In another embodiment, the present invention relates to the processes for making (R)-4,4-dimethoxytetrahydro-2H-pyran-3-ol, as described above, wherein the borane reducing complex is selected from borane-dimethylsulfide complex or borane-N,N-diethylaniline complex.

In another embodiment, the present invention relates to the processes for making (R)-4,4-dimethoxytetrahydro-2H-pyran-3-ol, as described above, wherein the THF solution of said borane-reducing complex and S-(−)-2-methyl-CBS-oxazaborolidine is added to a solution of the 4-dimethoxydihydro-2H-pyran-3(4H)-one in THF.

In another embodiment, the present invention relates to any of the processes for making (R)-4,4-dimethoxytetrahydro-2H-pyran-3-ol, as described above, wherein the reaction is carried out in an inert environment; in another embodiment of the invention, the inert environment is nitrogen gas.

In another embodiment, the present invention relates to any of the processes for making (R)-4,4-dimethoxytetrahydro-2H-pyran-3-ol, as described above, further comprising reacting the (R)-4,4-dimethoxytetrahydro-2H-pyran-3-ol with dimethyl sulfate to provide (S)-3,4,4-trimethoxytetrahydro-2H-pyran.

In another embodiment, the present invention relates to any of the processes for making (R)-4,4-dimethoxytetrahydro-2H-pyran-3-ol, as described above, further comprising reacting the (S)-3,4,4-trimethoxytetrahydro-2H-pyran with acid to provide (S)-3-methoxydihydro-2H-pyran-4(3H)-one. In another embodiment, the acid is concentrated hydrochloric acid.

In another embodiment, the present invention relates to any of the processes for making (R)-4,4-dimethoxytetrahydro-2H-pyran-3-ol, as described above, comprising

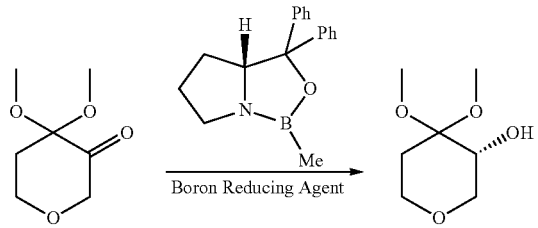 [SMILES: COC1(OC)CCOCC1=O ; CB1OC(c2ccccc2)(c2ccccc2)[C@H]2CCCN12 ; COC1(OC)CCOC[C@H]1O]

reacting 4,4-dimethoxydihydro-2H-pyran-3(4H)-one with a boron reducing agent and S-(−)-2-methyl-CBS-oxazaborolidine, over a period of at least six hours to provide the (R)-4,4-dimethoxytetrahydro-2H-pyran-3-ol in at least 60% enantiomeric excess, wherein the reaction is run at a temperature range from 20° C. to 60° C.

In another embodiment, the invention relates to a method for preventing, treating or ameliorating a CCR2 mediated syndrome, disorder or disease comprising administering to a subject in need thereof a therapeutically effective amount of a compound of formula (I).

In another embodiment, the invention relates to a method for preventing, treating or ameliorating a CCR2 mediated inflammatory syndrome, disorder or disease wherein the syndrome, disorder or disease is associated with elevated MCP-1 expression or MCP-1 overexpression, or is an inflammatory condition that accompanies syndromes, disorders or diseases associated with elevated MCP-1 expression or MCP-1 overexpression comprising administering to a subject in need thereof an effective amount of a compound of claim 1.

In another embodiment, the invention relates to a method of preventing, treating or ameliorating a syndrome, disorder or disease, wherein said syndrome, disorder or disease is selected from the group consisting of: Chronic Obstructive Pulmonary Disease (COPD), ophthalmic disorders, uveitis, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, type-I diabetes, type II diabetes, diabetic complications, diabetic nephropathy, diabetic retinopathy, diabetic retinitis, diabetic microangiopathy, overweight, obesity, obesity-associated insulin resistance, metabolic syndrome, tuberculosis, sarcoidosis, invasive staphyloccocia, inflammation after cataract surgery, allergic rhinitis, allergic conjunctivitis, chronic urticaria, asthma, allergic asthma, periodontal diseases, periodontitis, gingivitis, gum disease, diastolic cardiomyopathies, cardiac infarction, myocarditis, chronic heart failure, angiostenosis, restenosis, reperfusion disorders, aortic abdominal aneurism, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach and chronic neuroinflammatory disorders including, but not limited to, Alzheimer's disease, ischemic stroke, spinal cord injury, nerve crush injury and traumatic brain injury comprising administering to a subject in need thereof an effective amount of a compound of formula (I).

In another embodiment, the invention relates to a method of preventing, treating or ameliorating a syndrome, disorder or disease, wherein said syndrome, disorder or disease is selected from the group consisting of: type I diabetes, type II diabetes, diabetic complications, diabetic nephropathy, diabetic retinopathy, diabetic retinitis, diabetic microangiopathy, obesity, obesity-associated insulin resistance, metabolic syndrome, asthma, and allergic asthma, comprising administering to a subject in need thereof a therapeutically effective amount of a compound of formula (I).

In another embodiment, the invention relates to a method of treating a disorder selected from the group consisting of type II diabetes, obesity and asthma comprising administering to a subject in need thereof a therapeutically effective amount of a compound of formula (I).

The present invention is further directed to a succinate salt of a compound of formula (I-S)

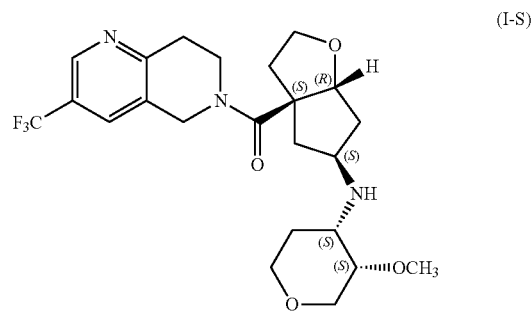

wherein the compound of formula (I-S) is also known as ((3aS,5S,6aR)-5-(((3S,4S)-3-methoxytetrahydro-2H-pyran-4-yl)amino)hexahydro-2H-cyclopenta[b]furan-3a-yl)(3-(trifluoromethyl)-7,8-dihydro-1,6-naphthyridin-6(5H)-yl) methanone. In an embodiment, the succinate salt of the compound of formula (I-S) is crystalline. In another embodiment, the succinate salt of the compound of formula (I-S) is a crystalline hydrate form; wherein the hydrate contains about 0.6 moles water per mole of the compound of formula (I-S). In another embodiment of the present invention, the succinate salt of the compound of formula (I-S) is crystalline hydrate form containing about 0.6 moles water per mole of the compound of formula (I-S); wherein the crystalline hydrate form is further hygroscopic.

The present invention is also directed to a crystalline succinate salt of the compound of formula (I-S), wherein the acidic counter-ion is succinic acid. Additional salt screening was performed on the compound of formula (I-S), using the following additional acidic counter-ions: HCl acid, sulfuric acid, citric acid, malonic acid, maleic acid, L-tartaric acid, p-toluenesulfonic acid, phosphoric acid and acetic acid. X-ray analysis of the resulting solid residues indicated crystalline structures for the sulfate, maleate and phosphate salts; and amorphous structures of the HCl, citrate, malonate, tartrate and tosylate salts.

The crystalline phosphate, sulfate and maleate salts of the compound of formula (I-S) were additional tested in DSC, TGA and moisture sorption/desorption. The sulfate salt showed inter-conversion between salt forms and hygroscopic weight increase of 1.6% up to 60% RH and a total of 26.5% up to 90% RH, with strong hysteresis. The maleate salt showed a form change and hygroscopic weight increase of 18.3% up to 70% RH and a total of 79.9% up to 90% RH. The phosphate salt showed hygroscopic weight increase of 3.3% up to 60% RH and a total of 69.4% up to 90% RH, with strong hysteresis and deliquescence.

DEFINITIONS

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

The term "cycloalkyl" refers to a saturated or partially unsaturated monocyclic or bicyclic hydrocarbon ring radical derived by the removal of one hydrogen atom from a single ring carbon atom. Examples of cycloalkyl radicals include, but are not limited to cyclopropyl, cyclobutyl, cyclopentyl, cyclopentenyl, cyclohexyl, cyclohexenyl, cycloheptyl and cyclooctyl. Additional examples include $C_{(3-8)}$cycloalkyl, $C_{(5-8)}$cycloalkyl, $C_{(3-12)}$cycloalkyl, $C_{(3-20)}$cycloalkyl, decahydronaphthalenyl, and 2,3,4,5,6,7-hexahydro-1H-indenyl.

The term "boron reducing agent" refers to a boron hydride, often with stabilizers such as ethers, amines, or sulfides. Examples of boron reducing agents include, but are not limited to, borane-tetrahydrofuran complex, catecholborane, borane-dimethyl aniline complex, and borane-dimethyl sulfide complex.

The term "heteroaryl" refers to a radical derived by the removal of one hydrogen atom from a ring carbon atom of a heteroaromatic ring system. A heteroaromatic ring system shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure. Examples of heteroaryl radicals include, but are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolizinyl, indolyl, isoindolyl, benzo[b]furyl, benzo[b]thienyl, indazolyl, benzimidazolyl, benzthiazolyl, purinyl, 4H-quinolizinyl, quinolinyl, isoquinolinyl, cinnolinyl, phthalzinyl, quinazolinyl, quinoxalinyl, 1,8-naphthyridinyl, and pteridinyl.

The term "ee" or "enantiomeric excess" is the absolute value of the difference in mole fractions of a mixture of enantiomers. The mole fraction of the (+)- and (−)-enantiomers are expressed as F(+) and F(−) (where F(+)+F(−)=1). The enantiomeric excess is defined as |F(+)−F(−)|. The percent enantiomeric excess is the ee*100. For example a 50/50 mixture of (+) and (−) enantiomers has 0% ee, a 5/95 mixture of (+) and (−) enantiomers has a 90% ee, and a 70/30 mixture of (+) and (−) enantiomers has a 40% ee.

The term "inert environment" is a local environment for chemical reactions which is substantially depleted of atmospheric oxygen and water vapor. For example, a reaction run under an inert environment includes, but is not limited to, reactions run under argon or nitrogen atmosphere.

The term "isolated form" shall mean that the compound is present in a form which is separate from any solid mixture with another compound(s), solvent system or biological environment. In an embodiment, the present invention is directed to a succinate salt of the compound of formula (I-S), preferably a crystalline succinate salt of the compound of formula (I-S), wherein the salt is present and/or prepared as an isolated form.

The term "substantially free of other salt form(s)" when used to describe the succinate salt of the compound of formula (I-S) shall mean that mole percent of any other salt form(s) in the isolated succinate salt of the compound of formula (I-S) is less than about 5 mole percent, preferably less than about 2 mole percent, more preferably, less than about 0.5 mole percent, most preferably less than about 0.1 mole percent. In an embodiment, the present invention is directed to a succinate salt of the compound of formula (I-S), preferably a crystalline succinate salt of the compound of formula (I-S), wherein the salt is present and/or prepared as form which is substantially free of other salt form(s).

The term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment, the present invention is directed to a succinate salt of the compound of formula (I-S), preferably a crystalline succinate salt of the compound of formula (I-S), wherein the salt is present and/or prepared as a substantially pure form.

For use in medicines, the salts of the compounds of this invention refer to non-toxic "pharmaceutically acceptable salts." FDA approved pharmaceutically acceptable salt forms (Ref International J. Pharm. 1986, 33, 201-217; J. Pharm. Sci., 1977, January, 66(1), p1) include pharmaceutically acceptable acidic/anionic or basic/cationic salts.

Throughout this specification, compounds are described as being separated, usually by silica gel column, although preporatory thin layer chromatography, or high or low pressure liquid choromatography may also be used. It is generally accepted that when eluting compounds through a silica gel-type separation medium, that the least polar compounds elute before the more polar compounds. Therefore, the term "less polar isomer", refers to the isomer that will elute first from a silica gel type separation medium.

Abbreviations

Herein and throughout this application, the following abbreviations may be used.

AIBN azobisisobutyronitrile
BOC or Boc tert-butyloxycarbonyl
DCC dicyclohexylcarbodiimide
DCM dicholomethane
EDCI or EDC 1-ethyl-3-(3'-dimethylaminopropyl)carbodiimide
DIAD diisopropylazodicarboxylate
DIEA diisopropylethylamine
DSC differential scanning calorimetry
Et ethyl
EtOAc ethyl acetate
ee enantiomeric excess
eq equivalents
HOBt hydroxybenzotriazole
LiHMDS lithium bis(trimethylsilyl)amide
M moles/liter
Me methyl
MIBK methyl isobutyl ketone
min. minutes
n-BuLi n-butyl lithium
NBS or NIS N-bromo succinimide or N-iodo succinimide
OAc acetate
Ph phenyl
PyBrop bromo-tris-pyrrolidinophosphonium hexafluorophosphate
RH relative humidity
rt room temperature
TBAF tetrabutylammonium fluoride
TFA trifluoroacetic acid
THF tetrahydrofuran
TBS or TBDMS tertbutyldimethylsilyl
TLC thin layer chromatography

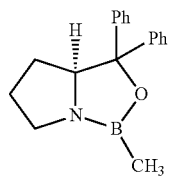

S-(-)-2-methyl-CBS-oxazaborolidine

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate (SEH), sodium hydroxide, triethanolamine or zinc.

Methods of Use

The present invention is directed to a method for preventing, treating or ameliorating a CCR2 mediated syndrome, disorder or disease comprising administering to a subject in need thereof an effective amount of a compound of Formula (I) or a form, composition or medicament thereof.

Examples of a CCR2 mediated syndrome, disorder or disease for which the compounds of Formula (I) are useful include chronic obstructive pulmonary disorder (COPD), ophthalmic disorders, uveitis, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, type-I diabetes, type II diabetes, diabetic complications, diabetic nephropathy, diabetic retinopathy, diabetic retinitis, diabetic microangiopathy, overweight, obesity, obesity-associated insulin resistance, metabolic syndrome, tuberculosis, chronic obstructive pulmonary disease, sarcoidosis, invasive staphyloccocia, inflammation after cataract surgery, allergic rhinitis, allergic conjunctivitis, chronic urticaria, asthma, allergic asthma, periodontal diseases, periodontis, gingivitis, gum disease, diastolic cardiomyopathies, cardiac infarction, myocarditis, chronic heart failure, angiostenosis, restenosis, reperfusion disorders, aortic abdominal aneurism, multiple sclerosis, glomerulonephritis, solid tumors and cancers, chronic lymphocytic leukemia, chronic myelocytic leukemia, multiple myeloma, malignant myeloma, Hodgkin's disease, carcinomas of the bladder, breast, cervix, colon, lung, prostate, or stomach, and chronic neuroinflammatory disorders including, but not limited to, Alzheimer's disease, ischemic stroke, spinal cord injury, nerve crush injury and traumatic brain injury.

Some of the quantitative expressions given herein are qualified with the term "about". It is understood that whether the term "about" is used explicitly or not, every quantity given herein is meant to refer to both the actual given value and the approximation to such given value that would reasonably be inferred based on the ordinary skill in the art, including approximations due to the experimental and/or measurement conditions for such given value. In addition, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

The term "administering" with respect to the methods of the invention, means a method for therapeutically or prophylactically preventing, treating or ameliorating a syndrome, disorder or disease as described herein by using a compound of Formula (I) or a form, composition or medicament thereof.

Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be animal, typically a mammal, typically a human, which has been the object of treatment, observation or experiment. In one aspect of the invention, the subject is at risk of (or susceptible to) developing a syndrome, disorder or disease that is associated with elevated MCP-1 expression or MCP-1 overexpression, or a patient with an inflammatory condition that accompanies syndromes, disorders or diseases associated with elevated MCP-1 expression or MCP-1 overexpression.

The term "therapeutically effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

The term "uveitis" generically refers to any inflammatory disease involving the eye. Uveitis can be divided into clinically distinct subtypes based on the part of the eye in which the inflammation is present (percentages correspond to patients known to fit these categories): anterior (51%), intermediate (13%), posterior (20%), or panuveitis (16%) and, according to the course of the disease, as either acute (16%), recurring (26%), or chronic (58%). Those with anterior uveitis (0.19%) eventually develop irreparable vision damage despite aggressive treatment such as unilateral blindness (9%), bilateral blindness (2%), or unilateral or bilateral vision impairment (8%). Most cases of uveitis are idiopathic, but known causes include infection (e.g., toxoplasmosis, cytomegalovirus, and the like) or development as a component of a systemic inflammatory and/or autoimmune disorder (e.g., juvenile RA, HLA-B27 associated spondyloarthropathies, sarcoidosis, and the like). (HLA-B27: Human Leukocyte Antigen B*27—is a class I surface antigen encoded by the B locus in the major histocompatibility complex (MHC) on chromosome 6 and presents microbial antigens to T cells. HLA-B27 is strongly associated with a certain set of autoimmune diseases referred to as the seronegative spondyloarthropathies.)

When employed as CCR2 inhibitors, the compounds of the invention may be administered in an effective amount within the dosage range of about 0.5 mg to about 10 g, or any amount or range therein, preferably between about 0.5 mg to about 5 g, or any amount or range therein, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula (I) may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula (I) include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention. As used herein, the term "composition" is intended to encompass a product comprising the specified ingredients in the specified amounts, as well as any product which results, directly or indirectly, from combinations of the specified ingredients in the specified amounts.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in the Examples of Formula (I) for use as a medicament.

In another embodiment, the invention relates to the use of a compound as described in the Examples of Formula (I) for the preparation of a medicament for the treatment of a disease associated with an elevated or inappropriate CCR2 activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Preparation of Crystalline Succinate Salt of the Compound of Formula (I-S)

The crystalline succinate salt of the compound of formula (I-S) of the present invention may be prepared from the corresponding amorphous succinate salt of the compound of formula (I-S) by heating to a temperature in the range of from about 140° C. to about 150° C., preferably to about 140° C., and then cooling to about room temperature to effect crystallization, as described in more detail in Example 52, which follows herein.

Alternatively, the crystalline succinate salt of the compound of formula (I-S) of the present invention may be prepared from the corresponding amorphous succinate salt of the compound of formula (I-S) by crystallization from a suitably selected solvent such as methyl isobutyl ketone (MIBK), as described in more detail in Example 53, which follow herein. For the crystallization of the succinate salt of the compound of formula (I-S) the suitably selected solvent is other than water, methanol, ethanol, acetone, acetonitrile. isopropyl acetate, nitromethane, tetrahydrofuran, methyl ethyl ketone, dichloromethane, toluene, methyl isopropyl ketone (MIPK).

The amorphous succinate salt of the compound of formula (I-S) may be prepared, for example, as described in Example 30, which follows herein.

Powder X-Ray Diffraction (pXRD)

The succinate salt of the compound of formula (I-S) was characterized as to its powder X-ray diffraction pattern (pXRD), in example as follows. The sample was examined using an X-ray diffractometer (Philips Model X'PERT PRO PW3040) with X'Celerator detector and graded multilayer parabolic X-ray mirror. The samples were scanned from 3 to 40° 2θ, at a step size 0.0165° 2θ and a time per step of 2000.025 seconds. The tube voltage and current were 45 KV and 40 mA, respectively. The sample was packed on a zero background XRD-holder and scanned under ambient temperature and humidity conditions.

A pXRD spectrum was measured for a representative sample of the crystalline succinate salt of the compound of formula (I-S), as shown in FIG. 1. In an embodiment, the crystalline succinate salt of the compound of formula (I-S) may be characterized by its powder X-ray diffraction pattern, which comprised the peaks listed in Table 1, below.

TABLE 1 pXRD Peaks:
Crystalline Succinate Salt of Compound of Formula (I-S)

| Position [°2θ] | d-spacing [Å] | Relative Intensity [%] |
|---|---|---|
| 7.27 | 12.17 | 3 |
| 10.03 | 8.82 | 4 |
| 10.51 | 8.42 | 4 |
| 11.27 | 7.85 | 8 |
| 12.26 | 7.22 | 2 |
| 13.87 | 6.38 | 67 |
| 14.34 | 6.18 | 21 |
| 14.63 | 6.05 | 16 |
| 15.96 | 5.55 | 17 |
| 16.73 | 5.30 | 11 |
| 17.66 | 5.02 | 13 |
| 18.33 | 4.84 | 16 |
| 19.22 | 4.62 | 100 |
| 19.78 | 4.49 | 36 |
| 20.11 | 4.42 | 36 |
| 20.86 | 4.26 | 26 |
| 21.34 | 4.16 | 20 |
| 22.01 | 4.04 | 50 |
| 22.67 | 3.92 | 16 |
| 23.62 | 3.77 | 15 |
| 24.14 | 3.69 | 8 |
| 25.78 | 3.46 | 17 |
| 27.07 | 3.29 | 14 |
| 27.64 | 3.23 | 7 |
| 28.40 | 3.14 | 6 |
| 28.97 | 3.08 | 4 |
| 30.30 | 2.95 | 4 |
| 31.91 | 2.80 | 3 |

TABLE 1-continued pXRD Peaks:
Crystalline Succinate Salt of Compound of Formula (I-S)

| Position [°2θ] | d-spacing [Å] | Relative Intensity [%] |
|---|---|---|
| 33.34 | 2.69 | 4 |
| 35.91 | 2.50 | 4 |

In an embodiment, the crystalline succinate salt of the compound of formula (I-S) is characterized by its pXRD pattern which comprises peaks having a relative intensity greater than or equal to about 3%, as listed in Table 2, below.

TABLE 2 pXRD Peaks:
Crystalline Succinate Salt of Compound of Formula (I-S)

| Position [°2θ] | d-spacing [Å] | Relative Intensity [%] |
|---|---|---|
| 10.03 | 8.82 | 4 |
| 10.51 | 8.42 | 4 |
| 11.27 | 7.85 | 8 |
| 12.26 | 7.22 | 2 |
| 13.87 | 6.38 | 67 |
| 14.34 | 6.18 | 21 |
| 14.63 | 6.05 | 16 |
| 15.96 | 5.55 | 17 |
| 16.73 | 5.30 | 11 |
| 17.66 | 5.02 | 13 |
| 18.33 | 4.84 | 16 |
| 19.22 | 4.62 | 100 |
| 19.78 | 4.49 | 36 |
| 20.11 | 4.42 | 36 |
| 20.86 | 4.26 | 26 |
| 21.34 | 4.16 | 20 |
| 22.01 | 4.04 | 50 |
| 22.67 | 3.92 | 16 |
| 23.62 | 3.77 | 15 |
| 24.14 | 3.69 | 8 |
| 25.78 | 3.46 | 17 |
| 27.07 | 3.29 | 14 |
| 27.64 | 3.23 | 7 |
| 28.40 | 3.14 | 6 |
| 28.97 | 3.08 | 4 |
| 30.30 | 2.95 | 4 |
| 33.34 | 2.69 | 4 |
| 35.91 | 2.50 | 4 |

In an embodiment, the crystalline succinate salt of the compound of formula (I-S) is characterized by its pXRD pattern which comprises peaks having a relative intensity greater than or equal to about 5%, as listed in Table 3, below.

TABLE 3 pXRD Peaks:
Crystalline Succinate Salt of Compound of Formula (I-S)

| Position [°2θ] | d-spacing [Å] | Relative Intensity [%] |
|---|---|---|
| 11.27 | 7.85 | 8 |
| 12.26 | 7.22 | 2 |
| 13.87 | 6.38 | 67 |
| 14.34 | 6.18 | 21 |
| 14.63 | 6.05 | 16 |
| 15.96 | 5.55 | 17 |
| 16.73 | 5.30 | 11 |
| 17.66 | 5.02 | 13 |
| 18.33 | 4.84 | 16 |
| 19.22 | 4.62 | 100 |
| 19.78 | 4.49 | 36 |
| 20.11 | 4.42 | 36 |
| 20.86 | 4.26 | 26 |
| 21.34 | 4.16 | 20 |

TABLE 3-continued pXRD Peaks:
Crystalline Succinate Salt of Compound of Formula (I-S)

| Position [°2θ] | d-spacing [Å] | Relative Intensity [%] |
|---|---|---|
| 22.01 | 4.04 | 50 |
| 22.67 | 3.92 | 16 |
| 23.62 | 3.77 | 15 |
| 24.14 | 3.69 | 8 |
| 25.78 | 3.46 | 17 |
| 27.07 | 3.29 | 14 |
| 27.64 | 3.23 | 7 |
| 28.40 | 3.14 | 6 |

In an embodiment, the crystalline succinate salt of the compound of formula (I-S) is characterized by its pXRD pattern which comprises peaks having a relative intensity greater than or equal to about 10%, as listed in Table 4, below.

TABLE 4 pXRD Peaks:
Crystalline Succinate Salt of Compound of Formula (I-S)

| Position [°2θ] | d-spacing [Å] | Relative Intensity [%] |
|---|---|---|
| 13.87 | 6.38 | 67 |
| 14.34 | 6.18 | 21 |
| 14.63 | 6.05 | 16 |
| 15.96 | 5.55 | 17 |
| 16.73 | 5.30 | 11 |
| 17.66 | 5.02 | 13 |
| 18.33 | 4.84 | 16 |
| 19.22 | 4.62 | 100 |
| 19.78 | 4.49 | 36 |
| 20.11 | 4.42 | 36 |
| 20.86 | 4.26 | 26 |
| 21.34 | 4.16 | 20 |
| 22.01 | 4.04 | 50 |
| 22.67 | 3.92 | 16 |
| 23.62 | 3.77 | 15 |
| 25.78 | 3.46 | 17 |
| 27.07 | 3.29 | 14 |

In another embodiment, the present invention is directed to a crystalline succinate salt of the compound of formula (I-S) as characterized by the following pXRD peak, listed in ° 2θ: 10.03, 10.51, 11.27, 13.87, 19.22 and 22.01. In another embodiment, the present invention is directed to a crystalline succinate salt of the compound of formula (I-S) as characterized by the following pXRD peak, listed in ° 2θ: 11.27, 13.87, 19.22 and 22.01.

Differential Scanning Calorimetry (DSC)

The crystalline succinate salt of the compound of formula (I-S) was further subjected to DSC analysis. A representative sample was tested using a TA Instruments Model Q1000 differential scanning calorimeter. The sample was analyzed as received in an open aluminum pan. The DSC was programmed to heat from 25° C. to 300° C. at a heating rate of 10° C./min with a nitrogen purge.

Figure 2:
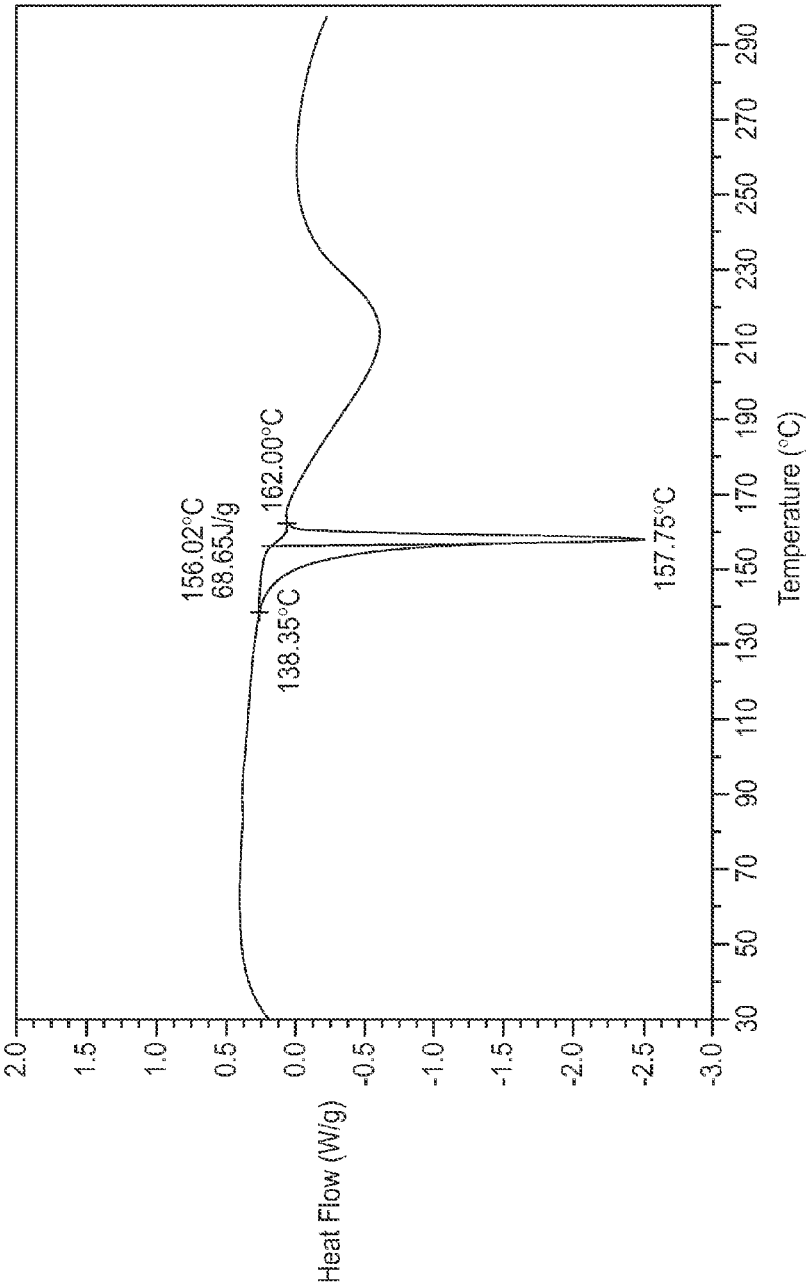
FIG. 2 illustrates a representative DSC scan for the crystalline succinate salt of the compound of formula (I-S)

Thermal analysis (via DSC scanning) was completed for a representative sample of the crystalline succinate salt of the compound of formula (I-S), as shown in FIG. 2. The crystalline succinate salt of the compound of formula (I-S) exhibited an onset melting temperature of about 156° C., a peak temperature of melting of about 158° C. and an enthalpy 68.3 J/g.

Thermogravimetric Analysis (TGA)

The crystalline succinate salt of the compound of formula (I-S) was further subjected to TGA analysis. A representative sample was tested, as received, for total weight loss using a TA Instruments Model Q5000IR TGA thermogravimetric calorimeter. The sample was placed in a tarred aluminum pan, automatically weighed and inserted into the TGA furnace.

The sample was scanned from 25° C. to 300° C. at a heating rate of 10° C./min with a 90 mL/min nitrogen purge and a 10 mL/min helium balance purge.

Figure 3:
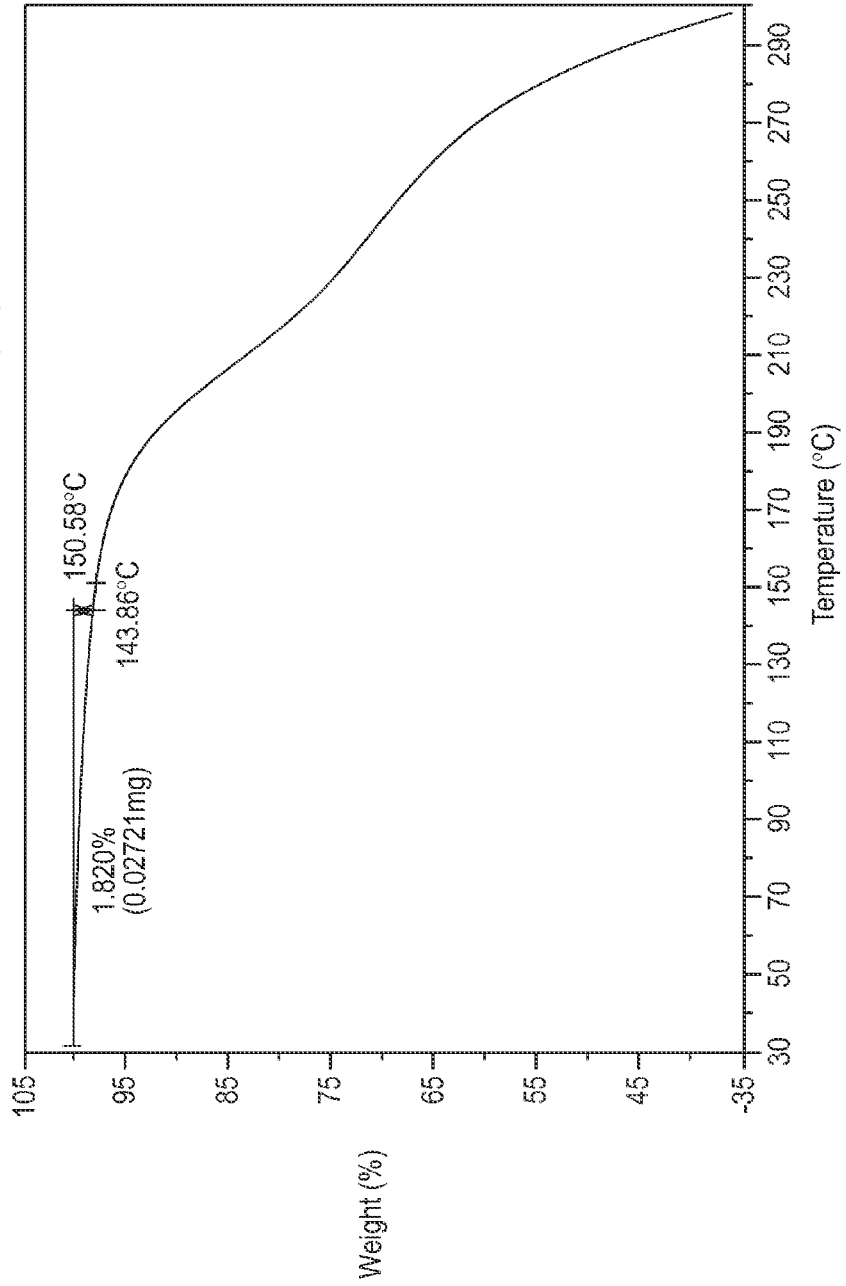
FIG. 3 illustrates a representative TGA scan for the crystalline succinate salt of the compound of formula (I-S)

A TGA trace was measured for a representative sample of the crystalline succinate salt of the compound of formula (I-S), as shown in FIG. 3. A 1.8% weight loss was observed between room temperature and 144° C., due to dehydration/desolvation; followed by decomposition at 151° C. These results indicate that the crystalline succinate salt of the compound of formula (I-S) is hydrate; wherein the hydrate contains about 0.6 moles of water per mole of the compound of formula (IS).

Moisture Isothermal Analysis

The crystalline succinate salt of the compound of formula (I-S) was further subjected to moisture sorption analysis. The moisture sorption analysis was performed using Hiden Isochema system Model IGAsorp. The sample (~5 mg) was run in a stainless-steel mesh crucible. The sample was initially dried at 60° C. for 30 minutes, then the moisture profile was evaluated by monitoring vapor adsorption/desorption over the range of 0% RH to 90% RH at 25° C. The moisture profile consisted of 2 cycles of vapor adsorption/desorption.

Figure 4:
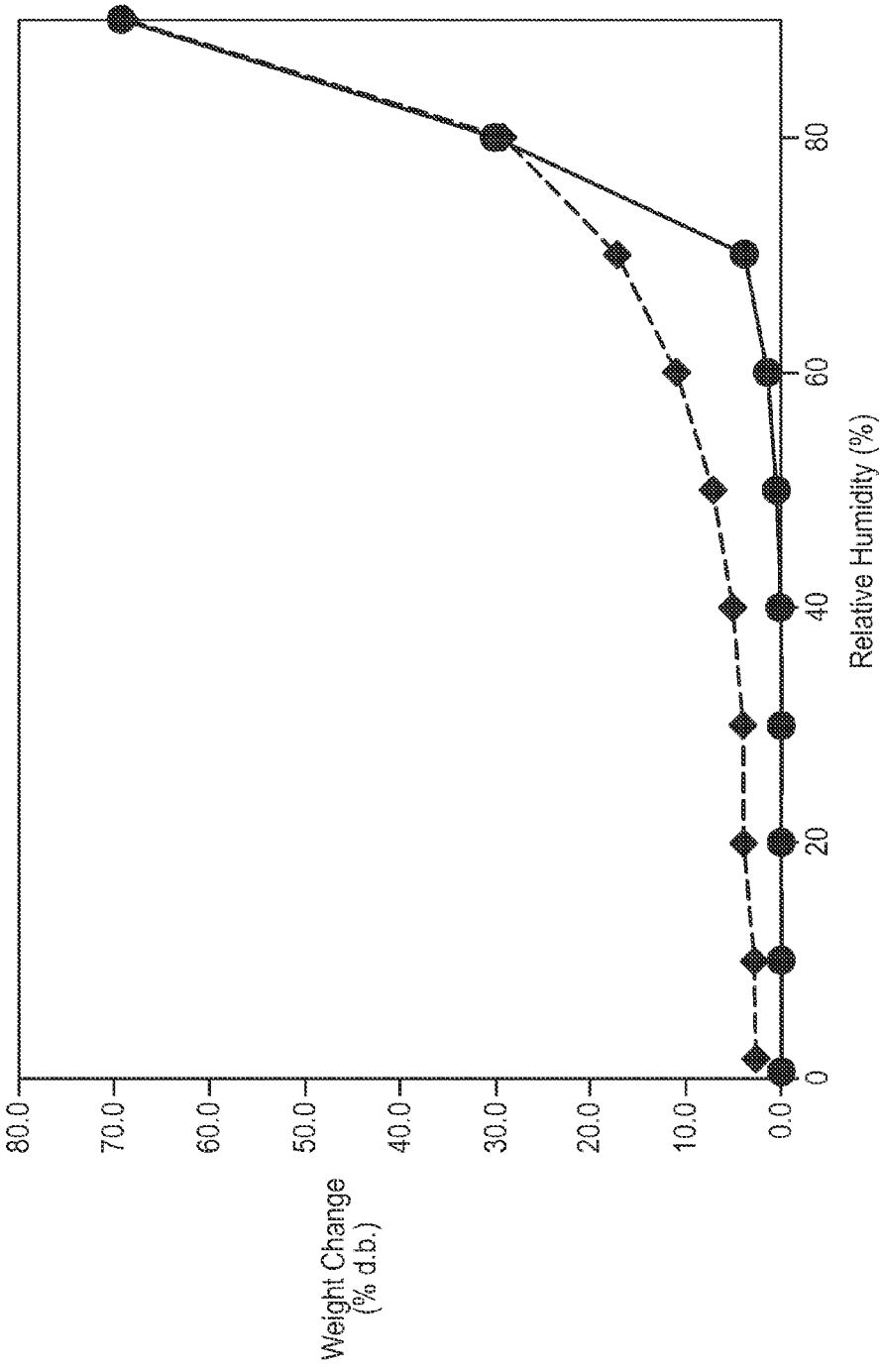
FIG. 4 illustrates a representative moisture isotherm for the crystalline succinate salt of the compound of formula (I-S).

FIG. 4 illustrates two cycles of vapor sorption/desorption for a representative sample of the crystalline succinate salt of the compound of formula (I-S). The weight of the sample increased 3.8% up to 70% RH, with a total of 70% uptake up to 90% RH. Further, strong hysteresis was observed in the multiple sorption/desorption cycles with about 2.7% moisture (equivalent to 0.9 moles of water) retained at the end of the desorption phase. Thus, the crystalline succinate salt of the compound of formula (I-S) is hygroscopic.

Solubility

The crystalline succinate salt of the compound of formula (I-S) was tested for solution solubility and measured to be soluble at >50 mg/ml in water and at >100 mg/ml in 0.1N NaOH, pH 2, pH4 and pH6 citrate buffers; in pH 8 and pH 10 borate buffers; simulated intestinal fluid, simulated gastric fluid; 0.5% methocel and 20% HpbCD.

General Reaction Scheme

Representative compounds of the present invention can be synthesized in accordance with the general synthetic methods described below. Compounds of Formula (I) can be prepared by methods known to those who are skilled in the art. The following reaction schemes are only meant to represent examples of the invention and are in no way meant to be a limit of the invention.

Compounds of Formula (I) wherein A is O and wherein $R^0$, $R^2$ and $R^3$ are each hydrogen may be prepared according to the processes outlined in Scheme 1.

Scheme 1

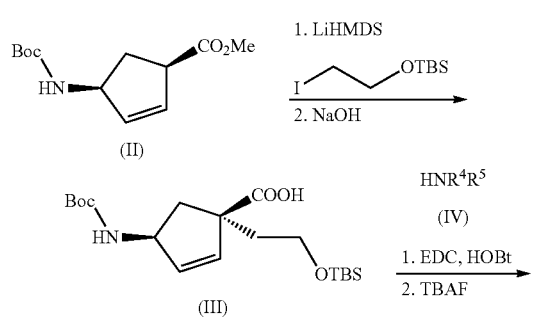

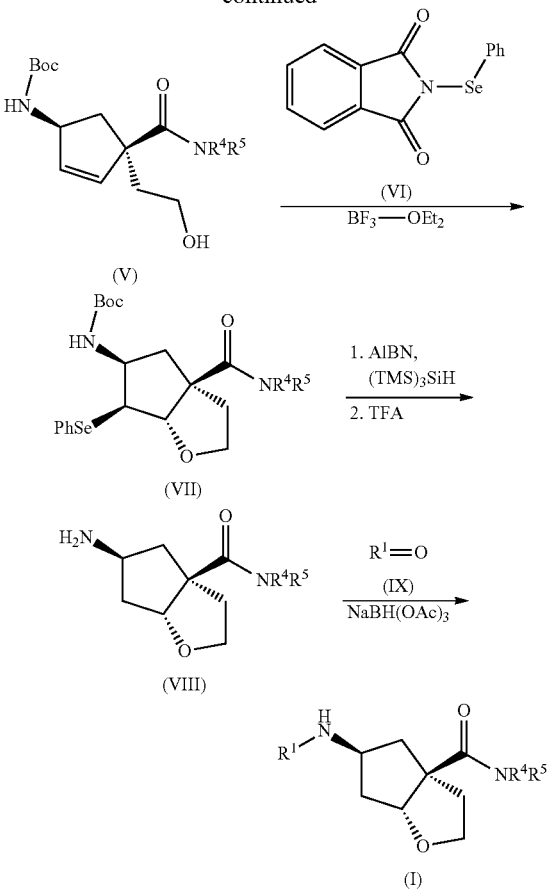

Scheme 1 illustrates a synthetic route leading to compounds of Formula (I) wherein $R^0$, $R^2$ and $R^3$ are each hydrogen. Commercially available esters of formula (II) is alkylated by reacting with a suitable selected base such as LiHMDS, and the like; and then reacted with t-butyl(2-iodoethoxy)dimethylsilane, in an organic solvent such as THF or diethyl ether, at a temperature in the range of −78° C. to 20° C. The resulting alkylated ester is then saponified by reacting with an aqueous base such as NaOH, KOH, or LiOH, in a solvent such as methanol or ethanol, at a temperature in the range of 0° C. to 60° C., to yield the corresponding acid, a compound of formula (III).

The acid of formula (III) is then reacted with a suitably selected, commercially available amine of formula (IV), in the presence of a coupling reagent such as EDCI/HOBt, PyBrop or DCC, in an organic solvent such as THF, dichloromethane or 1,2-dichloroethane, at a temperature in the range of about 0° C. to about 25° C., to yield the corresponding amide; which is then reacted to de-protect the alcohol functionality, by reacting with a fluoride source such as TBAF, in a solvent such as THF, at a temperature range of about 0° C. to 60° C., to yield the corresponding, desilylated alcohol of formula (V).

The alcohol of formula (V) is reacted with a reagent such as N-(phenylseleno)phthalimide (VI) or phenylselenyl chloride, and a Lewis Acid such as borontrifluoride etherate, in a solvent such as DCM or 1,2-dichloroethane, at a temperature of 0° C. to 50° C., to yield the corresponding cyclic ether of formula (VII).

The cyclic ether (VII) is reacted with a suitably selected reducing agent such as tri-n-butylstannane or tris(trimethylsilyl)silane, in the presence of a radical initiator such as AIBN, in a solvent such as benzene or toluene, at a temperature of 60° C. to 120° C.; and the resulting intermediate, de-protected at the N-Boc carbamate by reacting with an acid such as TFA or HCl, in a solvent such as DCM, acetonitrile, THF, or dioxane, at a temperature of 0° C. to 80° C., to yield the corresponding amine of formula (VIII).

The amine of formula (VIII) is reacted with a suitably substituted ketone of formula (IX), in the presence of a suitably selected reducing reagent such as $NaBH_4$, $NaBH_3CN$ or $NaBH(OAc)_3$, in an organic base such as triethylamine, diisopropylethylamine or N-methylmorpholine, with or without molecule sieves, in an organic solvent such as dichloromethane, 1,2-dichloroethane or THF, at a temperature in the range of 0° C. to about 25° C., to yield the corresponding compound of formula (I) wherein $R^0$, $R^2$ and $R^3$ are each hydrogen.

Those skilled in the art will recognize that compounds of formula (I) where $R_0$ is not H may be synthesized from compounds of formula (I) where $R_0$ is H, by standard alkylation procedures. Such alkylation procedures include, but are not limited to, reductive alkylation. For example, a compound of formula (I) where $R_0$ is H may be dissolved in a solvent, such as THF, and reacted with an aldehyde and a reductant, such as sodium triacetoxyborohydride. Suitable temperatures include a range extending from about 25° C. to 50° C.

Compounds of Formula (X) may be prepared according to the processes outlined in Scheme 2.

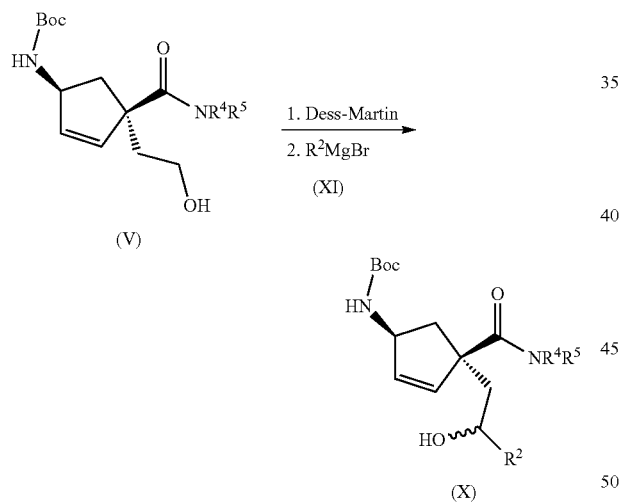

An alcohol of formula (V), prepared for example, as described in Scheme 1 above, is converted to the corresponding aldehyde by reacting with a suitably selected oxidant such as Dess-Martin periodinane, Swern, or pyridinium chlorochromate, in a solvent such as DCM or 1,2-dichloroethane, at a temperature of 0° C. to 50° C. The resulting intermediate is then reacted with a suitably selected Grignard reagent or lithium reagent of formula (XI), in a solvent such as diethyl ether, THF, or toluene, at a temperature of −78° C. to 25° C., to yield the corresponding alcohol of formula (X).

Compounds of Formula (I) wherein A is O and wherein $R^2$ is other than hydrogen may be prepared from the corresponding compound of Formula (X), by substituting said compound of formula (X) for the compound of formula (V) in Scheme 1, above.

Compounds of Formula (XII) may be prepared according to the processes outlined in Scheme 3.

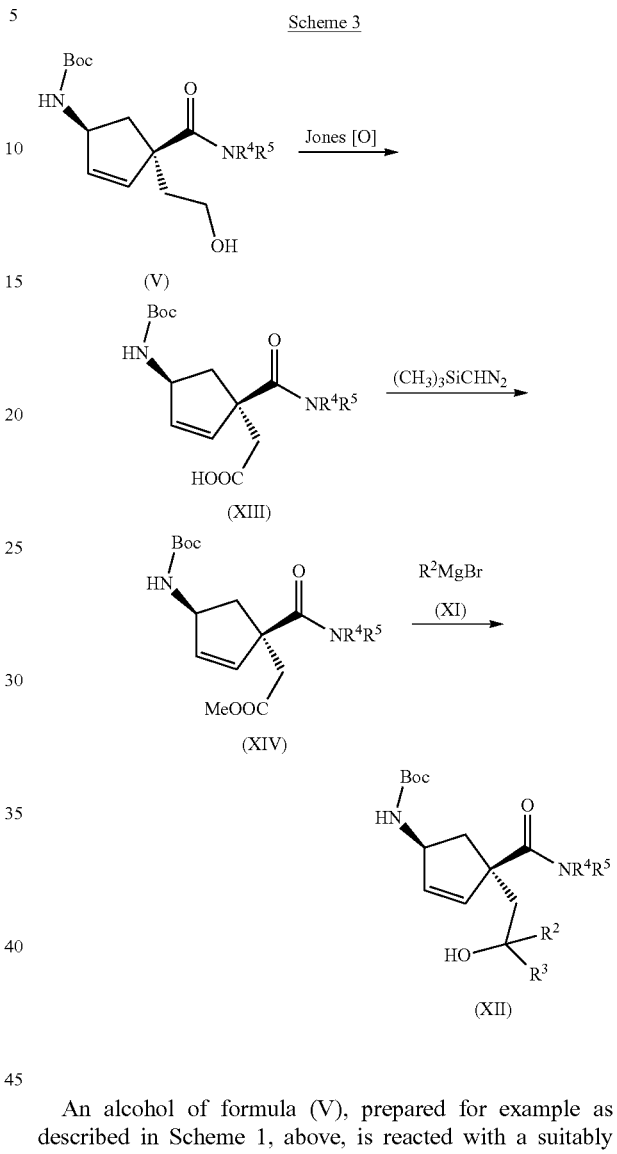

An alcohol of formula (V), prepared for example as described in Scheme 1, above, is reacted with a suitably selected oxidant such as $CrO_3$, $Ru/NaIO_4$, or $KMnO_4$, in a solvent such as acetone or water, at a temperature of 0° C. to 50° C., to yield the corresponding carboxylic acid of formula (XIII).

The acid of formula (XIII) is reacted with a suitably selected alkylating agent such as trimethylsilyl(diazomethane) in a solvent such as methanol or ethanol, at a temperature of −20° C. to 25° C., to yield the corresponding methyl ester of formula (XIV).

The methyl ester of formula (XIV) is reacted with a lithium or Grignard reagent (XI) in a solvent such as diethyl ether, THF, or toluene, at a temperature of −78° C. to 25° C., to yield the substituted alcohol (XII).

Compounds of Formula (I) wherein A is O and wherein $R^2$ and $R^3$ are other than hydrogen may be prepared from the corresponding compound of Formula (XII), by substituting said compound of formula (XII) for the compound of formula (V) in Scheme 1, above.

Compounds of Formula (XV) may be prepared according to the processes outlined in Scheme 4.

Scheme 4

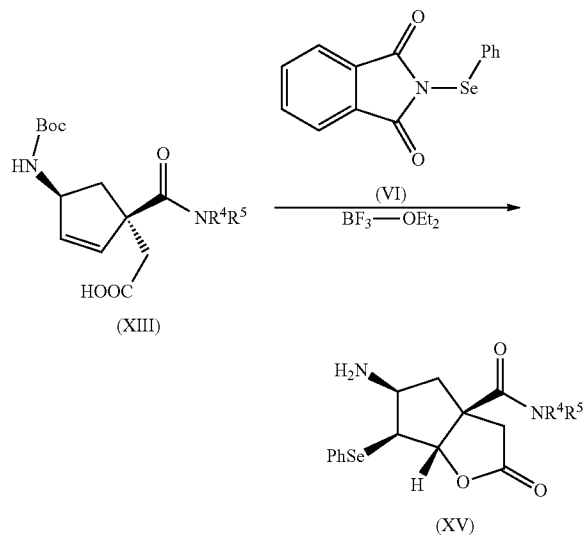

A suitably selected acid of formula (XIII), prepared for example as described in Scheme 3 above, is reacted with a reagent such as N-(phenylseleno)phthalimide (VI) or phenylselenyl chloride, and a Lewis Acid such as borontrifluoride etherate, in a solvent such as DCM or 1,2-dichloroethane, at a temperature of 0° C. to 50° C., to yield the corresponding bicyclic lactone of formula (XV).

Compounds of Formula (I) wherein A is O and wherein $R^2$ and $R^3$ are taken together with the carbon atom to which they are bound to form C=O may be prepared from the corresponding compound of Formula (XV) by substituting said compound of formula (XV) for the compound of formula (V) in Scheme 1, above.

Compounds of Formula (XVI) may be prepared according to the processes outlined in Scheme 5.

Scheme 5

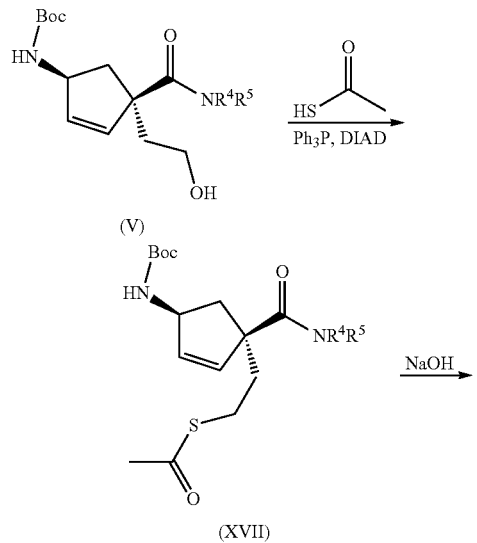

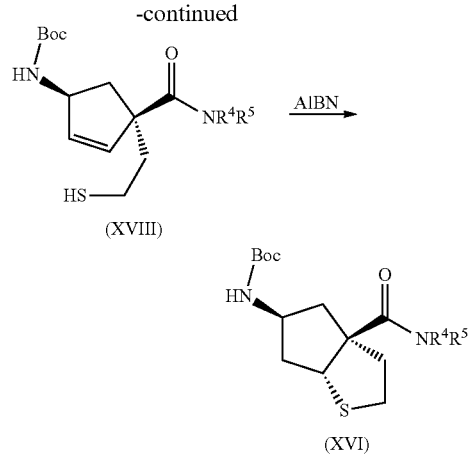

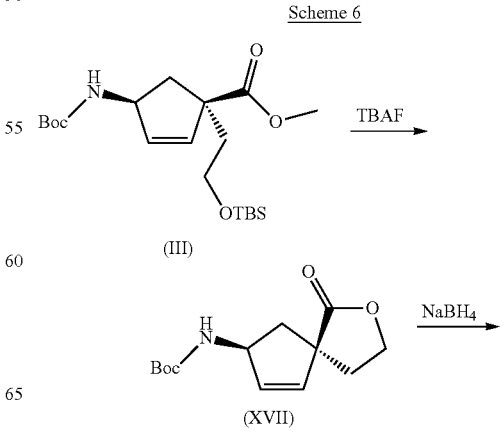

An alcohol of formula (V), prepared for example as described in Scheme 1, above, is reacted with a thioacid such as thioacetic acid, in the presence of a phosphine such as triphenylphosphine or tributylphosphine and in the presence of an activating agent such as diisopropylazodicarboxylate (DIAD) or diethylazodicarboxylate (DEAD), in a solvent such as THF, diethyl ether, DCM or 1,2-dichloroethane, at a temperature of 0° C. to 60° C. (i.e. under Mitsunobu conditions), to yield the corresponding thioester of formula (XVII).

The thioester of formula (XVII) is reacted with an aqueous base such as NaOH, LiOH or KOH, in a solvent such as methanol or ethanol, at a temperature of 0° C. to 60° C., to yield the corresponding thiol of formula (XVIII).

The thiol of formula (XVIII) is reacted with a radical initiator such as AIBN, in a solvent such as benzene or toluene, at a temperature of 60° C. to 120° C., to yield the corresponding bicyclic thioether of formula (XVI).

Compounds of formula (I) wherein A is S, $R^0$ is hydrogen, and wherein $R_2$ and $R_3$ are other than hydrogen may be prepared according to the procedures of Scheme 5, by starting with compound (XII) (as prepared in Scheme 3) in place of compound (V). Additionally, reductive alkylation as described in Scheme 1 can be employed by one of ordinary skill in the art as a means for transforming these compounds of formula (I) where A is S and $R_0$ is H to compounds of formula (I) where A is S and $R_0$ is other than H.

Compounds of Formula (VIII) may alternatively be prepared according to the procedure of Scheme 6.

Scheme 6

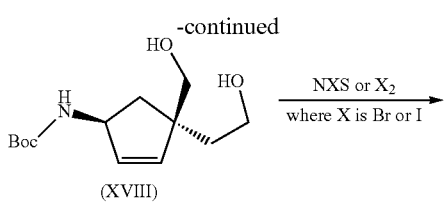

(XVIII)

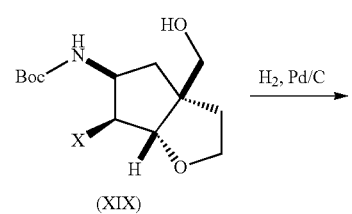

(XIX)

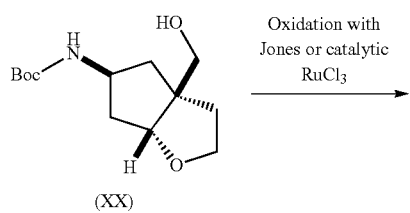

(XX)

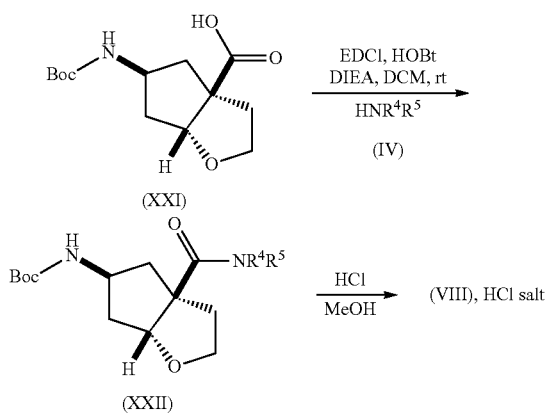

A compound of formula (III), prepared for example as described in Scheme 1 above, is cyclized by reacting with a suitably selected de-silylating agent, such as tetra-butyl ammonium fluoride, and the like, in a solvent such as THF, and the like, at a temperature range from about −20° C. to about 50° C. to yield the corresponding lactone of formula (XVII).

The lactone of formula (XVII) is reacted with a suitably selected reducing agent, such as $NaBH_4$, $LiAlH_4$, and the like, in a suitably selected solvent, such as THF, and the like, at a temperature range of from about −20° C. to about 50° C., to yield the corresponding diol of formula (XVIII).

The diol of formula (XVIII) is reacted with a suitably selected halogenating reagent such as N-bromo-succinimide, N-iodo-succinimide, $Br_2$, and the like, in a solvent such as THF, EtOAc, $CH_2Cl_2$, and the like, at a temperature range of from about 0° C. to about 100° C., to yield the corresponding intermediate of formula (XIX).

The intermediate of formula (XIX) is hydrogenated by reacted with hydrogen gas, in a solvent or mixture of solvents, such as THF, EtOAc, methanol, and the like, in the presence of a suitably selected catalyst such as Pd/C, Pt/C, and the like, at about room temperature, to yield the corresponding alcohol of formula (XX).

Alternatively, the intermediate of formula (XIX) may be reacted with a reducing agent such as tri-n-butylstannane, tris(trimethylsilyl)silane, and the like, in the presence of a radical initiator such as AIBN, and the like, in a solvent such as benzene, toluene, and the like, at a temperature in the range of from about 60° C. to about 120° C. to yield the corresponding alcohol of formula (XX).

The alcohol of formula (XX) is reacted with a suitably selected oxidant such as $CrO_3$, $Ru/NaIO_4$, $KMnO_4$ and the like, in a solvent such as acetone, water, and the like, at a temperature in the range of from about 0° C. to about 50° C., to yield the corresponding carboxylic acid of formula (XXI).

The carboxylic acid of formula (XXI) is reacted with a suitably selected amine of formula (IV), in the presence of a coupling reagent such as EDCI/HOBt, PyBrop, DCC, and the like, in an organic solvent such as THF, dichloromethane, 1,2-dichloroethane, and the like, at a temperature in the range of about 0° C. to about 25° C., to yield the corresponding amide of formula (XXII).

The amide of formula (XXII) is de-protected by reacting under acidic conditions, such as HCl in MeOH, at temperature ranging from about 25° C. to about 80° C., to yield the corresponding compound of formula (VIII), which may then be reacted, as described in Scheme 1 above, to yield the corresponding compound of Formula (I) wherein A is O, and wherein $R_0$, $R_2$ and $R_3$ are each hydrogen.

Alternatively, the compound of formula (XVIII) may be reacted with N-(phenylseleno)phthalimide (VI) or phenylselenyl chloride, in the presence of a suitably selected a Lewis Acid such as borontrifluoride etherate, and the like, in a solvent such as DCM, 1,2-dichloroethane, and the like, at a temperature in the range of form about 0° C. to about 50° C., to yield the corresponding cyclic ether of formula (XIX), where X is Ph-Se.

The cyclic ether of formula (XIX) is then reacted with a suitably selected reducing agent such as tri-n-butylstannane, tris(trimethylsilyl)silane, and the like, in the presence of a radical initiator such as AIBN, and the like, in a solvent such as benzene, toluene, and the like, at a temperature in the range of from about 60° C. to about 120° C. to yield the corresponding intermediate of formula (XX).

The intermediate of formula (XX) is then reacted as described above, to yield the corresponding compound of formula (I) wherein A is O, and wherein $R_0$, $R_2$ and $R_3$ are each hydrogen.

Additionally, reductive alkylation as described in Scheme 1 can be employed by one of ordinary skill in the art as a means for transforming these compounds of formula (I) where A is O and $R_0$ is H to compounds of formula (I) where A is O and $R_0$ is other than H.

EXAMPLES

Representative compounds of the present invention can be synthesized in accordance with the general synthetic methods described below. Compounds of Formula (I) can be prepared by methods known to those who are skilled in the art. The The following examples are only meant to represent examples of the invention and are in no way meant to be a limit of the invention.

Intermediate 1

(R)-3-methoxydihydro-2H-pyran-4(3H)-one

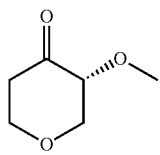

Step A 4,4-Dimethoxytetrahydro-2H-pyran-3-ol

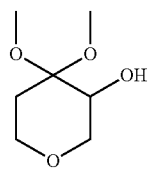

A 12-L 4-neck round bottom flask with an overhead stirrer was charged with MeOH (8.18 L) and potassium hydroxide (400.5 g, 2.4 mol) while stirring at room temperature until base was completely dissolved (an exotherm was observed). The homogeneous mixture was cooled to 0° C. with an ice-acetone bath. To a 500-mL addition funnel was charged with tetrahydro-4H-pyran-4-one (250 g, 2.5 mol) and after the KOH-methanol solution temperature reached 0° C., the pyra-none was added drop wise while maintaining temperature at <5° C. After stirring for an additional 1.5 h, iodine (704 g, 1.1 mol) was added portion wise over a 1.5 h period while maintaining the temperature at <5° C. The reaction mixture was allowed to stir at room temperature for 18 h. The reaction was concentrated and the remaining residue was treated with toluene (1.5 L) and stirred for ½ h. A solid had precipitated, was filtered off and the filtrate was evaporated to afford to afford the title compound (330 g, 81%) as an amber oil.

Step B 4,4-Dimethoxydihydro-2H-pyran-3(4H)-one

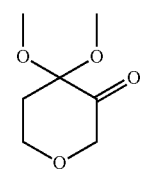

A 12-L 4-neck Morton flask equipped with an overhead stirrer, thermocouple, and two addition funnels was charged with oxalyl chloride (130 mL, 1.49 mol) and CH$_2$Cl$_2$ (2.5 L). The solution was chilled with dry-ice/acetone bath to −72° C. DMSO (178 mL, 2.50 mol) was added via additional funnel in CH$_2$Cl$_2$ (530 mL) over ½ h period while maintaining temperature at or below −70° C. After the addition was complete, the mixture was stirred for an additional 30 min and 4,4-dimethoxytetrahydro-2H-pyran-3-ol (as prepared in Step A, 200 g, 1.23 mol) in CH$_2$Cl$_2$ (630 mL) was added slowly (~½ h) from an addition funnel keeping the temperature at or below −70° C. After stirring an additional 30 min, Et$_3$N (870 mL, 6.24 mol) was added, the temperature reached −42° C. and dropped back down to approx. −70° C. The stirred mixture was allowed to stir to room temperature over 18 h. The mixture was filtered and the filtrate was concentrated to provide the crude product plus Et$_3$N—HCl solid. The mixture was filtered and rinsed with EtOAc (2×500 mL). The filtrate was concentrated again to a slurry. The slurry was diluted with EtOAc (approx 1 L), filtered, and concentrated again to give an amber oil containing the product and residual DMSO as the primary components. After purification on silica gel using a mixture of ethyl acetate in heptanes, the title compound (285 g, 90%) was afforded as a brown solid.

Step C1

(R)-4,4-dimethoxytetrahydro-2H-pyran-3-ol

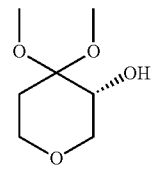

A 12-L 4-neck round bottom flask equipped with a overhead air stirrer, addition funnel with nitrogen inlet adapter, condenser, and thermocouple was charged with S-(−)-2-methyl-CBS-oxazaborolidine (40 g, 0.12 mol) and THF (2.2 L). The mixture was warmed under nitrogen to 40° C. then Me$_2$S—BH$_3$ (108 mL, 1.15 mol) was added to the THF-catalyst mixture via syringe. An addition funnel charged with 4,4-dimethoxydihydro-2H-pyran-3(4H)-one (as prepared in the previous step, 165 g, 0.59 mol) in THF (2.1 L) was added drop wise over a 7 h period. After the addition was complete, the reaction was allowed to stir for 18 h at 40° C. The reaction was chilled to 10° C. in an ice-acetone bath and quenched by slow addition of MeOH (1.1 L) over 1 h period. The cooling bath was removed and the mixture allowed to warm to room temperature for 3 h. After the gas evolution ceased, the mixture was concentrated on a rotary evaporator to give 188 g. Purification on silica gel using a mixture of EtOAc and heptanes afforded the title compound (166 g, 99%, chiral GC 93% ee) as a yellow oil.

Step C

Alternative (R)-4,4-Dimethoxytetrahydro-2H-pyran-3-ol

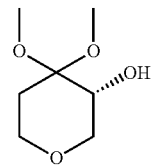

A 12-L 4-neck round bottom flask equipped with a overhead air stirrer, addition funnel with nitrogen inlet adapter, condenser, and thermocouple was charged with S-(−)-2-methyl-CBS-oxazaborolidine (78 g, 0.28 mol) and THF (2.7 L). The mixture was warmed under nitrogen to 40° C. while borane-N,N-diethylaniline complex (280 mL, 1.57 mol) was added to the THF-catalyst mixture via addition funnel over 40 min. An 4-L Erlenmeyer flask was charged with a mixture of 4,4-dimethoxydihydro-2H-pyran-3(4H)-one (as prepared in Step B, 225 g, 1.4 mol) in THF (2.7 L) and was added drop wise over a 8 h period via metering pump. After addition, the reaction was allowed to stir for 18 h at 40° C. The reaction was chilled to 10° C. in an ice-acetone bath and quenched by slow addition of MeOH (1.35 L) over 1 h period; after MeOH addition was complete, the cooling bath was removed and the mixture allowed to warm to room temperature for 3 h. After the gas evolution ceased, the mixture was concentrated on a rotary evaporator to give 365 g. After purification on silica gel using a mixture of EtOAc in heptanes the title compound (157 g, 69%, chiral GC 95.5% ee) was afforded as a yellow oil.

Step D (R)-3,4,4-Trimethoxytetrahydro-2H-pyran

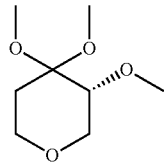

A 12-L 4-neck round bottom flask equipped with a overhead air stirrer, addition funnel with nitrogen inlet adapter, condenser, and thermocouple was charged with (R)-4,4-dimethoxytetrahydro-2H-pyran-3-ol (as prepared in the previous step, 163 g, 1.0 mol) in THF (2.4 L) and stirred in ice/acetone bath until <0° C. KOtBu (113 g, 1.0 mol) was added in one portion, and after stirring 45 min, dimethyl sulfate (95 mL, 1.0 mol) was added via addition funnel over 15 min. The reaction was allowed to stir at room temperature for 2 h. The reaction mixture was poured into a reparatory flask containing H₂O (1.2 L) and CH₂Cl₂ (1.2 L) and the layers were separated. The aqueous layer was back-extracted with CH₂Cl₂ (900 mL). The combined organic layers were washed with brine (1.0 L; Note: organic layer was on top), dried over MgSO₄, filtered and evaporated to afford the title compound (177.1 g, 99%, chiral GC 94.4% ee) as a light yellow oil.

Step E (R)-3-methoxydihydro-2H-pyran-4(3H)-one

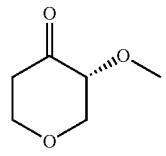

A stirred mixture of (R)-3,4,4-trimethoxytetrahydro-2H-pyran (as prepared in the previous step, 141 g, 0.80 mol), in THF (3.6 L) and H₂O (1.1 L) in an ice/acetone bath at <0° C., was treated with a solution of HCl (conc., 595 mL, 7.21 mol) added via addition funnel over 45 min while keeping temperature <3° C. After the addition was complete, the reaction was allowed to stir for 1.5 h at 0° C. The reaction was evaporated until ~1.9 L of concentrate remained. The concentrated was transferred to a separatory funnel and extracted with CH₂Cl₂ (3×1 L). The combined organic fractions were washed with sat. NaHCO₃ (1 L), brine (1 L), dried over MgSO₄, filtered and evaporated to afford the title compound (71.4 g, 69%, Chiral GC 92% ee) as an oil which solidified upon standing. Optical Rotation: [α]²⁵(D)-6.97° (c=0.8222, MeOH); Elemental Analysis calc for $C_6H_{10}O_3$: C, 53.59; H, 7.58. Found: C, 53.64; H, 7.65.

Intermediate 2

(S)-3-methoxydihydro-2H-pyran-4(3H)-one

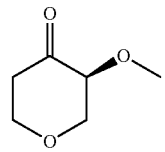

Step A (S)-4,4-dimethoxytetrahydro-2H-pyran-3-ol

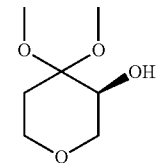

A 5-L 4-neck round bottom flask equipped with an overhead air stirrer, addition funnel with nitrogen inlet adapter, condenser, and a thermocouple was charged with (R)-(+)-2-methyl-CBS-oxazaborolidine (34 g, 0.12 mol) and THF (1.2 L). The mixture was warmed under nitrogen to 40° C. then Me₂S—BH₃ (63 mL, 0.67 mol) was added to the THF-catalyst mixture via syringe. An addition funnel was charged with 4,4-dimethoxydihydro-2H-pyran-3(4H)-one (as prepared in Intermediate 1, Step B, 96 g, 0.59 mol) in THF (1.2 L) was added drop wise over an 8 h period. After addition, the reaction was allowed to stir for 18 h at 40° C. The reaction was chilled to 10° C. in an ice-acetone bath and quenched by slow addition of MeOH (600 mL) over 45 min. The cooling bath was removed and the mixture allowed to warm to room temperature for 3 h. After the gas evolution ceased, the mixture was concentrated on a rotary evaporator to give 132 g. Purification on silica gel using a mixture of EtOAc and heptanes afforded the title compound (80.5 g, 83%, chiral GC 95% ee) as a yellow oil.

Step A

Alternative 1

(S)-4,4-dimethoxytetrahydro-2H-pyran-3-ol

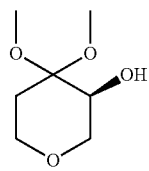

The reaction was carried out according to the procedure of Intermediate 2, Step A, using 0.1 equivalents of (R)-(+)-2-methyl-CBS-oxazaborolidine, and substituting BH$_3$-THF complex for Me$_2$S—BH$_3$. The product (S)-4,4-dimethoxytetrahydro-2H-pyran-3-ol was obtained in 88% yield and 60% ee.

Step A

Alternative 2

(S)-4,4-dimethoxytetrahydro-2H-pyran-3-ol

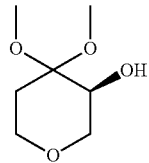

The reaction was carried out according to the procedure of Intermediate 2, Step A, using 0.1 equivalents of (R)-(+)-2-methyl-CBS-oxazaborolidine, and substituting catecholborane for Me$_2$S—BH$_3$. The product (S)-4,4-dimethoxytetrahydro-2H-pyran-3-ol was obtained in <20% yield and 60% ee.

Step B (S)-3,4,4-trimethoxytetrahydro-2H-pyran

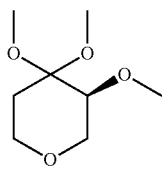

A 3-L 4-neck round bottom flask equipped with a overhead air stirrer, addition funnel with nitrogen inlet adapter, condenser, and thermocouple was charged with (S)-4,4-dimethoxytetrahydro-2H-pyran-3-ol (as prepared in the previous step, 80 g, 0.49 mol) in THF (1.1 L) and stirred in ice/acetone bath until <0° C. KOtBu (56 g, 0.49 mol) was added in one portion, and after stirring 45 min, dimethyl sulfate (47 mL, 0.49 mol) was added via addition funnel over 15 min. The reaction was allowed to stir at room temperature for 3 h. The reaction mixture was poured into a separatory flask containing H$_2$O (1.25 L) and CH$_2$Cl$_2$ (1.25 L) and the layers were separated. The aqueous layer was back-extracted with CH$_2$Cl$_2$ (750 mL). The combined organic layers were washed with brine (1 L; Note: organic layer was on top), dried over MgSO$_4$, filtered and evaporated to afford the title compound (83.5 g, 96%, chiral GC 94.6% ee) as a light yellow oil.

Step C (S)-3-methoxydihydro-2H-pyran-4(3H)-one

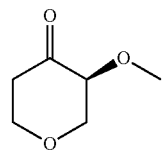

A 5-L 4-neck round bottom flask equipped with a overhead air stirrer, nitrogen inlet adapter, thermocouple, and septum was charged with (S)-3,4,4-trimethoxytetrahydro-2H-pyran (as prepared in the previous step, 83 g, 0.47 mol), THF (2.1 L), H$_2$O (670 mL), and stirred in ice/acetone bath until <0° C., where upon a solution of HCl (conc., 350 mL, 4.24 mol) was added via addition funnel over 30 min while keeping temperature <2° C. After the addition was complete, the reaction was allowed to stir for 1 h at 0° C. The reaction was evaporated until ~1.2 L of concentrate remained. The concentrate was transferred to a reparatory funnel and extracted with CH$_2$Cl$_2$ (3×750 mL). The combined organic fractions were washed with sat. NaHCO$_3$ (500 mL), brine (500 mL), dried over MgSO$_4$, filtered and evaporated to afford the title compound (46.9 g, 77%, Chiral GC 91% ee) as an oil which solidified upon sitting. Optical Rotation: $[\alpha]^{25}$(D)+3.65° (c=1.020, MeOH); Elemental Analysis calc for C$_6$H$_{10}$O$_3$: C, 53.39; H, 7.57. Found: 53.59; H, 7.62.

Example 1

((3aS,5S,6aR)-5-((3-methoxytetrahydro-2H-pyran-4-yl)amino)hexahydro-2H-cyclopenta[b]furan-3a-yl) (3-(trifluoromethyl)-7,8-dihydro-1,6-naphthyridin-6 (5H)-yl)methanone

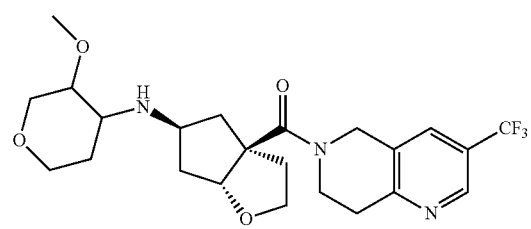 [SMILES: COC1COCCC1N[C@@H]1C[C@H]2OCC[C@@]2(C(=O)N2CCc3ncc(C(F)(F)F)cc3C2)C1]

Step A (1S,4S)-methyl 4-((tert-butoxycarbonyl)amino)-1-(2-((tert-butyldimethylsilyl)oxy)ethyl)cyclopent-2-enecarboxylate

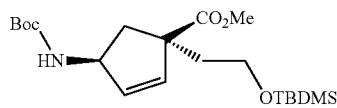

To a solution of LiHMDS in THF (72.9 mL of a 1 M solution, 72.9 mmol, 2.2 eq) at −78° C. under Ar was added a solution of (1R,4S)-methyl 4-((t-butoxycarbonyl)amino)cyclopent-2-enecarboxylate (prepared according to the procedure of US 20050101628 A1 (see page 31, column 1, Procedure B, step B)), 8.00 g, 33.2 mmol, 1 eq) in THF (40 mL) dropwise over 1 hr. After stirring for 30 min, a solution of t-butyl(2-iodoethoxy)dimethylsilane (13.29 g, 46.4 mmol, 1.4 eq) in THF (20 mL) was added. The solution was kept at −78° C. for 15 min, then gradually warmed to 0° C. over 2 hrs, and kept at 0° C. for 1 hr. 1 N HCl and water were added, the solution extracted with DCM, the organics combined, dried over MgSO$_4$, and concentrated. Purification by chromatography (400 g column) eluting with 5 to 20% EtOAc/heptane afforded the title compound of Step A. $^1$H NMR (CHLOROFORM-d) δ: 5.76-5.85 (m, 2H), 4.90 (d, J=9.0 Hz, 1H), 4.72-4.82 (m, 1H), 3.69 (s, 3H), 3.57-3.64 (m, 2H), 2.24 (dd, J=13.9, 8.0 Hz, 1H), 2.14 (dd, J=14.1, 3.5 Hz, 2H), 1.71-1.82 (m, 1H), 1.40-1.50 (m, 9H), 0.84-0.90 (m, 9H), 0.03 (s, 6H). ESI-MS (m/z): Calculated for C20H37NO5Si: 422.2 (M+23). found: 422.2.

Step B (1S,4S)-4-((tert-butoxycarbonyl)amino)-1-(2-((tert-butyldimethylsilyl)oxy)ethyl)cyclopent-2-enecarboxylic acid

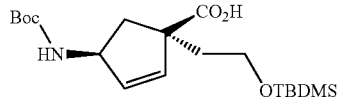

To a solution of the product of Step A (7.89 g, 19.74 mmol, 1 eq) in methanol (100 mL) at rt was added 1 N NaOH (59.2 mL, 59.2 mmol, 3.0 eq). After stirring overnight, the methanol was removed, 1 N HCl was added until the solution was acidic, the solution extracted with DCM, the organics combined, dried over MgSO$_4$, and concentrated to afford the title compound of Step B. $^1$H NMR (CHLOROFORM-d) δ: 5.85 (br. s., 2H), 4.97 (br. s., 1H), 4.80 (br. s., 1H), 3.71 (br. s., 2H), 1.99-2.41 (m, 3H), 1.92 (br. s., 1H), 1.44 (br. s., 9H), 0.88 (s, 9H), 0.06 (br. s., 6H). ESI-MS (m/z): Calculated for C19H35NO5Si: 408.2 (M+23). found: 408.3.

Step C tert-butyl ((1S,4S)-4-(2-((tert-butyldimethylsilyl)oxy)ethyl)-4-(3-(trifluoromethyl)-5,6,7,8-tetrahydro-1,6-naphthyridine-6-carbonyl)cyclopent-2-en-1-yl) carbamate

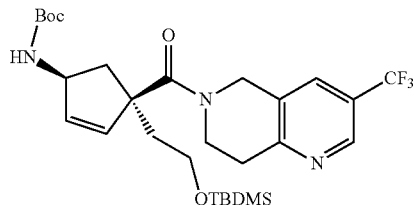 [SMILES: CC(C)(C)OC(=O)N[C@@H]1C=C[C@](CCO[Si](C)(C)C(C)(C)C)(C(=O)N2CCc3ncc(C(F)(F)F)cc3C2)C1]

To a solution of the product of Step B (3.47 g, 8.99 mmol, 1 eq) in DCM (40 mL) at rt was added HOBt hydrate (2.34 g, 15.3 mmol, 1.7 eq) and EDCI (2.58 g, 13.5 mmol, 1.5 eq). After 15 min, DIEA (7.8 mL, 45.3 mmol, 5 eq) and 3-(trifluoromethyl)-5,6,7,8-tetrahydro-1,6-naphthyridine-2HCl (3.71 g, 13.5 mmol, 1 eq) were added and the solution stirred overnight at rt. Saturated NaHCO$_3$ was added, the solution extracted with DCM, the organics combined, dried over MgSO$_4$, and concentrated. Purification by chromatography (120 g column) eluting with 25 to 60% EtOAc/heptane afforded the title compound of Step C. $^1$H NMR (CHLOROFORM-d) δ: 8.71 (s, 1H), 7.69 (s, 1H), 6.19 (d, J=5.4 Hz, 1H), 5.76 (dd, J=5.6, 2.0 Hz, 1H), 4.68-4.86 (m, 4H), 3.85-4.07 (m, 2H), 3.54-3.65 (m, 2H), 3.13 (t, J=5.7 Hz, 2H), 2.58 (dd, J=13.3, 7.7 Hz, 1H), 1.98-2.16 (m, 2H), 1.85-1.97 (m, 1H), 1.42 (s, 9H), 0.84 (s, 9H), −0.02 (d, J=4.4 Hz, 6H). Calculated for C28H42F3N3O4Si: 570.3 (M+1). found: 570.3.

Step D tert-butyl ((1S,4S)-4-(2-hydroxyethyl)-4-(3-(trifluoromethyl)-5,6,7,8-tetrahydro-1,6-naphthyridine-6-carbonyl)cyclopent-2-en-1-yl)carbamate

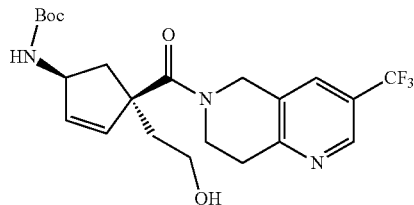 [SMILES: CC(C)(C)OC(=O)N[C@@H]1C=C[C@](CCO)(C(=O)N2CCc3ncc(C(F)(F)F)cc3C2)C1]

To a solution of the product of Step C (3.52 g, 6.18 mmol, 1 eq) in THF (50 mL) at rt was added TBAF in THF (12.36 mL of a 1 M solution, 12.36 mmol, 2 eq). After 1 hr, water was added, the solution extracted with DCM, the organics combined, dried over MgSO$_4$, and concentrated. Purification by chromatography (80 g column) eluting with 2 to 6% methanol/DCM with ammonia afforded the title compound of Step D. $^1$H NMR (CHLOROFORM-d) δ: 8.71 (s, 1H), 7.70 (s, 1H), 6.28 (dd, J=5.9, 2.0 Hz, 1H), 5.78 (dd, J=5.9, 2.0 Hz, 1H), 4.70-4.95 (m, 4H), 3.99-4.10 (m, 1H), 3.85-3.96 (m, 1H), 3.68 (br. s., 2H), 3.09-3.18 (m, 2H), 2.65 (dd, J=12.9, 7.4

Hz, 1H), 1.99-2.21 (m, 3H), 1.82-1.93 (m, 1H), 1.38-1.49 (m, 9H). Calculated for C22H28F3N3O4: 456.2 (M+1). found: 456.2.

Step E tert-butyl ((3aS,5S,6S,6aS)-6-(phenylselanyl)-3a-(3-(trifluoromethyl)-5,6,7,8-tetrahydro-1,6-naphthyridine-6-carbonyl)hexahydro-2H-cyclopenta[b]furan-5-yl)carbamate

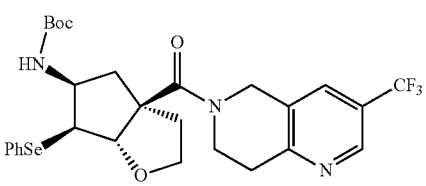

To a solution of the product of Step D (1.51 g, 3.32 mmol, 1 eq) in DCM (40 mL) at rt under Ar was added N-(phenylseleno)phthalimide (1.60 g, 4.97 mmol, 1.5 eq) and BF3-etherate (0.042 mL, 0.33 mmol, 0.1 eq). After 2 hrs, 1 N NaOH was added and stirred 5 min., water was added, the solution extracted with DCM, the organics combined, dried over MgSO4, and concentrated. Purification by chromatography (80 g column) eluting with 50 to 100% EtOAc/heptane afforded the title compound of Step E. ¹H NMR (CHLOROFORM-d) δ: 8.72 (s, 1H), 7.69 (s, 1H), 7.50-7.62 (m, 2H), 7.22-7.27 (m, 3H), 5.35 (s, 1H), 5.06 (d, J=8.1 Hz, 1H), 4.79-5.01 (m, 1H), 4.66-4.78 (m, 1H), 4.53 (br. s., 1H), 3.78-4.06 (m, 4H), 3.68-3.78 (m, 1H), 3.05-3.19 (m, 2H), 2.32 (dd, J=11.6, 5.8 Hz, 2H), 2.16 (d, J=10.9 Hz, 2H), 1.36 (s, 9H). Calculated for C28H32F3N3O4Se: 634.2 (M+23). found: 634.1.

Step F tert-butyl ((3aS,5S,6aR)-3a-(3-(trifluoromethyl)-5,6,7,8-tetrahydro-1,6-naphthyridine-6-carbonyl)hexahydro-2H-cyclopenta[b]furan-5-yl)carbamate

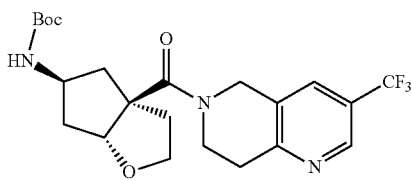

To a solution of the product of Step E (1.51 g, 2.67 mmol, 1 eq), tris(trimethylsilyl)silane (1.72 mL, 5.34 mmol, 2 eq) and AIBN (438 mg, 2.67 mmol, 1 eq) in benzene (20 mL) was warmed to 80° C. under Ar. After 3 hrs, the solution was concentrated. Purification by chromatography (80 g column) eluting with 50 to 100% EtOAc/heptane afforded the title compound of Step F. ¹H NMR (CHLOROFORM-d) δ: 8.72 (br. s., 1H), 7.71 (br. s., 1H), 4.97-5.09 (m, 1H), 4.70-4.91 (m, 2H), 4.56-4.69 (m, 1H), 4.28 (br. s., 1H), 3.80-4.07 (m, 3H), 3.71 (q, J=7.3 Hz, 1H), 3.13 (br. s., 2H), 2.07-2.53 (m, 4H), 1.81 (br. s., 1H), 1.61-1.72 (m, 1H), 1.40 (s, 9H). Calculated for C22H28F3N3O4: 478.2 (M+23). found: 478.2.

Step G ((3aS,5S,6aR)-5-aminohexahydro-2H-cyclopenta[b]furan-3a-yl)(3-(trifluoromethyl)-7,8-dihydro-1,6-naphthyridin-6(5H)-yl)methanone

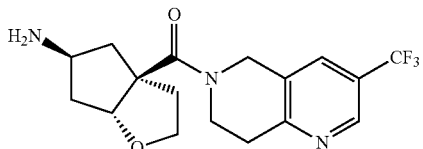

To a solution of the product of Step F (12.54 g, 24.8 mmol, 1 eq) in DCM (100 mL) at rt was added TFA (20 mL, 261 mmol, 10.6 eq). After 1 hr, the solution was concentrated. 3 M NaOH was added and the solution extracted with DCM, the organics combined, dried over MgSO4, and concentrated to afford the title compound of Step G. ¹H NMR (CHLOROFORM-d) δ: 8.72 (s, 1H), 7.69 (br. s., 1H), 5.07 (d, J=4.9 Hz, 1H), 4.71-4.90 (m, 2H), 3.84-4.03 (m, 3H), 3.58-3.71 (m, 2H), 3.09-3.20 (m, 2H), 2.14-2.41 (m, 3H), 1.99-2.13 (m, 1H), 1.65-1.75 (m, 1H), 1.43-1.58 (m, 1H). Calculated for C17H20F3N3O2: 356.2 (M+1). found: 356.3.

Step H ((3aS,5S,6aR)-5-((3-methoxytetrahydro-2H-pyran-4-yl)amino)hexahydro-2H-cyclopenta[b]furan-3a-yl)(3-(trifluoromethyl)-7,8-dihydro-1,6-naphthyridin-6(5H)-yl)methanone

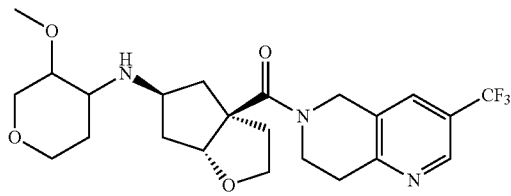 [SMILES: COC1COCCC1N[C@@H]1C[C@H]2OCC[C@@]2(C(=O)N2CCc3ncc(C(F)(F)F)cc3C2)C1]

To a solution of the product of Step G (119 mg, 0.33 mmol, 1 eq) in DCM at rt was added acetic acid (0.01 mL, 0.17 mmol, 0.5 eq), 3-methoxytetrahydro-4H-pyran-4-one (131 mg, 1.0 mmol, 3 eq) and sodium triacetoxyborohydride (355 mg, 1.67 mmol, 5 eq). After stirring overnight, saturated NaHCO3 was added, the solution extracted with DCM, the organics combined, dried over MgSO4, and concentrated. Purification by chromatography (12 g) eluting with 4 to 8% methanol/DCM with ammonia afforded the title compound of Example 1. ¹H NMR (CHLOROFORM-d) δ: 8.72 (br. s., 1H), 7.70 (br. s., 1H), 4.98-5.14 (m, 1H), 4.70-4.89 (m, 2H), 3.80-4.18 (m, 5H), 3.25-3.75 (m, 8H), 3.07-3.24 (m, 2H), 2.53-2.89 (m, 1H), 2.01-2.48 (m, 4H), 1.39-1.88 (m, 5H). Calculated for C23H30F3N3O4: 470.2 (M+1). found: 470.2.

Separation of Example 1 by chiral HPLC gave 4 products, Example 2, Example 3, Example 4 and Example 5.

Example 2

((3aS,5S,6aR)-5-(((3S,4S)-3-methoxytetrahydro-2H-pyran-4-yl)amino)hexahydro-2H-cyclopenta[b]furan-3a-yl)(3-(trifluoromethyl)-7,8-dihydro-1,6-naphthyridin-6(5H)-yl)methanone

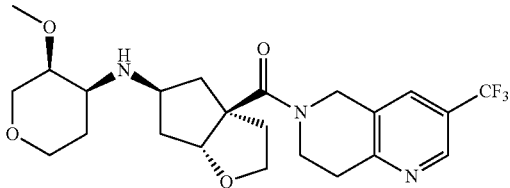 [SMILES: CO[C@@H]1COCC[C@@H]1N[C@@H]1C[C@H]2OCC[C@@]2(C(=O)N2CCc3ncc(C(F)(F)F)cc3C2)C1]

¹H NMR (CHLOROFORM-d) δ: 8.71 (s, 1H), 7.70 (br. s., 1H), 5.05 (d, J=4.6 Hz, 1H), 4.68-4.88 (m, 2H), 4.08 (dd, J=12.5, 2.9 Hz, 1H), 3.81-4.04 (m, 4H), 3.66 (td, J=8.8, 6.8 Hz, 1H), 3.50-3.62 (m, 1H), 3.34-3.46 (m, 4H), 3.24-3.34 (m, 2H), 3.14 (br. s., 2H), 2.76 (d, J=9.5 Hz, 1H), 2.14-2.46 (m, 3H), 1.99-2.14 (m, 1H), 1.45-1.86 (m, 5H). Calculated for C23H30F3N3O4: 470.2 (M+1). found: 470.2.

Example 3

((3aS,5S,6aR)-5-(((3R,4R)-3-methoxytetrahydro-2H-pyran-4-yl)amino)hexahydro-2H-cyclopenta[b]furan-3a-yl)(3-(trifluoromethyl)-7,8-dihydro-1,6-naphthyridin-6(5H)-yl)methanone

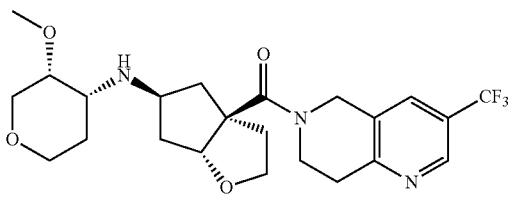 [SMILES: CO[C@H]1COCC[C@H]1N[C@@H]1C[C@H]2OCC[C@@]2(C(=O)N2CCc3ncc(C(F)(F)F)cc3C2)C1]

¹H NMR (CHLOROFORM-d) δ: 8.72 (s, 1H), 7.70 (br. s., 1H), 5.06 (d, J=4.6 Hz, 1H), 4.78 (br. s., 2H), 4.05 (dd, J=12.6, 4.0 Hz, 1H), 3.84-4.02 (m, 4H), 3.65 (td, J=8.9, 7.0 Hz, 1H), 3.55 (dt, J=9.7, 5.0 Hz, 1H), 3.35-3.45 (m, 4H), 3.27-3.35 (m, 2H), 3.14 (br. s., 2H), 2.75-2.85 (m, 1H), 2.35 (br. s., 1H), 2.24 (dd, J=13.0, 5.4 Hz, 2H), 2.00-2.15 (m, 1H), 1.59-1.85 (m, 4H), 1.48 (ddd, J=13.2, 10.8, 4.9 Hz, 1H). Calculated for C23H30F3N3O4: 470.2 (M+1). found: 470.2.

Example 4

((3aS,5S,6aR)-5-(((3S,4R)-3-methoxytetrahydro-2H-pyran-4-yl)amino)hexahydro-2H-cyclopenta[b]furan-3a-yl)(3-(trifluoromethyl)-7,8-dihydro-1,6-naphthyridin-6(5H)-yl)methanone (the relative stereochemistry of the methoxypyran ring is trans, the absolute stereochemistry is unknown but opposite that of Example 5)

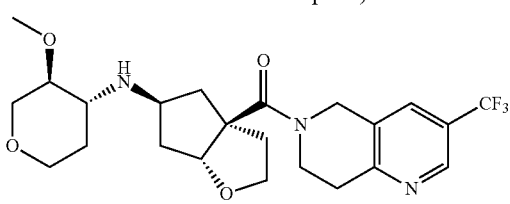

¹H NMR (CHLOROFORM-d) δ: 8.72 (s, 1H), 7.70 (br. s., 1H), 5.01 (d, J=4.6 Hz, 1H), 4.78 (br. s., 2H), 4.04-4.16 (m, 1H), 3.81-4.04 (m, 4H), 3.49-3.70 (m, 2H), 3.27-3.44 (m, 4H), 3.15 (t, J=5.3 Hz, 2H), 2.96-3.09 (m, 2H), 2.59 (br. s., 1H), 2.19-2.44 (m, 3H), 2.00-2.13 (m, 1H), 1.95 (dt, J=13.4, 2.1 Hz, 1H), 1.62-1.87 (m, 2H), 1.57 (ddd, J=13.4, 10.9, 5.0 Hz, 1H), 1.38-1.51 (m, 1H). Calculated for C23H30F3N3O4: 470.2 (M+1). found: 470.2.

Example 5

((3aS,5S,6aR)-5-(((3R,4S)-3-methoxytetrahydro-2H-pyran-4-yl)amino)hexahydro-2H-cyclopenta[b]furan-3a-yl)(3-(trifluoromethyl)-7,8-dihydro-1,6-naphthyridin-6(5H)-yl)methanone (the relative stereochemistry of the methoxypyran ring is trans, the absolute stereochemistry is unknown but opposite that of Example 4)

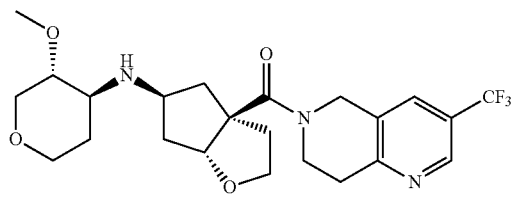 [SMILES: CO[C@H]1COCC[C@@H]1N[C@@H]1C[C@H]2OCC[C@@]2(C(=O)N2CCc3ncc(C(F)(F)F)cc3C2)C1]

¹H NMR (CHLOROFORM-d) δ: 8.72 (s, 1H), 7.69 (br. s., 1H), 5.06 (d, J=4.6 Hz, 1H), 4.67-4.93 (m, 2H), 4.10 (d, J=7.1 Hz, 1H), 3.79-4.04 (m, 4H), 3.48-3.69 (m, 2H), 3.29-3.42 (m, 4H), 3.14 (br. s., 2H), 2.96-3.10 (m, 2H), 2.59-2.72 (m, 1H), 2.21-2.43 (m, 3H), 2.02-2.15 (m, 1H), 1.98 (d, J=24.5 Hz, 1H), 1.57-1.81 (m, 2H), 1.30-1.48 (m, 2H). Calculated for C23H30F3N3O4: 470.2 (M+1). found: 470.2.

Example 6

((3aS,5S,6aR)-5-((tetrahydro-2H-pyran-4-yl)amino)hexahydro-2H-cyclopenta[b]furan-3a-yl)(3-(trifluoromethyl)-7,8-dihydro-1,6-naphthyridin-6(5H)-yl)methanone

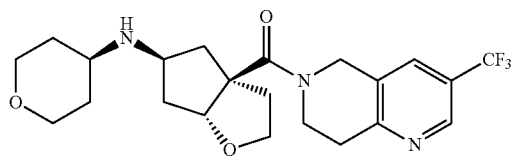

The title compound was prepared from reaction of the product of Example 1, Step G and tetrahydro-4H-pyran-4-one following the procedure described in Example 1, Step H. ¹H NMR (CHLOROFORM-d) δ: 8.72 (br. s., 1H), 7.70 (br. s., 1H), 5.04 (d, J=4.6 Hz, 1H), 4.78 (br. s., 2H), 3.95 (s, 2H), 3.97 (s, 3H), 3.53-3.75 (m, 2H), 3.28-3.49 (m, 2H), 3.14 (br. s., 2H), 2.62-2.81 (m, 1H), 2.29 (dd, J=12.8, 5.5 Hz, 3H), 1.99-2.17 (m, 1H), 1.60-1.92 (m, 3H), 1.18-1.57 (m, 5H). Calculated for C22H28F3N3O3: 440.2 (M+1). found: 440.2.

Example 7

((3aS,5S,6aR)-5-((3-methoxytetrahydro-2H-pyran-4-yl)amino)hexahydro-2H-cyclopenta[b]furan-3a-yl)(7-(trifluoromethyl)-3,4-dihydroisoquinolin-2(1H)-yl)methanone

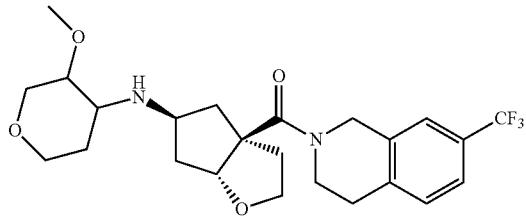 [SMILES: COC1COCCC1N[C@@H]1C[C@H]2OCC[C@@]2(C(=O)N2CCc3ccc(C(F)(F)F)cc3C2)C1]

The title compound was prepared from reaction of the product of Step B of Example 1 and 7-(trifluoromethyl)-1,2,3,4-tetrahydroisoquinoline following the procedure described in Example 1, Step C, and then following Example 1 Steps D through H.
$^1$H NMR (CHLOROFORM-d) δ: 7.45 (d, J=7.6 Hz, 2H), 7.23-7.31 (m, 1H), 4.99-5.10 (m, 1H), 4.72 (br. s., 2H), 4.02-4.16 (m, 1H), 3.70-4.02 (m, 4H), 3.47-3.59 (m, 1H), 3.22-3.46 (m, 6H), 2.86-3.09 (m, 3H), 2.77 (br. s., 1H), 2.13-2.44 (m, 3H), 1.99-2.11 (m, 1H), 1.35-1.88 (m, 5H). Calculated for C24H31F3N2O4: 470.2 (M+1). found: 470.2.

Example 8

((3aS,5S,6aR)-5-((tetrahydro-2H-pyran-4-yl)amino)hexahydro-2H-cyclopenta[b]furan-3a-yl)(7-(trifluoromethyl)-3,4-dihydroisoquinolin-2(1H)-yl)methanone

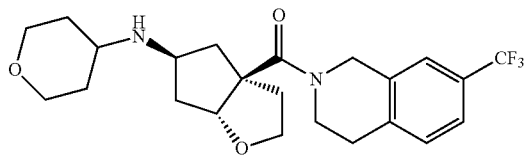 [SMILES: O=C(N1CCc2ccc(C(F)(F)F)cc2C1)[C@@]12CCO[C@@H]1C[C@@H](NC1CCOCC1)C2]

The title compound was prepared from reaction of the product of Step B of Example 1 and 7-(trifluoromethyl)-1,2,3,4-tetrahydroisoquinoline following the procedure described in Example 1, Step C, following Steps D through G, and then using tetrahydro-4H-pyran-4-one following the procedure described in Example 1, Step H.
JNJ46713953, $^1$H NMR (CHLOROFORM-d) δ: 7.31-7.50 (m, 2H), 7.26-7.29 (m, 1H), 5.05 (d, J=4.6 Hz, 1H), 4.72 (br. s., 2H), 3.90-4.05 (m, 3H), 3.70-3.85 (m, 2H), 3.52-3.70 (m, 2H), 3.30-3.45 (m, 2H), 2.95 (br. s., 2H), 2.70 (br. s., 1H), 2.18-2.44 (m, 3H), 2.00-2.12 (m, 1H), 1.60-1.89 (m, 2H), 1.23-1.53 (m, 5H). Calculated for C23H29F3N2O3: 439.2 (M+1). found: 439.2.

Example 9

((3aS,5S,6aR)-5-((3-methoxytetrahydro-2H-pyran-4-yl)amino)hexahydro-2H-cyclopenta[b]furan-3a-yl)(7-(trifluoromethoxy)-3,4-dihydroisoquinolin-2(1H)-yl)methanone

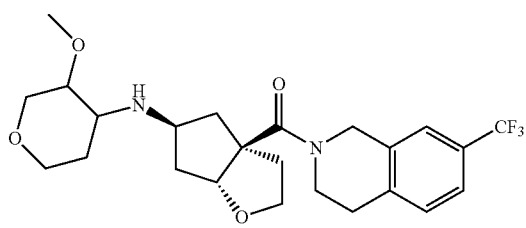 [SMILES: COC1COCCC1N[C@@H]1C[C@H]2OCC[C@@]2(C(=O)N2CCc3ccc(C(F)(F)F)cc3C2)C1]

The title compound was prepared from reaction of the product of Step B of Example 1 and 7-(trifluoromethoxy)-1,2,3,4-tetrahydroisoquinoline following the procedure described in Example 1, Step C, and then following Example 1 Steps D through H. Calculated for C24H31F3N2O5: 485.2 (M+1). found: 485.2.

Example 10

((3aS,5S,6aR)-2-cyclopropyl-5-((3-methoxytetrahydro-2H-pyran-4-yl)amino)hexahydro-2H-cyclopenta[b]furan-3a-yl)(3-(trifluoromethyl)-7,8-dihydro-1,6-naphthyridin-6(5H)-yl)methanone

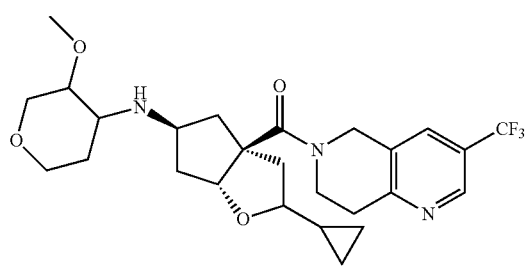

Step A tert-butyl ((1S,4S)-4-(2-oxoethyl)-4-(3-(trifluoromethyl)-5,6,7,8-tetrahydro-1,6-naphthyridine-6-carbonyl)cyclopent-2-en-1-yl)carbamate

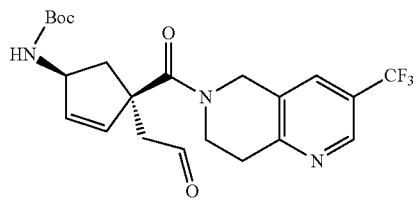 [SMILES: CC(C)(C)OC(=O)N[C@@H]1C=C[C@](CC=O)(C(=O)N2CCc3ncc(C(F)(F)F)cc3C2)C1]

To a solution of the product of Example 1, Step D (417 mg, 0.92 mmol, 1 eq) in DCM (20 mL) at 0° C. was added Dess-Martin periodinane (427 mg, 1.01 mmol, 1.1 eq). After 1 hr, saturated sodium bicarbonate and sodium thiosulfate were added, after 10 minutes, the aqueous was extracted with DCM, the organics combined, dried over MgSO4 and concentrated. Purification by chromatography (12 g column) eluting with 30 to 60% EtOAc/heptane afforded the title compound of Step A. $^1$H NMR (CHLOROFORM-d) δ: 9.74 (s, 1H), 8.70 (s, 1H), 7.72 (s, 1H), 6.31 (dd, J=5.6, 1.7 Hz, 1H), 5.91 (dd, J=5.6, 1.5 Hz, 1H), 5.01 (d, J=17.1 Hz, 1H), 4.65-4.87 (m, 3H), 4.07-4.21 (m, 1H), 3.79-3.95 (m, 1H), 3.10 (q, J=5.6 Hz, 2H), 3.03 (d, J=16.6 Hz, 1H), 2.63 (dd, J=13.6, 7.2 Hz, 1H), 2.52 (dd, J=16.6, 1.5 Hz, 1H), 2.11 (dd, J=13.1, 7.7 Hz, 1H), 1.44 (s, 9H). Calculated for C22H26F3N3O4: 454.2 (M+1). found: 454.2.

Step B tert-butyl ((1S,4S)-4-(2-cyclopropyl-2-hydroxy-ethyl)-4-(3-(trifluoromethyl)-5,6,7,8-tetrahydro-1,6-naphthyridine-6-carbonyl)cyclopent-2-en-1-yl)carbamate

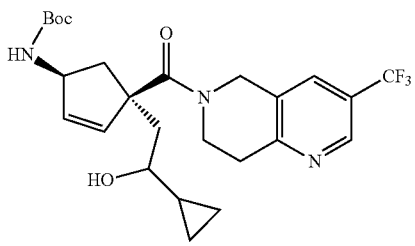 [SMILES: CC(C)(C)OC(=O)N[C@@H]1C=C[C@](CC(O)C2CC2)(C(=O)N2CCc3ncc(C(F)(F)F)cc3C2)C1]

To a solution of cyclopropyl magnesium bromide (6.88 mL of a 0.5 M solution in THF, 3.44 mmol, 8 eq) in THF (5 mL) at 0° C. under Ar was added a solution of the product of Step A (195 mg, 0.43 mmol, 1 eq) in THF (17 mL) dropwise over 30 min. After 45 min, saturated NH₄Cl was added, the solution extracted with ethyl acetate, the organics combined, dried over MgSO₄ and concentrated. Purification by chromatography (12 g column) eluting with 30 to 100% EtOAc/heptane afforded the title compound of Step B as a mix of diastereomers. ¹H NMR (CHLOROFORM-d) δ: 8.70 (br. s., 1H), 7.70 (br. s., 1H), 6.11-6.42 (m, 1H), 5.77 (t, J=5.1 Hz, 1H), 4.81 (d, J=12.2 Hz, 4H), 4.03 (dt, J=12.8, 6.2 Hz, 1H), 3.81-3.98 (m, 1H), 3.59-3.75 (m, 2H), 3.03-3.25 (m, 2H), 2.69-3.00 (m, 2H), 2.19-2.67 (m, 3H), 1.91-2.18 (m, 3H), 1.55-1.88 (m, 5H), 1.42 (s, 9H), 0.88-0.99 (m, 1H), 0.42-0.56 (m, 2H), 0.14-0.35 (m, 2H). Calculated for C25H32F3N3O4: 496.2 (M+1). found: 496.2.

The title compound of Example 10 was made by taking the product of Example 10, Step B and following the procedures from Example 1, Steps E through H.

¹H NMR (CHLOROFORM-d) δ: 8.72 (s, 1H), 7.69 (br. s., 1H), 5.01-5.29 (m, 1H), 4.65-4.90 (m, 2H), 3.74-4.15 (m, 5H), 3.70 (dd, J=11.0, 2.9 Hz, 1H), 3.23-3.55 (m, 7H), 3.14 (br. s., 2H), 3.05 (ddd, J=10.0, 8.2, 6.0 Hz, 1H), 2.69-2.87 (m, 1H), 2.36-2.52 (m, 1H), 2.06-2.36 (m, 3H), 1.66-1.97 (m, 2H), 1.33-1.52 (m, 1H), 0.83-0.98 (m, 1H), 0.43-0.66 (m, 2H), 0.36 (dt, J=8.6, 4.1 Hz, 1H), 0.10-0.24 (m, 1H). Calculated for C26H34F3N3O4: 510.3 (M+1). found: 510.3.

Example 11

((3aS,5S,6aR)-2-ethyl-5-((3-methoxytetrahydro-2H-pyran-4-yl)amino)hexahydro-2H-cyclopenta[b]furan-3a-yl)(3-(trifluoromethyl)-7,8-dihydro-1,6-naphthyridin-6(5H)-yl)methanone

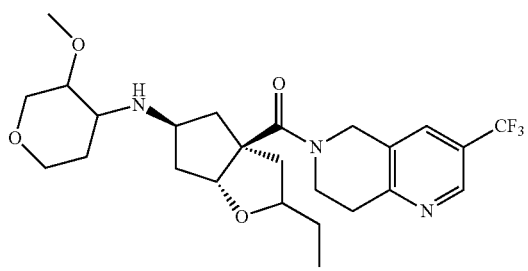

The title compound was prepared from reaction of the product of Example 10, Step A and ethyl magnesium bromide following the procedure described in Example 10, Step B, and then taking that product and following the procedures from Example 1, Steps E through H. ¹H NMR (MeOD) δ: 8.72 (s, 1H), 8.05 (br. s., 1H), 4.94-5.13 (m, 1H), 4.70-4.86 (m, 2H), 4.25 (br. s., 1H), 3.76-4.14 (m, 4H), 3.62-3.75 (m, 1H), 3.35-3.60 (m, 7H), 3.13 (dd, J=3.3, 1.6 Hz, 2H), 2.33-2.75 (m, 3H), 1.69-2.10 (m, 5H), 1.39-1.69 (m, 2H), 0.87-1.01 (m, 3H). Calculated for C25H34F3N3O4: 498.3 (M+1). found: 498.2.

Example 12

((3aS,5S,6aR)-5-((3-methoxytetrahydro-2H-pyran-4-yl)amino)-2-methylhexahydro-2H-cyclopenta[b]furan-3a-yl)(3-(trifluoromethyl)-7,8-dihydro-1,6-naphthyridin-6(5H)-yl)methanone

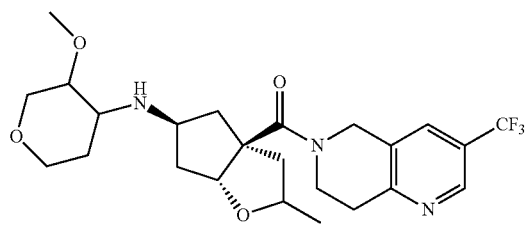

The title compound was prepared from reaction of the product of Example 10, Step A and methyl magnesium bromide following the procedure described in Example 10, Step B, and then taking that product and following the procedures from Example 1, Steps E through H. ¹H NMR (MeOD) δ: 8.72 (br. s., 1H), 8.05 (br. s., 1H), 4.96-5.21 (m, 1H), 4.70-4.87 (m, 2H), 4.21-4.36 (m, 1H), 3.77-4.18 (m, 5H), 3.32-3.62 (m, 7H), 3.00-3.23 (m, 2H), 2.32-2.76 (m, 3H), 1.68-2.06 (m, 5H), 1.16-1.29 (m, 3H). Calculated for C24H32F3N3O4: 484.2 (M+1). found: 484.2.

Example 13

((3aS,5S,6aR)-5-((3-methoxytetrahydro-2H-pyran-4-yl)amino)-2-propylhexahydro-2H-cyclopenta[b]furan-3a-yl)(3-(trifluoromethyl)-7,8-dihydro-1,6-naphthyridin-6(5H)-yl)methanone

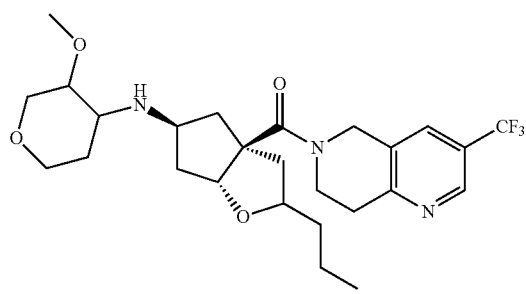

The title compound was prepared from reaction of the product of Example 10, Step A and propyl magnesium bromide following the procedure described in Example 10, Step B, and then taking that product and following the procedures from Example 1, Steps E through H. Calculated for C26H36F3N3O4: 512.3 (M+1). found: 512.2.

Example 14

((3aS,5S,6aR)-2-isobutyl-5-((3-methoxytetrahydro-2H-pyran-4-yl)amino)hexahydro-2H-cyclopenta[b]furan-3a-yl)(3-(trifluoromethyl)-7,8-dihydro-1,6-naphthyridin-6(5H)-yl)methanone

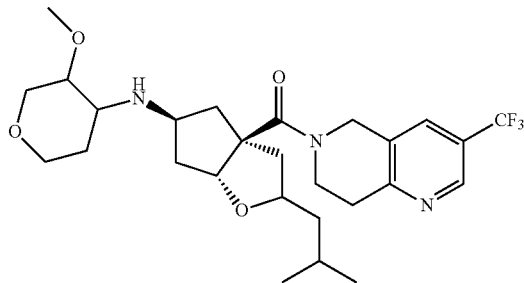

The title compound was prepared from reaction of the product of Example 10, Step A and isobutyl magnesium bromide following the procedure described in Example 10, Step B, and then taking that product and following the procedures from Example 1, Steps E through H.

Calculated for C27H38F3N3O4: 526.3 (M+1). found: 526.3.

Example 15

((3aS,5S,6aR)-2-cyclohexyl-5-((3-methoxytetrahydro-2H-pyran-4-yl)amino)hexahydro-2H-cyclopenta[b]furan-3a-yl)(3-(trifluoromethyl)-7,8-dihydro-1,6-naphthyridin-6(5H)-yl)methanone

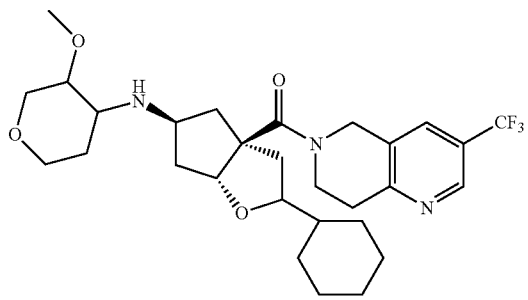

The title compound was prepared from reaction of the product of Example 10, Step A and cyclohexyl magnesium bromide following the procedure described in Example 10, Step B, and then taking that product and following the procedures from Example 1, Steps E through H.

$^1$H NMR (CHLOROFORM-d) δ: 8.71 (br. s., 1H), 7.69 (br. s., 1H), 4.98-5.21 (m, 1H), 4.65-4.94 (m, 2H), 3.68-4.17 (m, 5H), 3.23-3.64 (m, 8H), 3.13 (br. s., 2H), 2.69-2.86 (m, 1H), 1.86-2.35 (m, 6H), 1.32-1.79 (m, 8H), 1.10-1.30 (m, 3H), 0.86-1.06 (m, 2H). Calculated for C29H40F3N3O4: 552.3 (M+1). found: 553.2.

Example 16

((3aS,5S,6aR)-5-((3-methoxytetrahydro-2H-pyran-4-yl)amino)-2-phenylhexahydro-2H-cyclopenta[b]furan-3a-yl)(3-(trifluoromethyl)-7,8-dihydro-1,6-naphthyridin-6(5H)-yl)methanone

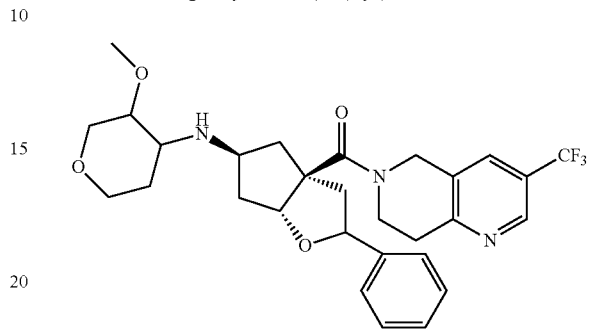

The title compound was prepared from reaction of the product of Example 10, Step A and phenyl magnesium bromide following the procedure described in Example 10, Step B, and then taking that product and following the procedures from Example 1, Steps E through H. Calculated for C29H34F3N3O4: 546.3 (M+1). found: 546.3.

Example 17

((3aS,5S,6aR)-5-((3-methoxytetrahydro-2H-pyran-4-yl)amino)-2-(1-methyl-1H-pyrazol-5-yl)hexahydro-2H-cyclopenta[b]furan-3a-yl)(3-(trifluoromethyl)-7,8-dihydro-1,6-naphthyridin-6(5H)-yl)methanone

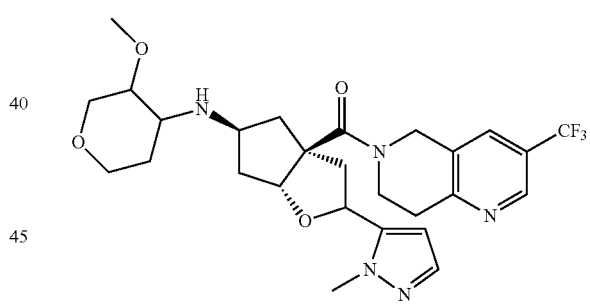

Step A tert-butyl ((1S,4S)-4-(2-hydroxy-2-(1-methyl-1H-pyrazol-5-yl)ethyl)-4-(3-(trifluoromethyl)-5,6,7,8-tetrahydro-1,6-naphthyridine-6-carbonyl)cyclopent-2-en-1-yl)carbamate

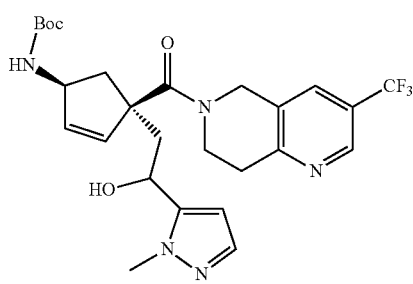 [SMILES: Cn1nccc1C(O)C[C@]1(C(=O)N2CCc3ncc(C(F)(F)F)cc3C2)C=C[C@@H](NC(=O)OC(C)(C)C)C1]

To a solution of 1-methylpyrazole (0.165 mmol, 1.98 mmol, 3 eq) in THF (8 mL) at −78° C. under Ar was added n-BuLi (0.77 mL of a 2.5 M solution in hexane, 1.92 mmol, 2.9 eq) and the solution stirred 1 hr. Then a solution of the product of Example 10, Step A (300 mg, 0.66 mmol, 1 eq) in THF (8 mL) was added over 5 min. After 1 hr, saturated NH₄Cl was added, the solution extracted with ethyl acetate, the organics combined, dried over MgSO₄ and concentrated. Purification by chromatography (12 g column) eluting with 50 to 100% EtOAc/heptane to 5 to 10% methanol/DCM afforded the title compound of Step A as a mix of diastereomers. $^1$H NMR (CHLOROFORM-d) δ: 8.70 (s, 1H), 7.62-7.80 (m, 1H), 7.33 (d, J=8.8 Hz, 1H), 6.19-6.49 (m, 1H), 6.09 (br. s., 1H), 5.87 (dd, J=17.9, 5.6 Hz, 1H), 4.54-5.03 (m, 5H), 3.74-3.96 (m, 4H), 3.48 (s, 1H), 2.90-3.23 (m, 2H), 2.46-2.87 (m, 2H), 2.06-2.39 (m, 2H), 1.73-1.98 (m, 1H), 1.43 (br. s., 9H). Calculated for C27H34F3N5O4: 558.2 (M+23). found: 558.2.

The title compound of Example 17 was made by taking the product of Example 17, Step A and following the procedures from Example 1, Steps E through H.

$^1$H NMR (CHLOROFORM-d) δ: 8.73 (br. s., 1H), 7.72 (br. s., 1H), 7.32-7.48 (m, 1H), 5.90-6.28 (m, 1H), 5.08-5.36 (m, 1H), 4.64-4.98 (m, 2H), 3.76-4.17 (m, 7H), 3.50-3.74 (m, 1H), 3.23-3.50 (m, 6H), 3.16 (br. s., 2H), 2.66-2.86 (m, 1H), 2.15-2.64 (m, 4H), 1.96-2.05 (m, 1H), 1.42-1.91 (m, 3H). Calculated for C27H34F3N5O4: 550.3 (M+1). found: 550.2.

Example 18

((3 aS,5S,6aR)-5-((3-methoxytetrahydro-2H-pyran-4-yl)amino)-2-(1-methyl-1H-imidazol-2-yl)hexahydro-2H-cyclopenta[b]furan-3a-yl)(3-(trifluoromethyl)-7,8-dihydro-1,6-naphthyridin-6(5H)-yl)methanone

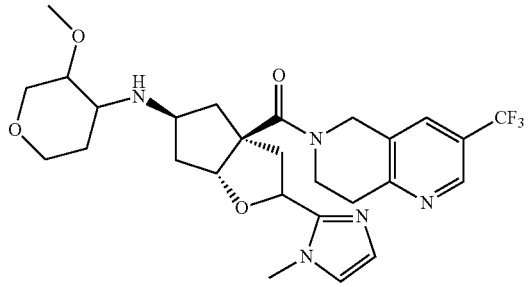

The title compound was prepared from reaction of the product of Example 10, Step A and 1-methylimidazole following the procedure described in Example 17, Step A, and then taking that product and following the procedures described in Example 1, Steps E through H.

Calculated for C27H34F3N5O4: 550.3 (M+1). found: 550.2.

Example 19

((3aS,5S,6aR)-5-((3-methoxytetrahydro-2H-pyran-4-yl)amino)-2-(thiazol-2-yl)hexahydro-2H-cyclopenta[b]furan-3a-yl)(3-(trifluoromethyl)-7,8-dihydro-1,6-naphthyridin-6(5H)-yl)methanone

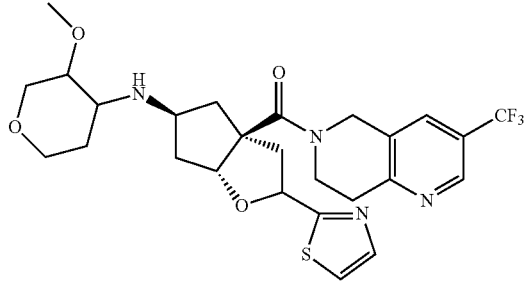

The title compound was prepared from reaction of the product of Example 10, Step A and thiazole following the procedure described in Example 17, Step A, and then taking that product and following the procedures described in Example 1, Steps E through H. Calculated for C26H31F3N4O4S: 553.3 (M+1). found: 553.3.

Example 20

((3 aS,5S,6aR)-5-((3-methoxytetrahydro-2H-pyran-4-yl)amino)-2,2-dimethylhexahydro-2H-cyclopenta[b]furan-3a-yl)(3-(trifluoromethyl)-7,8-dihydro-1,6-naphthyridin-6(5H)-yl)methanone

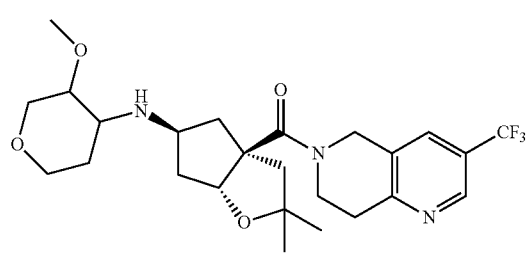 [SMILES: COC1COCCC1N[C@@H]1C[C@H]2OC(C)(C)C[C@@]2(C(=O)N2CCc3ncc(C(F)(F)F)cc3C2)C1]

Step A 2-((1S,4S)-4-((tert-butoxycarbonyl)amino)-1-(3-(trifluoromethyl)-5,6,7,8-tetrahydro-1,6-naphthyridine-6-carbonyl)cyclopent-2-en-1-yl)acetic acid

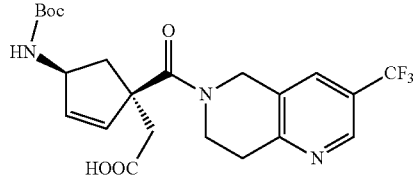 [SMILES: CC(C)(C)OC(=O)N[C@@H]1C=C[C@](CC(=O)O)(C(=O)N2CCc3ncc(C(F)(F)F)cc3C2)C1]

To a solution of the product of Example 1, Step D (508 mg, 1.12 mmol, 1 eq) in acetone (10 mL) at 0° C. was added Jones oxidation solution (0.46 mL, 1.23 mmol, 1.1 eq). After 2 hr, water was added, the aqueous was extracted with ethyl acetate, the organics combined, dried over MgSO₄ and concentrated to afford the product of Step A that was used unpurified in the next step. Calculated for C22H26F3N3O5: 492.2 (M+23). found: 492.1.

Step B methyl 2-((1S,4S)-4-((tert-butoxycarbonyl)amino)-1-(3-(trifluoromethyl)-5,6,7,8-tetrahydro-1,6-naphthyridine-6-carbonyl)cyclopent-2-en-1-yl)acetate

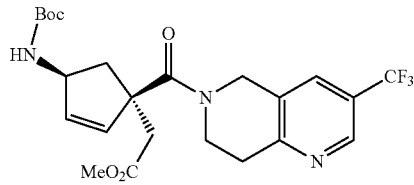 [SMILES: COC(=O)C[C@]1(C(=O)N2CCc3ncc(C(F)(F)F)cc3C2)C=C[C@@H](NC(=O)OC(C)(C)C)C1]

To a solution of the product of Step A (436 mg, 0.84 mmol, 1 eq) in methanol (20 mL) at 0° C. was added trimethylsilyl diazomethane (5 mL of a 2 M solution in hexanes, 10 mmol, 11.9 eq) until the yellow color persisted. The yellow solution was concentrated. Purification by chromatography (24 g column) eluting with 40 to 80% EtOAc/heptane afforded the product of Step B. $^1$H NMR (CHLOROFORM-d) δ: 8.70 (s, 1H), 7.69 (s, 1H), 6.37 (d, J=5.4 Hz, 1H), 5.87 (d, J=5.4 Hz, 1H), 4.98 (d, J=17.4 Hz, 1H), 4.63-4.83 (m, 3H), 4.07-4.20 (m, 1H), 3.79-3.93 (m, 1H), 3.64 (s, 3H), 3.08-3.19 (m, 2H), 3.04 (d, J=15.9 Hz, 1H), 2.62 (dd, J=13.4, 7.1 Hz, 1H), 2.46 (d, J=15.7 Hz, 1H), 2.01-2.12 (m, 1H), 1.43 (s, 9H). Calculated for C23H28F3N3O5: 506.2 (M+23). found: 506.2.

Step C tert-butyl ((1S,4S)-4-(2-hydroxy-2-methylpropyl)-4-(3-(trifluoromethyl)-5,6,7,8-tetrahydro-1,6-naphthyridine-6-carbonyl)cyclopent-2-en-1-yl)carbamate

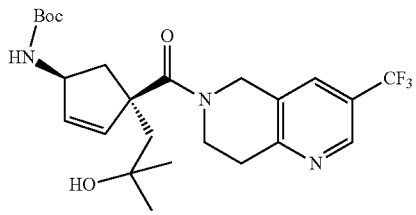 [SMILES: CC(C)(O)C[C@]1(C(=O)N2CCc3ncc(C(F)(F)F)cc3C2)C=C[C@@H](NC(=O)OC(C)(C)C)C1]

To a solution of methyl magnesium chloride (2.62 mL of a 3 M solution in THF, 7.86 mmol, 20 eq) in THF (6 mL) at 0° C. under Ar was added a solution of the product of Step B (190 mg, 0.39 mmol, 1 eq) in THF (6 mL) dropwise over 30 min. After 30 min, saturated NH4Cl was added, the solution extracted with ethyl acetate, the organics combined, dried over MgSO4 and concentrated. Purification by chromatography (12 g column) eluting with 40 to 100% EtOAc/heptane afforded the product of Step C. $^1$H NMR (CHLOROFORM-d) δ: 8.70 (s, 1H), 7.69 (s, 1H), 6.47 (d, J=5.4 Hz, 1H), 5.75 (dd, J=5.6, 1.5 Hz, 1H), 4.60-4.96 (m, 4H), 4.05 (d, J=13.7 Hz, 1H), 3.89 (dt, J=13.3, 6.4 Hz, 1H), 3.07-3.19 (m, 2H), 2.54 (dd, J=12.6, 6.5 Hz, 1H), 2.10-2.27 (m, 2H), 1.80-1.96 (m, 2H), 1.35-1.49 (m, 9H), 1.26 (s, 3H), 1.22 (s, 3H). Calculated for C24H32F3N3O4: 506.2 (M+23). found: 506.2.

The title compound of Example 20 was made by taking the product of Step C and following the procedures described in Example 1, Steps E through H.

$^1$H NMR (CHLOROFORM-d) δ: 8.72 (br. s., 1H), 7.69 (br. s., 1H), 5.16-5.27 (m, 1H), 4.78 (br. s., 2H), 4.01-4.13 (m, 1H), 3.75-3.99 (m, 4H), 3.53-3.67 (m, 1H), 3.22-3.48 (m, 6H), 3.12 (br. s., 2H), 2.79 (d, J=10.0 Hz, 1H), 2.09-2.40 (m, 3H), 1.84-2.00 (m, 2H), 1.68-1.78 (m, 2H), 1.42-1.53 (m, 1H), 1.34 (s, 3H), 1.16 (s, 3H). Calculated for C25H34F3N3O4: 498.2 (M+1). found: 498.2.

Example 21

(3aS,5S,6aR)-5-((3-methoxytetrahydro-2H-pyran-4-yl)amino)-3a-(3-(trifluoromethyl)-5,6,7,8-tetrahydro-1,6-naphthyridine-6-carbonyl)hexahydro-2H-cyclopenta[b]furan-2-one

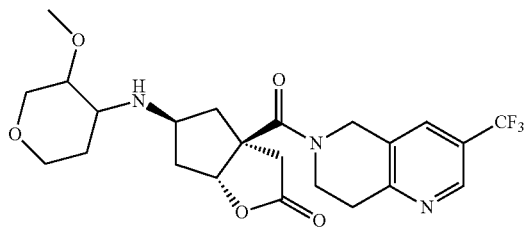 [SMILES: COC1COCCC1N[C@@H]1C[C@H]2OC(=O)C[C@@]2(C(=O)N2CCc3ncc(C(F)(F)F)cc3C2)C1]

The title compound of Example 21 was made by taking the product of Example 20, Step A and following the procedures described in Example 1, Steps E through H.

$^1$H NMR (CHLOROFORM-d) δ: 8.74 (br. s., 1H), 7.71 (br. s., 1H), 5.70 (d, J=4.2 Hz, 1H), 4.55-4.88 (m, 2H), 4.08 (d, J=11.7 Hz, 1H), 3.93 (d, J=11.5 Hz, 1H), 3.80 (br. s., 1H), 3.47-3.61 (m, 2H), 3.24-3.46 (m, 5H), 3.15 (br. s., 2H), 3.03 (d, J=14.2 Hz, 1H), 2.83 (br. s., 2H), 2.23-2.47 (m, 2H), 1.53-1.76 (m, 6H). Calculated for C23H28F3N3O5: 484.2 (M+1). found: 484.2.

Example 22

((3aR,5S,6aR)-5-((3-methoxytetrahydro-2H-pyran-4-yl)amino)hexahydro-2H-cyclopenta[b]thiophen-3a-yl)(3-(trifluoromethyl)-7,8-dihydro-1,6-naphthyridin-6(5H)-yl)methanone

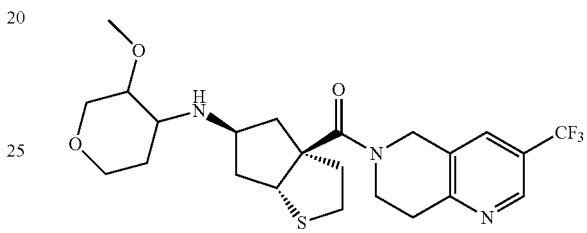

Step A

S-(2-((1S,4S)-4-((tert-butoxycarbonyl)amino)-1-(3-(trifluoromethyl)-5,6,7,8-tetrahydro-1,6-naphthyridine-6-carbonyl)cyclopent-2-en-1-yl)ethyl)ethanethioate

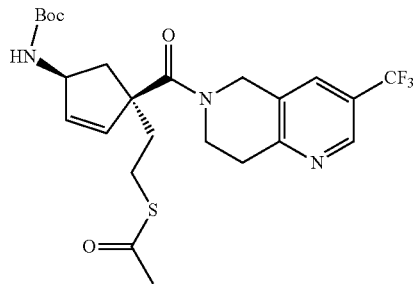 [SMILES: CC(=O)SCC[C@]1(C(=O)N2CCc3ncc(C(F)(F)F)cc3C2)C=C[C@@H](NC(=O)OC(C)(C)C)C1]

To a solution of the product of Example 1, Step D (1950 mg, 3.98 mmol, 1 eq) in THF (40 mL) at rt under Ar was added triphenylphosphine (2.09 g, 7.96 mmol, 2 eq), diisopropylazodicarboxylate (1.55 mL, 7.96 mmol, 2 eq) and thioacetic acid (0.59 mL, 7.96 mmol, 2 eq). After 2 hr, water and saturated NaHCO3 were added, the aqueous was extracted with ether, the organics combined, dried over MgSO4 and concentrated. Purification by chromatography (80 g column) eluting with 30 to 60% EtOAc/heptane afforded the product of Step A. $^1$H NMR (CHLOROFORM-d) δ: 8.71 (s, 1H), 7.71 (s, 1H), 6.21 (dd, J=5.6, 1.7 Hz, 1H), 5.80 (dd, J=5.6, 2.0 Hz, 1H), 4.75-4.94 (m, 3H), 4.64-4.75 (m, 1H), 3.96-4.07 (m, 1H), 3.86-3.96 (m, 1H), 3.14 (t, J=5.7 Hz, 2H), 2.69-2.79 (m, 2H), 2.65 (dd, J=13.4, 8.1 Hz, 1H), 2.27 (s, 3H), 1.95-2.13 (m, 2H), 1.81-1.94 (m, 1H), 1.44 (s, 9H). Calculated for C24H30F3N3O4S: 536.2 (M+23). found: 536.2.

Step B tert-butyl ((1S,4S)-4-(2-mercaptoethyl)-4-(3-(trifluoromethyl)-5,6,7,8-tetrahydro-1,6-naphthyridine-6-carbonyl)cyclopent-2-en-1-yl)carbamate

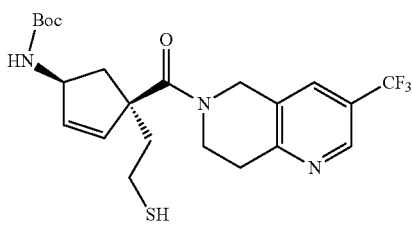 [SMILES: CC(C)(C)OC(=O)N[C@@H]1C=C[C@](CCS)(C(=O)N2CCc3ncc(C(F)(F)F)cc3C2)C1]

To a solution of the product of Step A (1.74 g, 3.39 mmol, 1 eq) in methanol (100 mL) at rt under Ar (degassed) was added 0.2 N NaOH (85 mL, 85 mmol, 5 eq) that was degassed by bubbling Ar through the solution prior to addition. After 2 hr, the methanol was concentrated, 6 N HCl was added until the solution was acidic, the aqueous was extracted with DCM, the organics combined, dried over $MgSO_4$ and concentrated to afford the product of Step B which was used unpurified in the next step. Calculated for $C22H28F3N3O3S$: 494.2 (M+23). found: 494.1.

Step C tert-butyl ((3aR,5S,6aR)-3a-(3-(trifluoromethyl)-5,6,7,8-tetrahydro-1,6-naphthyridine-6-carbonyl)hexahydro-2H-cyclopenta[b]thiophen-5-yl)carbamate

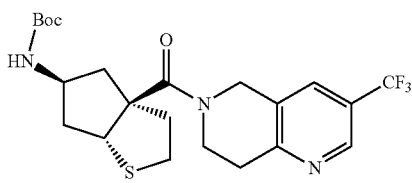

To a solution of the product of Step B (1.25 g, 2.65 mmol, 1 eq) in benzene (300 mL) at rt under Ar (degassed) was added AIBN (435 mg, 2.65 mmol, 1 eq) and the solution heated to 85° C. for 3 days, then concentrated. Purification by chromatography (40 g column) eluting with 25 to 60 to 100% EtOAc/heptane afforded the product of Step C. $^1$H NMR (CHLOROFORM-d) δ: 8.72 (s, 1H), 7.69 (s, 1H), 4.65-4.90 (m, 3H), 4.23-4.60 (m, 2H), 3.87-4.06 (m, 2H), 3.10-3.16 (m, 2H), 2.99-3.09 (m, 1H), 2.87-2.98 (m, 1H), 1.95-2.38 (m, 6H), 1.40 (s, 9H). Calculated for $C22H28F3N3O3S$: 494.2 (M+23). found: 494.1.

The title compound of Example 22 was made by taking the product of Example 22, Step C and following the procedures described in Example 1, Steps G and H.

$^1$H NMR (CHLOROFORM-d) δ: 8.71 (s, 1H), 7.69 (s, 1H), 4.73-4.93 (m, 2H), 4.67 (br. s., 1H), 4.04-4.17 (m, 1H), 3.94 (t, J=5.9 Hz, 3H), 3.61-3.77 (m, 1H), 3.36-3.47 (m, 4H), 3.26-3.36 (m, 2H), 3.06-3.19 (m, 2H), 2.80-3.05 (m, 3H), 2.31 (br. s., 2H), 2.05-2.21 (m, 3H), 1.83-1.99 (m, 1H), 1.60-1.83 (m, 2H). Calculated for $C23H30F3N3O3S$: 486.2 (M+1). found: 486.2.

Example 23

((3aS,5S,6aR)-5-(((3S,4S)-3-methoxytetrahydro-2H-pyran-4-yl)amino)hexahydro-2H-cyclopenta[b]furan-3a-yl)(4-(4-(trifluoromethyl)pyrimidin-2-yl)piperazin-1-yl)methanone

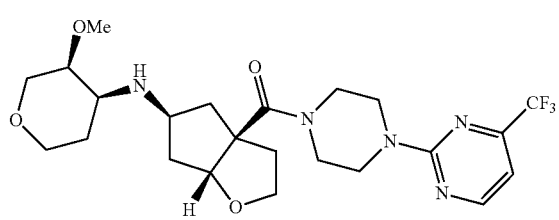 [SMILES: CO[C@@H]1COCC[C@@H]1N[C@@H]1C[C@H]2OCC[C@@]2(C(=O)N2CCN(c3nccc(C(F)(F)F)n3)CC2)C1]

Step A tert-butyl ((5S,7S)-1-oxo-2-oxaspiro[4.4]non-8-en-7-yl)carbamate

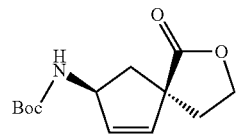 [SMILES: CC(C)(C)OC(=O)N[C@@H]1C=C[C@@]2(CCOC2=O)C1]

A 12-L three-neck round bottom flask with overhead mechanical stirrer, 2-L addition funnel and nitrogen inlet was charged the product of Example 1, Step A (1149 g, 2.875 mol, 1 eq) and THF (5.75 L). The addition funnel was charged with TBAF (1M solution in THF, 2.875 L, 2.875 mol, 1 eq) and this solution was added dropwise over ~1 h. The temperature increased from 17 to 21° C. and the reaction was clear orange at the end. The reaction was stirred for 1 h at rt, when it was judged complete by TLC and HPLC. The reaction was poured into a 22-L separatory flask charged with EtOAc (4 L) and the organic layer was washed with brine (2 L). The organic layer was washed with additional brine (3×2 L) and these aqueous fractions were discarded. Heptane (4 L) was added and the organic layer was washed with water (3×2 L), brine (2×2 L) and the clear organic layer was checked by NMR for removal of n-$Bu_4NX$. The organic layer was evaporated at 45° C. to about 750 mL, when the solution became hazy, heptane (800 mL) was added and instant crystallization of a white solid resulted. More heptane (300 mL) was added and the mixture was swirled at 40° C. for 10 min on the rotovap bath. Ice was added to bath and the suspension was stirred at 13° C. for 10 min. The solid was filtered on a Buchner funnel, washed with heptane (3×100 mL) and provided the product of Step A. $^1$H NMR (CHLOROFORM-d) δ: 6.02 (dd, J=5.4, 2.4 Hz, 1H), 5.77 (d, J=5.4 Hz, 1H), 5.21 (d, J=9.0 Hz, 1H), 4.91 (t, J=8.7 Hz, 1H), 4.37 (dd, J=7.5, 6.5 Hz, 2H), 2.21-2.39 (m, 3H), 2.07

(dd, J=13.8, 2.6 Hz, 1H), 1.44 (s, 9H). Calculated for C13H19NO4: 276.1 (M+23). found: 276.1.

Step B tert-butyl ((1S,4S)-4-(2-hydroxyethyl)-4-(hydroxymethyl)cyclopent-2-en-1-yl)carbamate

To a 5-L three-neck round bottom flask equipped with a mechanical stirrer, Claisen adapter with temperature probe and nitrogen inlet, and N₂ outlet was purged with nitrogen for 2 h before use. The product of Step A (255.9 g, 1.01 mol, 1 eq) and MeOH (2 L) were added and the solution was chilled to 2° C. in an ice bath. NaBH₄ (75 g, 1.98 mol, 2 eq) was added in ~5 equal portions; the temperature exothermed to 17° C. before coming back to 6° C., when the next portion was added. The addition took ~2.5 h and the reaction was judged complete by HPLC after the last addition. The reaction was quenched at 7° C. by addition of aqueous NH₄Cl (saturated, 1 L), wherein the temperature rose to about 10° C. The white hazy mixture was concentrated on a rotary evaporate to about 1 L (45° C. bath) when a white solid with some liquid resulted. The mixture was diluted with water and EtOAc (1 L each), transferred to a separatory funnel and the layers were separated. The aqueous layer was extracted with EtOAc (3×250 mL). The combined organics were washed with brine (125 mL), dried over MgSO₄, filtered through Celite and evaporated at a bath temperature of 55° C. and provided the product of Step B as a thick oil. ¹H NMR (CHLOROFORM-d) δ: 5.74 (s, 2H), 4.65-4.95 (m, 2H), 3.70 (t, J=5.7 Hz, 2H), 3.40-3.57 (m, 2H), 2.76 (br. s., 1H), 2.28 (br. s., 1H), 2.19 (dd, J=13.4, 8.8 Hz, 1H), 1.70 (t, J=5.7 Hz, 2H), 1.55 (dd, J=13.8, 4.0 Hz, 1H), 1.44 (s, 9H). Calculated for C13H23NO4: 280.2 (M+23). found: 280.2.

Step C tert-butyl ((3 aR,5S,6S,6aS)-3a-(hydroxymethyl)-6-(phenylselanyl)hexahydro-2H-cyclopenta[b]furan-5-yl)carbamate

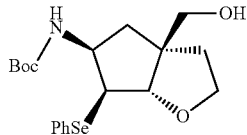

To a 12-L three-neck round bottom flask equipped with a mechanical stirrer, Claisen adapter with a nitrogen inlet and a temperature probe, and a nitrogen outlet was charged with the product of Step B (382 g, 1.26 mol, 1 eq) and CH₂Cl₂ (6.5 L). N-(phenylseleno)phthalimide (419 g, 1.39 mol, 1.1 eq) was added followed by BF₃ etherate (16 mL, 0.126 mol, 0.1 eq) directly added by graduated cylinder. The reaction steadily climbed from 15° C. to 24° C. and within 10 min, the reaction formed a pink precipitate. Ten min later, the reaction became thick with a white precipitate and the temperature began to decrease. The reaction was checked by HPLC and found to be complete. The reaction was filtered through Celite (removing the phthalimide impurity), the filter cake was washed with CH₂Cl₂ (750 mL) until the filtrate was no longer orange. The filtrate was transferred to a separatory funnel, washed with aqueous NaOH (0.5 M, 2×1350 mL), brine (2×1 L), and the organic layer was dried over Na₂SO₄. [A second run was conducted with 382 g of the product of Step B, under the same conditions, and was worked up and combined at this point]. With about 3 L organics left, toluene (3 L, ~4 mL/g starting material) was added and the evaporation continued. Shortly after the toluene addition, crystallization occurred. The 20-L round bottom flask was transferred to a heating mantel, and the contents heated to 80° C., until the solid dissolved. The flask was transferred back to the rotary evaporator, reference material was used to seed the crystallization, and the flask swirled (no heat) until the product started to crystallize. Ice was added to the bath and the contents of the flask swirled at 15° C. (external temp) for 30 min. The product was filtered, washed with ice-cold toluene and air-dried for 1 h, and afforded the product of Step C. ¹H NMR (CHLOROFORM-d) δ: 7.49-7.56 (m, 2H), 7.23-7.29 (m, 3H), 5.05 (br. s., 1H), 4.46 (br. s., 1H), 4.29 (s, 1H), 3.86-3.97 (m, 2H), 3.57-3.69 (m, 3H), 1.98-2.08 (m, 1H), 1.86-1.97 (m, 2H), 1.73-1.86 (m, 2H), 1.41 (s, 9H). Calculated for C19H27NO4Se: 436.1 (M+23). found: 436.1.

Step D tert-butyl ((3aR,5S,6aR)-3a-(hydroxymethyl)hexahydro-2H-cyclopenta[b]furan-5-yl)carbamate

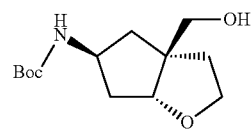

A 22-L four-neck round bottom flask equipped with mechanical stirrer, heating mantel, temperature probe, nitrogen inlet, and a reflux condenser with nitrogen outlet was purged with nitrogen for 30 min before use. The product of Step C (603.5 g, 1.46 mol, 1 eq), AIBN (241 g, 1.46 mol, 1 eq), tris(trimethylsilyl)silane (910 mL, 2.93 mol, 2 eq) and toluene (16.3 L) were added and the suspension was degassed with nitrogen purge through the suspension for 20 min. The reaction was heated to 80-83° C. for 1 h after which time the heat was shut off, and the reaction cooled to rt over 12-18 h. TLC showed the reaction was complete. The reaction was poured directly into a BIOTAGE dry 5-kg column that was eluted with 16 L of 50% EtOAc in heptane, followed by 32 L of EtOAc and provided the product of Step D of a golden thick oil, which slowly crystallized on standing. ¹H NMR (CHLOROFORM-d) δ: 4.64 (brd. s, 1H), 4.07-4.25 (m, 2H), 3.89 (ddd, J=8.8, 7.2, 4.5 Hz, 1H), 3.53-3.67 (m, 3H), 2.17 (dd, J=13.3, 6.2 Hz, 1H), 1.98-2.06 (m, 1H), 1.86-1.97 (m, 1H), 1.68-1.81 (m, 2H), 1.46-1.56 (m, 2H), 1.44 (s, 9H). Calculated for C13H23NO4: 202.2 (M−55). found: 202.2.

Step E (3aS,5S,6aR)-5-((tert-butoxycarbonyl)amino)hexahydro-2H-cyclopenta[b]furan-3a-carboxylic acid

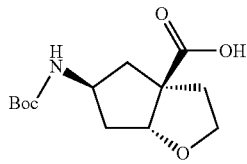 [SMILES: CC(C)(C)OC(=O)N[C@@H]1C[C@H]2OCC[C@@]2(C(=O)O)C1]

A 22-L four-neck round bottom flask equipped with a mechanical stirrer, nitrogen inlet, 1-L addition funnel with nitrogen outlet, a temperature probe, and an external bath for cooling was purged with nitrogen overnight. A solution of the product of Step D (426 g, 1.57 mol) and acetone (8.1 L) was added, the flask was cooled to 7° C., and the addition funnel was charged with Jones reagent (710 mL). The oxidant was added dropwise over 1 h 20 min, keeping the temp between 7-9° C. After the first 200 mL was added, a green ball formed that made stirring very difficult. After about ½ of the oxidant was added, LCMS was run to follow the reaction. At the end of addition, olive green suspension resulted with a hint of red (excess Jones). The ice bath was removed, the reaction was stirred at rt for 1 h after which time the reaction was judged complete. Isopropyl alcohol (40 mL) was added, the reaction stirred for 25 min, and water (800 mL) was added, that caused a nice separation of green chunk from the acetone/water layer. The water/acetone was decanted off and evaporated. The green chunk was dissolved in water (1.5 L), transferred to a separatory funnel and extracted with CH$_2$Cl$_2$ (1 L). The aqueous layer was checked by TLC and found to contain no product, so it was discarded. The organic extract was saved for combining later. The green water/acetone concentrate was evaporated to about 5-7 L, until the solution looked hazy. The concentrate was transferred to a separatory funnel and extracted with CH$_2$Cl$_2$ (1×3 L, 3×1 L) and the aqueous layer checked after each extraction for the presence of product. The combined extracts were washed with brine (250 mL) which caused a terrible emulsion. The emulsion was broken by addition of water and EtOAc (~500 mL). The organic layer was dried (Na$_2$SO$_4$) but not very effectively as some water came through during the filtration. Near the end of the evaporation, the distillation rate slowed, and a thick yellow oil resulted. MeCN (500 mL) was added to the pot, the rotary evaporator bath warmed to 50° C., and the contents seeded with reference material. A fine white solid slowly formed within 10 min or so. Seeding was done a second time, and continued swirling for another 10 min at 50° C. Crystallization was visually detected, the bath was drained and filled with ice, and the flask swirled at 0° C. for 30 min, resulting in a thick white solid. The solid was filtered, washed with ice-cold MeCN (2×100 mL) and the solid was air-dried overnight. The product of Step E was isolated as a white, free-flowing solid. $^1$H NMR (MeOH) δ: 4.43 (d, J=5.4 Hz, 1H), 4.00-4.13 (m, 1H), 3.89-3.98 (m, 1H), 3.63 (td, J=9.1, 5.7 Hz, 1H), 2.54 (ddd, J=12.6, 5.7, 3.2 Hz, 1H), 1.93-2.13 (m, 3H), 1.74-1.87 (m, 1H), 1.53-1.66 (m, 1H), 1.43 (s, 9H). Calculated for C13H21NO5: 294.1 (M+23). found: 294.1.

Step F (benzyl 4-((3aS,5S,6aR)-5-((tert-butoxycarbonyl)amino)hexahydro-2H-cyclopenta[b]furan-3a-carbonyl)piperazine-1-carboxylate

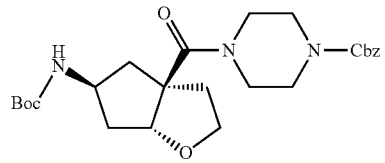 [SMILES: CC(C)(C)OC(=O)N[C@@H]1C[C@H]2OCC[C@@]2(C(=O)N2CCN(C(=O)OCc3ccccc3)CC2)C1]

The product of Step F was prepared from the reaction of the product of Step E and benzyl piperazine-1-carboxylate following the procedure from Example 1, Step C. Calculated for C25H35N3O6: 496.2 (M+23). found: 496.0.

Step G benzyl 4-((3aS,5S,6aR)-5-aminohexahydro-2H-cyclopenta[b]furan-3a-carbonyl)piperazine-1-carboxylate

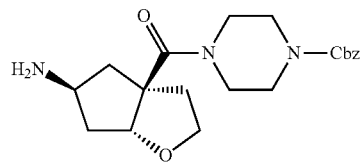 [SMILES: N[C@@H]1C[C@H]2OCC[C@@]2(C(=O)N2CCN(C(=O)OCc3ccccc3)CC2)C1]

The product of Step G was prepared from the reaction of the product of Step F following the procedure from Example 1, Step G. Calculated for C20H27N3O4: 374.2 (M+1). found: 374.2.

Step H benzyl 4-((3aS,5S,6aR)-5-(((3S,4S)-3-methoxytetrahydro-2H-pyran-4-yl)amino)hexahydro-2H-cyclopenta[b]furan-3a-carbonyl)piperazine-1-carboxylate

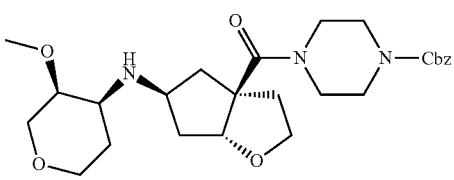 [SMILES: CO[C@@H]1COCC[C@@H]1N[C@@H]1C[C@H]2OCC[C@@]2(C(=O)N2CCN(C(=O)OCc3ccccc3)CC2)C1]

The product of Step H was prepared from the reaction of the product of Step G and (R)-3-methoxydihydro-2H-pyran-4(3H)-one (Intermediate 1) following the procedure described in Example 1, Step H. Calculated for C26H37N3O6: 488.3 (M+1). found: 488.1.

Step I ((3aS,5S,6aR)-5-(((3S,4S)-3-methoxytetrahydro-2H-pyran-4-yl)amino)hexahydro-2H-cyclopenta[b]furan-3a-yl)(piperazin-1-yl)methanone

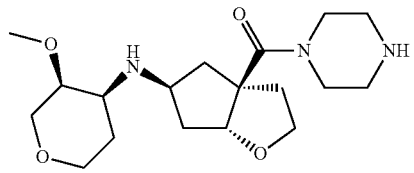 [SMILES: CO[C@@H]1COCC[C@@H]1N[C@@H]1C[C@H]2OCC[C@@]2(C(=O)N2CCNCC2)C1]

A solution of the product of Step H (405 mg, 0.83 mmol, 1 eq) and 5% Pd/C (100 mg) in ethanol (10 mL) at rt was placed under a balloon of hydrogen gas overnight. The suspension was filtered through celite, washed with methanol, and the filtrates concentrated to give the product of Step I as a gum. Calculated for C18H31N3O4: 354.2 (M+1). found: 354.2.

Step J ((3aS,5S,6aR)-5-(((3S,4S)-3-methoxytetrahydro-2H-pyran-4-yl)amino)hexahydro-2H-cyclopenta[b]furan-3a-yl)(4-(4-(trifluoromethyl)pyrimidin-2-yl)piperazin-1-yl)methanone

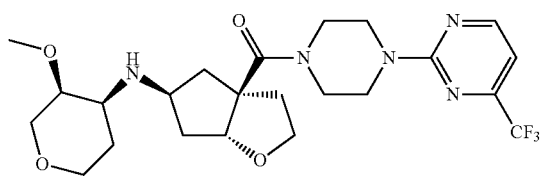

A solution of the product of Step I (40 mg, 0.11 mmol, 1 eq), DIEA (0.06 mL, 0.34 mmol, 3 eq) and 2-chloro-4-(trifluoromethyl)pyrimidine (0.04 mL, 0.34 mmol, 3 eq) in a mixture of 10:1 dioxane/DMSO (1 mL) in a vial under Ar was heated to 100° C. overnight. Water was added, the solution was extracted with DCM, the organics combined, dried over MgSO4 and concentrated. Purification by chromatography (4 g column) eluting with 5 to 10% MeOH/DCM afforded the title compound of Example 23. $^1$H NMR (CHLOROFORM-d) δ: 8.53 (d, J=4.6 Hz, 1H), 6.83 (d, J=4.9 Hz, 1H), 5.05 (d, J=4.4 Hz, 1H), 4.10 (dd, J=12.3, 2.8 Hz, 1H), 3.51-4.00 (m, 13H), 3.36-3.47 (m, 4H), 3.25-3.36 (m, 2H), 2.78 (dt, J=10.2, 3.8 Hz, 1H), 2.34 (ddd, J=12.3, 6.7, 3.3 Hz, 1H), 2.20 (dt, J=13.0, 6.6 Hz, 2H), 2.01 (dt, J=12.3, 8.3 Hz, 1H), 1.45-1.90 (m, 4H). Calculated for C23H32F3N5O4: 500.2 (M+1). found: 500.3.

Example 24

((3aS,5S,6aR)-5-(((3S,4S)-3-methoxytetrahydro-2H-pyran-4-yl)amino)hexahydro-2H-cyclopenta[b]furan-3a-yl)(4-(6-(trifluoromethyl)pyridin-2-yl)piperazin-1-yl)methanone

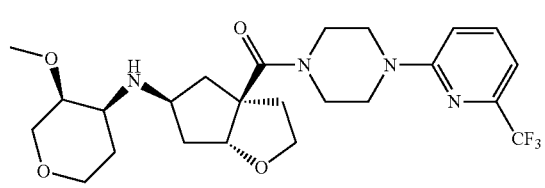 [SMILES: CO[C@@H]1COCC[C@@H]1N[C@@H]1C[C@H]2OCC[C@@]2(C(=O)N2CCN(c3nccc(C(F)(F)F)n3)CC2)C1]

The title compound of Example 24 was made by taking the product of Example 23 Step I and reacting with 2-chloro-6-(trifluoromethyl)pyridine following the procedure described in Example 23, Step J. $^1$H NMR (CHLOROFORM-d) δ: 7.63 (t, J=8.1 Hz, 1H), 7.01 (d, J=7.3 Hz, 1H), 6.81 (d, J=8.6 Hz, 1H), 5.05 (d, J=4.4 Hz, 1H), 4.09 (dd, J=12.3, 3.1 Hz, 1H), 3.96 (qd, J=7.8, 3.5 Hz, 2H), 3.47-3.88 (m, 10H), 3.37-3.47 (m, 4H), 3.26-3.37 (m, 2H), 2.78 (dt, J=10.2, 3.6 Hz, 1H), 2.34 (ddd, J=12.2, 6.7, 3.4 Hz, 1H), 2.13-2.27 (m, 2H), 2.01 (dt, J=12.3, 8.5 Hz, 1H), 1.60-1.88 (m, 4H), 1.54 (ddd, J=13.1, 10.9, 4.8 Hz, 1H). Calculated for C24H33F3N4O4: 499.3 (M+1). found: 499.4.

Example 25

((3aS,5S,6aR)-5-(((3S,4S)-3-methoxytetrahydro-2H-pyran-4-yl)amino)hexahydro-2H-cyclopenta[b]furan-3a-yl)((1S,4S)-5-(4-(trifluoromethyl)pyrimidin-2-yl)-2,5-diazabicyclo[2.2.1]heptan-2-yl)methanone

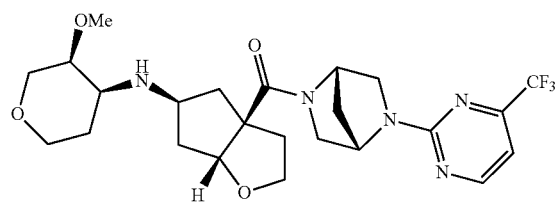 [SMILES: CO[C@@H]1COCC[C@@H]1N[C@@H]1C[C@H]2OCC[C@@]2(C(=O)N2C[C@@H]3C[C@H]2CN3c2nccc(C(F)(F)F)n2)C1]

The title compound of Example 25 was made by taking the product of Example 23, Step E and reacting with (1S,4S)—N-Cbz-2,5-diaza-bicyclo[2.2.1]heptane following the procedure described in Example 23, Step F, and then following the procedures described in Example 23, Steps G through J. $^1$H NMR (CHLOROFORM-d) δ: 8.50 (d, J=4.4 Hz, 1H), 6.83 (d, J=4.6 Hz, 1H), 4.70-5.20 (m, 3H), 4.07 (t, J=10.1 Hz, 1H), 3.83-4.00 (m, 2H), 3.50-3.79 (m, 5H), 3.22-3.48 (m, 7H), 2.79 (d, J=9.5 Hz, 1H), 1.82-2.30 (m, 7H), 1.40-1.82 (m, 4H). Calculated for C24H32F3N5O4: 512.2 (M+1). found: 512.3.

Example 26

((3aS,5S,6aR)-5-(((3S,4S)-3-methoxytetrahydro-2H-pyran-4-yl)amino)hexahydro-2H-cyclopenta[b]furan-3a-yl)((1S,4S)-5-(6-(trifluoromethyl)pyridin-2-yl)-2,5-diazabicyclo[2.2.1]heptan-2-yl)methanone

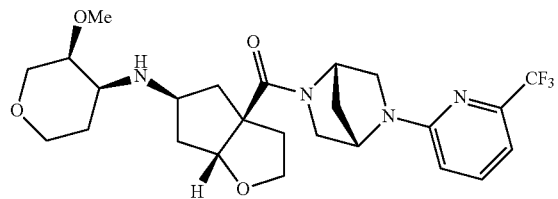 [SMILES: CO[C@@H]1COCC[C@@H]1N[C@@H]1C[C@H]2OCC[C@@]2(C(=O)N2C[C@@H]3C[C@H]2CN3c2cccc(C(F)(F)F)n2)C1]

The title compound of Example 26 was made by taking the product of Example 23, Step E and reacting with (1S,4S)—N-Cbz-2,5-diaza-bicyclo[2.2.1]heptane following the procedure described in Example 23, Step F, then following the procedures described in Example 23, Steps G through I, and then reacting that product with 2-chloro-6-(trifluoromethyl)pyridine following the procedure described in Example 23, Step J. $^1$H NMR (CHLOROFORM-d) δ: 7.56 (t, J=7.9 Hz, 1H), 6.94 (dd, J=7.0, 3.5 Hz, 1H), 6.40-6.57 (m, 1H), 4.65-5.18 (m, 3H), 4.05 (d, J=12.5 Hz, 1H), 3.82-3.99 (m, 2H), 3.61-3.70 (m, 2H), 3.19-3.59 (m, 10H), 2.53-2.85 (m, 1H), 1.84-2.29 (m, 7H), 1.44-1.78 (m, 4H). Calculated for C25H33F3N4O4: 511.3 (M+1). found: 511.2.

Example 27

((3aS,5S,6aR)-5-(((3S,4S)-3-methoxytetrahydro-2H-pyran-4-yl)amino)hexahydro-2H-cyclopenta[b]furan-3a-yl)((1S,4S)-5-(2-(trifluoromethyl)pyrimidin-4-yl)-2,5-diazabicyclo[2.2.1]heptan-2-yl)methanone

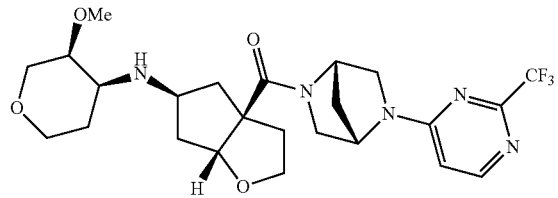 [SMILES: CO[C@@H]1COCC[C@@H]1N[C@@H]1C[C@H]2OCC[C@@]2(C(=O)N2C[C@@H]3C[C@H]2CN3c2ccnc(C(F)(F)F)n2)C1]

The title compound was made by taking the product of Example 23, Step E and reacting with (1S,4S)—N-Cbz-2,5-diaza-bicyclo[2.2.1]heptane following the procedure described in Example 23, Step F, then following the procedures described in Example 23, Steps G through I, and then reacting that product with 4-chloro-2-(trifluoromethyl)pyrimidine following the procedure described in Example 23, Step J. $^1$H NMR (CHLOROFORM-d) δ: 8.27-8.43 (m, 1H), 6.24-6.60 (m, 1H), 5.25-5.48 (m, 1H), 4.50-5.23 (m, 2H), 4.07 (d, J=12.2 Hz, 1H), 3.85-4.02 (m, 2H), 3.58-3.73 (m, 3H), 3.23-3.56 (m, 9H), 2.55-2.91 (m, 1H), 1.86-2.35 (m, 7H), 1.35-1.82 (m, 4H). Calculated for C24H32F3N5O4: 512.2 (M+1). found: 512.2.

Example 28

((3aS,5S,6aR)-5-(((3S,4S)-3-methoxytetrahydro-2H-pyran-4-yl)amino)hexahydro-2H-cyclopenta[b]furan-3a-yl)(4-(2-(trifluoromethyl)pyrimidin-4-yl)piperazin-1-yl)methanone

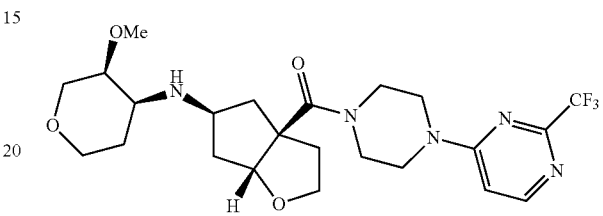

The title compound was made by taking the product of Example 23, Step I and reacting with 4-chloro-2-(trifluoromethyl)pyrimidine following the procedure described in Example 23, Step J. $^1$H NMR (CHLOROFORM-d) δ: 8.37 (d, J=6.4 Hz, 1H), 6.63 (d, J=6.1 Hz, 1H), 5.04 (d, J=4.6 Hz, 1H), 4.10 (dd, J=12.2, 2.7 Hz, 1H), 3.90-4.02 (m, 2H), 3.47-3.90 (m, 10H), 3.36-3.46 (m, 4H), 3.26-3.36 (m, 2H), 2.77 (dt, J=10.1, 3.7 Hz, 1H), 2.32 (ddd, J=12.1, 6.7, 3.4 Hz, 1H), 2.19 (td, J=12.8, 6.2 Hz, 2H), 1.95-2.08 (m, 1H), 1.59-1.86 (m, 4H), 1.54 (ddd, J=13.1, 11.1, 4.9 Hz, 1H). Calculated for C23H32F3N5O4: 500.2 (M+1). found: 500.2.

Example 29

((3aS,5S,6aR)-5-((3-methoxytetrahydro-2H-pyran-4-yl)amino)hexahydro-2H-cyclopenta[b]furan-3a-yl)(3-(trifluoromethoxy)-7,8-dihydro-1,6-naphthyridin-6(5H)-yl)methanone

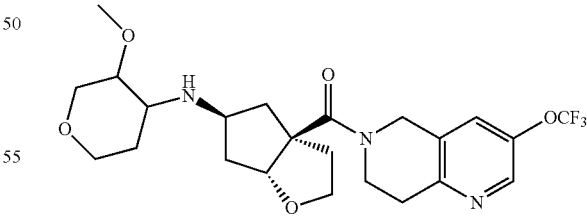

The title compound was prepared from reaction of the product of Example 23, Step E and 3-(trifluoromethoxy)-5,6,7,8-tetrahydro-1,6-naphthyridine following the procedure described in Example 1, Step C, and then following procedures described in Example 1, Steps G and H. $^1$H NMR (CHLOROFORM-d) δ: 8.40 (br. s., 1H), 7.35 (br. s., 1H), 5.05 (t, J=4.3 Hz, 1H), 4.74 (br. s., 2H), 3.78-4.16 (m, 5H), 3.48-3.74 (m, 2H), 3.24-3.46 (m, 6H), 3.08 (br. s., 2H), 2.81

(t, J=9.3 Hz, 1H), 2.17-2.40 (m, 3H), 1.91-2.12 (m, 3H), 1.53-1.88 (m, 3H). Calculated for C23H30F3N3O5: 486.2 (M+1). found: 486.1.

Example 30

((3aS,5S,6aR)-5-((3S,4S)-3-methoxytetrahydro-2H-pyran-4-ylamino)hexahydro-2H-cyclopenta[b]furan-3a-yl)(3-(trifluoromethyl)-7,8-dihydro-1,6-naphthyridin-6(5H)-yl)methanone succinate

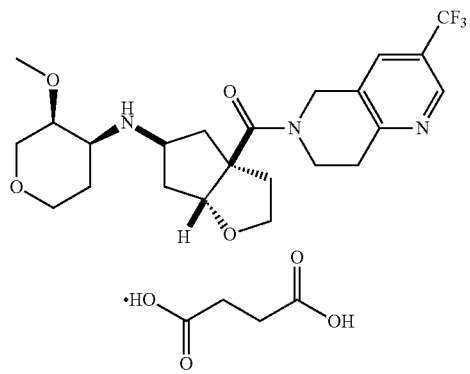

Step A (1R,4S)-methyl 4-aminocyclopent-2-enecarboxylate hydrochloride

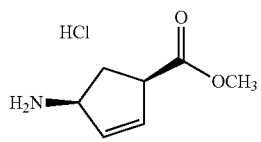

A solution of (1S,4R)-2-azabicyclo[2.2.1]hept-5-en-3-one (725 g, 6.64 mol) in MeOH (2.2 L) was stirred in an ice bath to 0° C. Thionyl chloride (290 mL, 3.99 mol) was added dropwise over a 2.25 h period while keeping the temperature below 13° C. The reaction was stirred for 2 h at 8° C. Isopropyl acetate (16.3 L) was added and the slurry stirred for 1 h. The solid was filtered with a Buchner funnel, washed with isopropylacetate (~1 L) and the solid was allowed to air-dry overnight to afford an off-white solid. $^1$H NMR (400 MHz, DMSO-d$_6$) δ=8.44 (br. s., 3H), 5.99-6.16 (m, 1H), 5.90 (dt, J=2.4, 5.3 Hz, 1H), 4.17 (br. s., 1H), 3.56-3.79 (m, 4H), 2.56 (m, 1H), 1.84-2.04 (m, 1H).

Step B (1R,4S)-methyl 4-(tert-butoxycarbonylamino)cyclopent-2-enecarboxylate

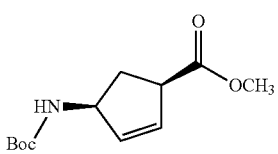 [SMILES: COC(=O)[C@H]1C=C[C@@H](NC(=O)OC(C)(C)C)C1]

A solution of the product of Step A (551 g, 3.10 mol), CH$_2$Cl$_2$ (15.5 L), and di-t-butyldicarbonate (684 g, 3.10 mol) was stirred to 2° C. with an ice bath. Triethylamine (435 mL, 3.12 mol) was added over 1 h 5 min at a rate not to exceed 3° C. The reaction was stirred for 2 h. The volatiles were evaporated, the crude product was suspended in a mixture of EtOAc and heptane, the solid was filtered through silica gel, and washed with additional EtOAc in heptane. The organics were evaporated and afforded the product of Step B as a brown solid. $^1$H NMR (400 MHz) δ=5.87 (d, J=6.4 Hz, 2H), 4.85-5.02 (m, 1H), 4.72-4.85 (m, 1H), 3.72 (s, 3H), 3.47 (m, 1H), 2.51 (d, J=13.9 Hz, 1H), 1.88 (s, 1H), 1.44 (s, 10H).

Step C (1,1-dimethylethyl)(2-iodoethoxy)dimethylsilane

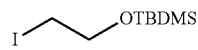

Iodoethanol (2.68 kg, 15.4 mol), CH$_2$Cl$_2$ (12 L) and imidizaole (1.556 kg, 22.63 mol) were chilled in an ice bath. A solution of t-butyldimethylchlorosilane (2.536 kg, 16.32 mol) in CH$_2$Cl$_2$ (2.5 L) was added to the reaction over a 2 h period. The resulting white suspension was allowed to warm to rt over an 18 h. The reaction was worked up by washing with water and brine). The organic layer was dried (MgSO$_4$) and evaporated under reduced pressure to provide the product of Step C as a light yellow oil. $^1$H NMR (400 MHz, CDCl$_3$) δ=3.75 (t, J=7.0 Hz, 2H), 3.11 (t, J=7.0 Hz, 2H), 0.77-0.89 (m, 10H), 0.00 (s, 6H).

Step D (1S,4S)-methyl 4-(tert-butoxycarbonylamino)-1-(2-(tert-butyldimethylsilyloxy)ethyl)cyclopent-2-enecarboxylate

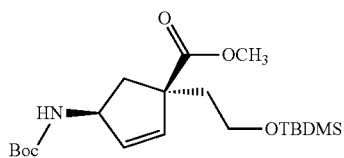 [SMILES: COC(=O)[C@@]1(CCO[Si](C)(C)C(C)(C)C)C=C[C@@H](NC(=O)OC(C)(C)C)C1]

To a −70° C. solution of LiHMDS in THF (1M, 6.97 L, 6.97 mol) was added a solution of the product of Step B (763.5 g, 3.16 mol) in THF (800 mL) over a 2 h period while keeping the temperature at or below −68° C. The resulting solution was stirred for 45 min at −68° C. A solution of the product of Step C (1.267 kg, 4.426 mol) in THF (800 mL) was added over 1 h 50 min period while maintaining a temperature of ~−66° C. The reaction was stirred at ~−66° C. for 45 min. The reaction was warmed to −15° C. and worked up by addition to mixture of aqueous HCl and ice. The mixture was extracted with toluene, the organic layer was washed with water, brine and dried over MgSO$_4$. The organic layer was concentrated and purified on silica gel using a mixture of EtOAc in heptanes to provide the product of Step D as a clear oil. $^1$H NMR (400 MHz, CHLOROFORM-d) d=5.69-5.86 (m, 2H), 4.79-4.93 (m, 1H), 4.68-4.80 (m, 1H), 3.67 (s, 3H), 3.53-3.62 (m, 2H), 2.16-2.30 (m, 1H), 2.04-2.16 (m, 2H), 1.70-1.81 (m, 1H), 1.41 (s, 9H), 0.78-0.91 (m, 13H), 0.00 (s, 6H).

Step E tert-Butyl (5S,7S)-1-oxo-2-oxaspiro[4.4]non-8-en-7-ylcarbamate

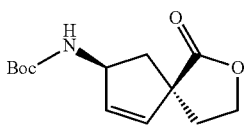

To a solution of the product of Step D (1149 g, 2.875 mol) and THF (5.75 L) was added TBAF (1M in THF, 2.875 L) over ~1 h. The reaction was stirred for 1 h at rt, and diluted with EtOAc. The organic layer was washed with brine, diluted with heptanes and the organic layer was further washed with water and brine. The organic layer was evaporated, the crystallized product was filtered, and washed with heptanes to provide the product of Step E as a white solid. $^1$H NMR (400 MHz, CHLOROFORM-d) d=5.86-5.98 (m, 3H), 5.67 (d, J=5.4 Hz, 3H), 5.03-5.20 (m, 2H), 4.76-4.87 (m, 3H), 4.28 (t, J=7.0 Hz, 5H), 2.08-2.31 (m, 8H), 1.99 (d, J=2.4 Hz, 3H), 1.34 (s, 25H).

Step F tert-butyl ((1S,4S)-4-(2-hydroxyethyl)-4-(hydroxymethyl)cyclopent-2-en-1-yl)carbamate

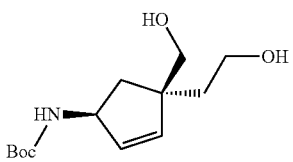 [SMILES: CC(C)(C)OC(=O)N[C@@H]1C=C[C@@](CO)(CCO)C1]

To a solution of the product of Step E (255.9 g, 1.01 mol) and MeOH (2 L) chilled to 2° C. was added NaBH$_4$ (75 g) over ~2.5 h. The reaction was quenched by addition of aqueous NH$_4$Cl, concentrated under reduced pressure and the mixture was diluted with water and EtOAc. The layers were separated and the aqueous layer was extracted with additional EtOAc. The combined organics were washed with brine, dried (MgSO$_4$) and evaporated to give the product of Step F as a thick oil. $^1$H NMR (400 MHz, CHLOROFORM-d) d=5.74 (d, J=2.0 Hz, 2H), 4.81-4.92 (m, 1H), 4.67-4.79 (m, 1H), 3.71 (t, J=6.1 Hz, 2H), 3.50 (d, J=11.7 Hz, 2H), 2.14-2.28 (m, 2H), 1.70 (td, J=1.6, 6.2 Hz, 4H), 1.52-1.60 (m, 1H), 1.44 (s, 9H)

Step G tert-butyl (3 aR,5S,6S,6aS)-6-bromo-3a-(hydroxymethyl)hexahydro-2H-cyclopenta[b]furan-5-ylcarbamate

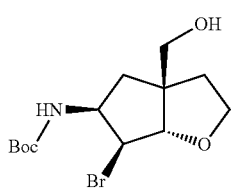 [SMILES: CC(C)(C)OC(=O)N[C@H]1C[C@]2(CO)CCO[C@@H]2[C@H]1Br]

To a chilled solution of the product of Step F (343.60 g) in EtOAc (4 L) was added N-bromosuccinimide (237.60 g) followed by stirring at rt for 18 h. To the mixture was added water (5 mL) and the reaction heated to 60° C. for 30 min. The reaction was filtered, the filtrate was washed with aqueous sodium thiosulfate until the organic layer was negative for peroxides. The organic layer was washed with aqueous Na$_2$CO$_3$ (10%), dried (Na$_2$SO$_4$) and the reaction was concentrated under reduced pressure. Near the end of the concentration, heptane (1.2 L) was added, and the product was collected by filtration to provide the product of Step G. $^1$H NMR (400 MHz, CHLOROFORM-d) δ=4.78-4.91 (m, 1H), 4.41 (br. s., 1H), 4.31 (s, 2H), 3.88-3.98 (m, 1H), 3.61-3.77 (m, 3H), 2.08-2.24 (m, 1H), 1.82 (m, 2H), 1.60-1.70 (t, 1H), 1.45 (s, 9H)

Step H tert-Butyl (3aR,5S,6aR)-3a-(hydroxymethyl)hexahydro-2H-cyclopenta[b]furan-5-ylcarbamate

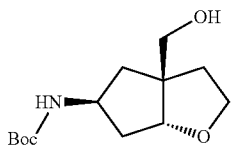 [SMILES: CC(C)(C)OC(=O)N[C@@H]1C[C@H]2OCC[C@@]2(CO)C1]

A solution of the product of Step G (83 g, 0.245 mol), 10% Pd on C (12.5 g), triethylamine (69 mL, 0.49 mol, 2 eq.) in EtOAc (830 mL) was shaken on a PAAR hydrogenator at 40 psi for 3.5 h until the pressure remained constant. The reaction was filtered with celite, the filter cake was washed with EtOAc, and the collected filtrate was washed with aqueous HCl (1N), brine, dried (Na$_2$SO$_4$) and concentrated under reduced pressure to give the product of Step H. $^1$H NMR (400 MHz, CHLOROFORM-d) d=4.60-4.73 (m, 1H), 4.06-4.24 (m, 3H), 3.84-3.93 (m, 1H), 3.52-3.67 (m, 4H), 2.12-2.21 (m, 1H), 1.98-2.04 (m, 1H), 1.90 (br. s., 3H), 1.70-1.78 (m, 1H), 1.46-1.56 (m, 3H), 1.44 (s, 11H).

Step I (3aS,5S,6aR)-5-(tert-Butoxycarbonylamino)hexahydro-2H-cyclopenta[b]furan-3a-carboxylic acid

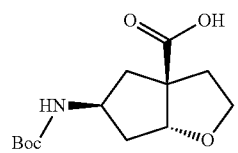 [SMILES: CC(C)(C)OC(=O)N[C@@H]1C[C@H]2OCC[C@@]2(C(=O)O)C1]

To an ice-cold solution of the product of Step H (426 g, 1.57 mol) and acetone (8.1 L) was added Jones reagent (710 mL) over 1 h 20 min. The resulting suspension was stirred at rt for 1 h, after which isopropyl alcohol (40 mL) was added, and the reaction stirred for 25 min at rt. Water was added, and the water/acetone was decanted off and evaporated. The insoluble material was dissolved separately in water and extracted with CH$_2$Cl$_2$. The green water/acetone concentrate was extracted with CH$_2$Cl$_2$ and the combined organic extracts were washed with brine, diluted with water and EtOAc and the organic layer was dried with Na$_2$SO$_4$. The organic layer was filtered, concentrated and the product was crystallized from MeCN, and the product of Step I was isolated by filtration as a white solid. $^1$H NMR (400 MHz, DMSO-d$_6$) δ=12.39-12.59 (m, 1H), 6.85-7.02 (m, 1H), 4.28 (d, J=5.4 Hz, 1H), 3.89-3.97 (m, 1H), 3.79-3.85 (m, 1H), 3.43-3.51 (m, 1H), 3.30-3.36 (m, 1H), 2.35-2.42 (m, 1H), 1.90 (d, J=11.0 Hz, 1H), 1.59-1.70 (m, 1H), 1.42-1.50 (m, 1H), 1.37 (s, 9H). Elemental anal calc for C13H21NO5: C, 57.55; H, 7.80; N, 5.16. Found: C, 57.34; H, 8.18; N, 5.08 mp: 147.4-149.1° C.

Step J tert-Butyl (3 aS,5S,6aR)-3a-(3-(trifluoromethyl)-5,6,7,8-tetrahydro-1,6-naphthyridine-6-carbonyl)hexahydro-2H-cyclopenta[b]furan-5-ylcarbamate

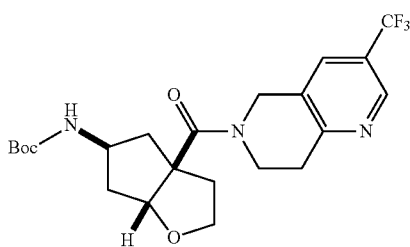 [SMILES: CC(C)(C)OC(=O)N[C@@H]1C[C@H]2OCC[C@@]2(C(=O)N2CCc3ncc(C(F)(F)F)cc3C2)C1]

To a solution of the product of Step I (596.8 g, 1.91 mol) in CH₂Cl₂ was added EDC (98.5% pure, 559 g, 2.87 mol) and HOBt (449 g, 3.26 mol) and the suspension was stirred for 15 min at rt. 3-(Trifluoromethyl)-5,6,7,8-tetrahydro-1,6-naphthyridine-2HCl (790 g, 2.87 mol) was added, followed by DIEA (1.7 L, 9.65 mol) by addition over 45 min. The reaction was stirred at rt for 20 h. The reaction was partitioned between saturated aqueous NaHCO₃ and CH₂Cl₂. The organic layer was removed, the aqueous layer diluted with water and the aqueous layer extracted with CH₂Cl₂. The combined organics were washed with ½ saturated brine, dried over Na₂SO₄, and concentrated under reduced pressure. The resulting crude product was purified by chromatography using EtOAc in heptane to provide the product of Step J as a thick orange foam. ¹H NMR (400 MHz, CHLOROFORM-d) d=8.72 (s, 1H), 7.71 (s, 1H), 5.00-5.08 (m, 1H), 4.77 (br. s., 2H), 4.61-4.68 (m, 1H), 4.21-4.34 (m, 1H), 3.96-4.05 (m, 1H), 3.85-3.93 (m, 2H), 3.71 (s, 1H), 3.13 (br. s., 2H), 2.38-2.48 (m, 1H), 2.28-2.33 (m, 1H), 2.20-2.26 (m, 1H), 2.09-2.17 (m, 1H), 1.75-1.85 (m, 1H), 1.61-1.70 (m, 1H), 1.40 (s, 9H).

Step K ((3aS,5S,6aR)-5-Aminohexahydro-2H-cyclopenta[b]furan-3a-yl)(3-(trifluoromethyl)-7,8-dihydro-1,6-naphthyridin-6(5H)-yl)methanone dihydrochloride

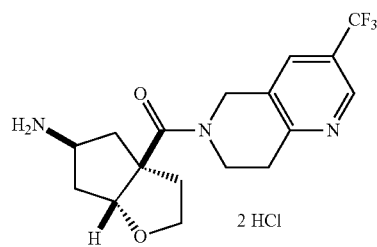 [SMILES: N[C@@H]1C[C@H]2OCC[C@@]2(C(=O)N2CCc3ncc(C(F)(F)F)cc3C2)C1]

A solution of the product of Step J (773 g, 1.61 mol) and HCl in MeOH (~1.25 M, 14.25 L, 17.81 mol) was heated to 60° C. and after the vigorous bubbling ceased, the reaction was concentrated under reduced pressure. Isopropyl alcohol was added, the contents were evaporated to near-dryness and heptane was added to the flask. The contents were filtered, washed with some isopropyl alcohol/heptane (ad lib) and the solid was dried in air, followed by drying in a vacuum oven to afford the product of Step K as an ivory solid. A small sample of the product was converted to the free-based using 1,2-dichloroethane/aqueous 3M NaOH for further analysis by NMR and elemental analysis. Elemental analysis calc for $C_{17}H_{20}F_3N_3O_2 \times 1.6\ H_2O$: C, 53.14; H, 6.09; F, 14.83; N, 10.93; $H_2O$=7.50. Found: C, 52.30; H, 5.78; F, 14.62; N, 10.51; KF=7.28. ¹H NMR (400 MHz, CHLOROFORM-d) δ=8.72 (s, 1H), 7.70 (br. s., 1H), 5.06 (d, J=4.9 Hz, 1H), 4.78 (s, 2H), 3.85-4.03 (m, 3H), 3.71-3.75 (m, 2H), 3.59-3.70 (m, 2H), 3.08-3.19 (m, 2H), 2.24-2.38 (m, 2H), 2.19 (dd, J=5.7, 13.3 Hz, 1H), 2.08 (br. s., 1H), 1.62-1.78 (m, 1H), 1.46-1.57 (m, 1H), 1.42 (br. s., 3H)

Step L ((3aS,5S,6aR)-5-((3S,4S)-3-Methoxytetrahydro-2H-pyran-4-ylamino)hexahydro-2H-cyclopenta[b]furan-3a-yl)(3-(trifluoromethyl)-7,8-dihydro-1,6-naphthyridin-6(5H)-yl)methanone

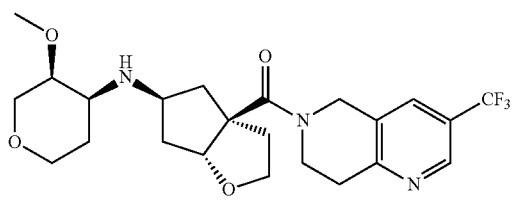 [SMILES: CO[C@@H]1COCC[C@@H]1N[C@@H]1C[C@H]2OCC[C@@]2(C(=O)N2CCc3ncc(C(F)(F)F)cc3C2)C1]

To a mixture of the product of Step K (the free base) (619.7 g, 1.74 mol) in 1,2-dichloroethane/CH₂Cl₂ (~10 L) was added acetic acid (glacial, 180 mL) and the mixture was cooled to 16° C. Solid Na(OAc)₃BH (463 g, 2.18 mol) was added and the suspension was stirred for 5-10 min. A solution of (R)-3-methoxydihydro-2H-pyran-4(3H)-one (prepared as described in Intermediate 1, 213 g, 1.63 mol) in 1,2-dichloroethane (1.75 L) was added over 20 min and the resulting mixture was stirred at rt overnight. Additional acetic acid, (R)-3-methoxytetrahydro-4H-pyran-4-one (28 g) and Na(AcO)₃BH were added until TLC showed the reaction was complete. The reaction was quenched with saturated aqueous NaHCO₃, the organic layer was separated and the aqueous layer was back-extracted with CH₂Cl₂. The combined organic layers were washed with brine, dried (Na₂SO₄) and evaporated under reduced pressure. Purification was affected by chromatography with MeOH (7N NH₃) in CH₂Cl₂. The collected enriched isomer was further purified using chiral chromatography on chiralpak AD column using a mixture of heptanes/EtOH/isopropyl alcohol to provide the product of Step L.

¹H NMR (CHLOROFORM-d) δ: 8.72 (s, 1H), 7.70 (br. s., 1H), 5.05 (d, J=4.6 Hz, 1H), 4.70-4.87 (m, 2H), 4.09 (dd, J=12.5, 2.7 Hz, 1H), 3.81-4.03 (m, 4H), 3.62-3.71 (m, 1H), 3.50-3.62 (m, 1H), 3.35-3.46 (m, 4H), 3.24-3.35 (m, 2H), 3.14 (t, J=4.9 Hz, 2H), 2.71-2.82 (m, 1H), 2.14-2.43 (m, 3H), 1.99-2.13 (m, 1H), 1.46-1.86 (m, 5H). Calculated for C24H31F3N2O4: 470.2 (M+1). found: 470.1.

Step M ((3 aS,5S,6aR)-5-((3S,4S)-3-methoxytetrahydro-2H-pyran-4-ylamino)hexahydro-2H-cyclopenta[b]furan-3a-yl)(3-(trifluoromethyl)-7,8-dihydro-1,6-naphthy-ridin-6(5H)-yl)methanone succinate

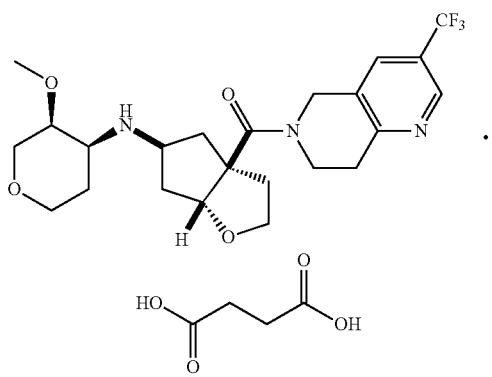

A solution of Example 30, Step L (608 g, 1.18 mol) in MeOH (6 L) was warmed to 40° C. until dissolved. Succinic acid (141.9 g, 1.20 mol) was added and the suspension was warmed to 50° C. which caused everything to dissolve. Darco G-60 charcoal (80 g) was added and the contents swirled for 20 min. The mixture was filtered through Celite, washed with MeOH, and the solvent was evaporated under reduced pressure to provide the title compound (i.e., the succinate salt) as an amorphous foam. The resulting foam was dissolved completely in MIBK (5 L, degassed) at reflux, the heating was stopped and the solution was allowed to cool. The solution was seeded at 104° C. with crystalline material, prepared as described in Example 52, and the solution was cooled to 38° C. over 4 h. The suspension was chilled to 4° C., filtered, washed with ice-cold 100 mL MIBK and the solid was allowed to dry under a positive nitrogen stream (protected from light) overnight. After some light milling, the product of Step M was collected as a white solid. $^1$H NMR (400 MHz, MeOD) δ=8.72 (s, 1H), 8.04-8.12 (m, 1H), 4.97 (d, J=4.4 Hz, 1H), 4.94 (s, 3H), 4.86 (s, 2H), 4.18-4.28 (m, 1H), 3.98 (d, J=11.7 Hz, 4H), 3.74-3.88 (m, 1H), 3.62-3.73 (m, 1H), 3.28-3.58 (m, 8H), 3.12-3.23 (m, 2H), 2.58-2.68 (m, 1H), 2.37-2.44 (m, 1H), 2.28-2.36 (m, 1H), 1.88 (m, 4H). Elemental Analysis calc for C27H36F3N3O8×0.2 H2O: C, 54.85; H, 6.21; F, 9.64; N, 7.11; KF 0.61. Found: C, 55.17; H, 6.07; F, 9.99; N, 7.11; KF, 0.64.

Example 31

((3aS,5S,6aR)-5-(4-phenylpiperidin-1-yl)hexahydro-2H-cyclopenta[b]furan-3a-yl)(3-(trifluoromethyl)-7,8-dihydro-1,6-naphthyridin-6(5H)-yl)methanone

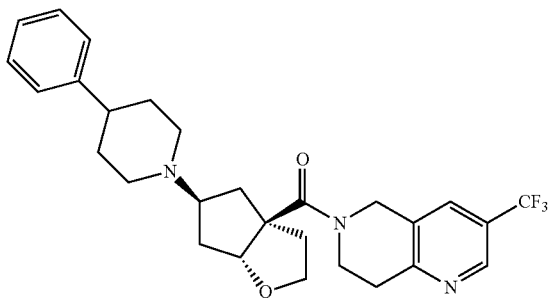 [SMILES: O=C(N1CCc2ncc(C(F)(F)F)cc2C1)[C@@]12CCO[C@@H]1C[C@@H](N1CCC(c3ccccc3)CC1)C2]

Step A 1-((3aS,5S,6aR)-3a-(3-(trifluoromethyl)-5,6,7,8-tetrahydro-1,6-naphthyridine-6-carbonyl)hexahydro-2H-cyclopenta[b]furan-5-yl)piperidin-4-one

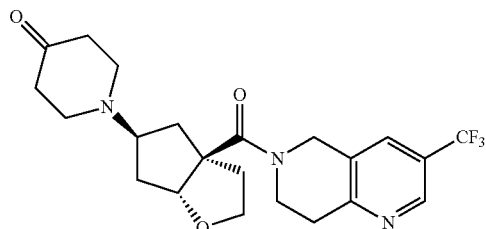

To a suspension of sodium carbonate (2.2 g, 20.7 mmol, 5 eq) in methanol (70 mL) at 60° C. were added solutions of the product of Example 1, Step G (1.77 g, 4.14 mmol, 1 eq) in methanol (35 mL) 1,5-dichloropentan-3-one (0.74 g, 4.55 mmol, 1.1 eq) in methanol (35 mL) simultaneously over 1 hour. After stirring 1 hr at 60° C., the suspension was cooled to rt, water was added, the methanol was concentrated, and the aqueous extracted with DCM, dried over MgSO4 and concentrated. Purification by chromatography eluting with 2 to 6% MeOH/DCM afforded the title compound of Step A. Calculated for C22H26F3N3O3: 438.2 (M+1). found: 438.2.

Step B 1-((3 aS,5S,6aR)-3a-(3-(trifluoromethyl)-5,6,7,8-tetrahydro-1,6-naphthyridine-6-carbonyl)hexahydro-2H-cyclopenta[b]furan-5-yl)-1,2,3,6-tetrahydropyri-din-4-yl trifluoromethanesulfonate

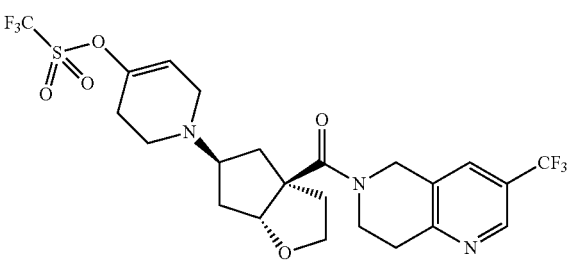 [SMILES: O=C(N1CCc2ncc(C(F)(F)F)cc2C1)[C@@]12CCO[C@@H]1C[C@@H](N1CC=C(OS(=O)(=O)C(F)(F)F)CC1)C2]

To the product of Step A (1.06 g, 2.42 mmol, 1 eq) in THF (30 mL) at −78° C. under N2 was added KHMDS (6.8 mL of a 0.5 M solution in toluene, 3.39 mmol, 1.4 eq), the solution turned purple. After 15 minutes, a solution of N-phenyl-bis (trifluoromethanesulfonimide) (1.21 g, 3.39 mmol, 1.4 eq) in THF (10 mL) was added and the yellow solution stirred 1 hour at −78° C. Saturated NH4Cl was added, the aqueous extracted with ethyl acetate, dried over MgSO4 and concentrated. Purification by column chromatography (80 g) eluting with 3 to 6% MeOH/DCM afforded the title compound of Step B. Calculated for C23H25F6N3O5S: 570.1 (M+1). found: 570.0.

Step C ((3aS,5S,6aR)-5-(4-phenyl-5,6-dihydropyridin-1 (2H)-yl)hexahydro-2H-cyclopenta[b]furan-3a-yl)(3-(trifluoromethyl)-7,8-dihydro-1,6-naphthyridin-6 (5H)-yl)methanone

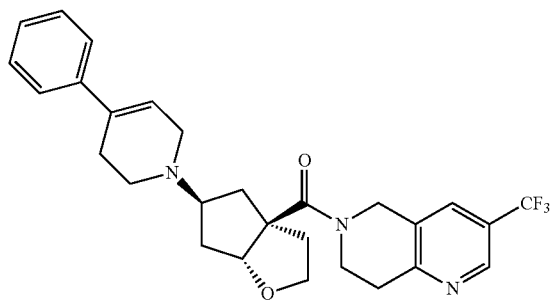 [SMILES: O=C(N1CCc2ncc(C(F)(F)F)cc2C1)[C@@]12CCO[C@@H]1C[C@@H](N1CC=C(c3ccccc3)CC1)C2]

A solution of the product of Step B (50 mg, 0.09 mmol, 1 eq), phenylboronic acid (22 mg, 0.18 mmol, 2 eq), (Ph₃P)₄Pd (10 mg, 0.009 mmol, 0.1 eq) and 2 M Na₂CO₃ (0.1 mL) in dimethoxyethane (1 mL) under N₂ was warmed to 80 C in a screw-top vial overnight. The solution was cooled to rt, and concentrated. Purification by column chromatography (4 g) eluting with 50 to 100% ethyl acetate/heptane afforded the title compound of Step C. Calculated for C28H30F3N3O2: 498.2 (M+1). found: 498.3.

Step D ((3aS,5S,6aR)-5-(4-phenylpiperidin-1-yl)hexahydro-2H-cyclopenta[b]furan-3a-yl)(3-(trifluoromethyl)-7, 8-dihydro-1,6-naphthyridin-6(5H)-yl)methanone

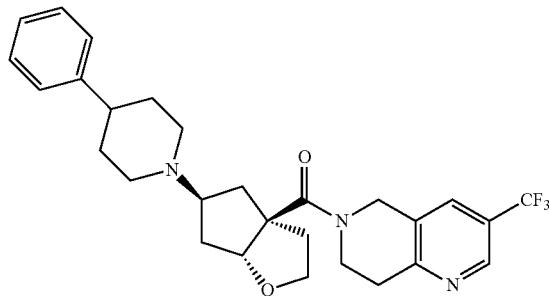 [SMILES: O=C(N1CCc2ncc(C(F)(F)F)cc2C1)[C@@]12CCO[C@@H]1C[C@@H](N1CCC(c3ccccc3)CC1)C2]

A suspension of the product of Step D (24 mg, 0.046 mmol, 1 eq) and 5% Pd/C (20 mg) in ethanol (3 mL) was placed under a balloon of hydrogen gas overnight. The solution was filtered through celite and concentrated. Purification by column chromatography (4 g) eluting with 2 to 6% MeOH/DCM afforded the title compound. ¹H NMR (CHLOROFORM-d) δ: 8.71 (s, 1H), 7.70 (br. s., 1H), 7.27-7.33 (m, 2H), 7.15-7.24 (m, 3H), 5.06 (d, J=4.5 Hz, 1H), 4.78 (br. s., 2H), 4.02 (td, J=8.1, 3.5 Hz, 1H), 3.81-3.96 (m, 2H), 3.61-3.73 (m, 1H), 2.90-3.21 (m, 5H), 2.45-2.57 (m, 1H), 2.22-2.32 (m, 2H), 2.08-2.15 (m, 3H), 1.99 (br. s., 2H), 1.65-1.89 (m, 5H). Calculated for C28H32F3N3O2: 500.2 (M+1). found: 500.3.

Example 32

3-(1-((3aS,5S,6aR)-3a-(3-(trifluoromethyl)-5,6,7,8-tetrahydro-1,6-naphthyridine-6-carbonyl)hexahydro-2H-cyclopenta[b]furan-5-yl)piperidin-4-yl)benzoic acid

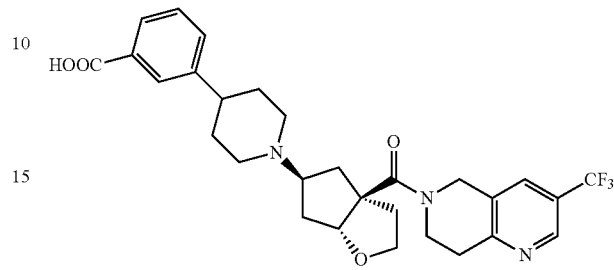

The title compound of Example 32 was made by taking the product of Example 31, Step B and reacting with 3-carboxyphenylboronic acid following the procedure described in Example 31, Step C, then following the procedures described in Example 31, Step D. Calculated for C29H32F3N3O4: 544.2 (M+1). found: 544.0.

Example 33

((3aS,5S,6aR)-5-(4-(3-methoxyphenyl)piperidin-1-yl)hexahydro-2H-cyclopenta[b]furan-3a-yl)(3-(trifluoromethyl)-7,8-dihydro-1,6-naphthyridin-6(5H)-yl)methanone

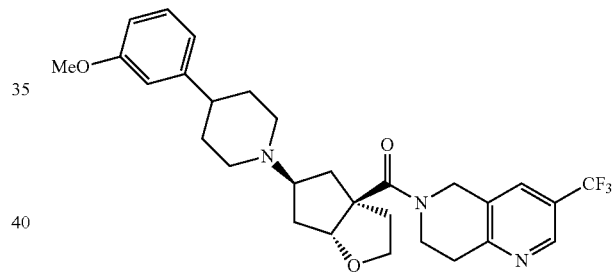

The title compound of Example 33 was made by taking the product of Example 31, Step B and reacting with 3-methoxyphenylboronic acid following the procedure described in Example 31, Step C, then following the procedures described in Example 31, Step D. Calculated for C29H34F3N3O3: 530.3 (M+1). found: 530.3.

Example 34

4-(1-((3aS,5S,6aR)-3a-(3-(trifluoromethyl)-5,6,7,8-tetrahydro-1,6-naphthyridine-6-carbonyl)hexahydro-2H-cyclopenta[b]furan-5-yl)piperidin-4-yl)benzoic acid

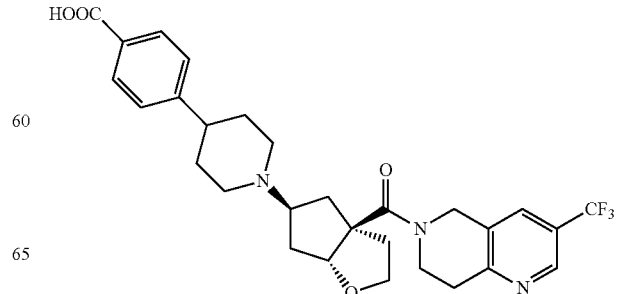

The title compound of Example 34 was made by taking the product of Example 31, Step B and reacting with 4-benzyloxycarbonylphenylboronic acid following the procedure described in Example 31, Step C, then following the procedures described in Example 31, Step D. $^1$H NMR (CHLOROFORM-d) δ: 8.68 (s, 1H), 7.79-7.88 (m, J=8.1 Hz, 2H), 7.60 (br. s., 1H), 7.09-7.21 (m, J=8.6 Hz, 2H), 5.01 (d, J=4.0 Hz, 1H), 4.67-4.78 (m, 1H), 4.51-4.67 (m, 1H), 4.02 (br. s., 1H), 3.63-3.96 (m, 3H), 3.34-3.54 (m, 3H), 3.23 (d, J=11.6 Hz, 1H), 3.09 (br. s., 1H), 2.56-2.70 (m, 2H), 2.27-2.50 (m, 5H), 1.84-2.20 (m, 6H). Calculated for C29H32F3N3O4: 544.2 (M+1). found: 544.2.

Example 35

((3aS,5S,6aR)-5-(((3S,4S)-3-methoxytetrahydro-2H-pyran-4-yl)amino)hexahydro-2H-cyclopenta[b]furan-3a-yl)(6-(trifluoromethyl)-2H-benzo[e][1,3]oxazin-3(4H)-yl)methanone

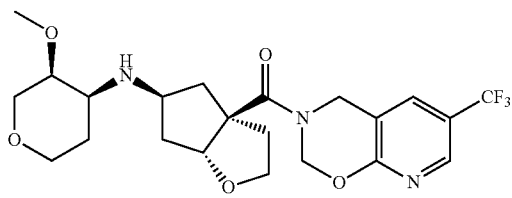 [SMILES: CO[C@@H]1COCC[C@@H]1N[C@@H]1C[C@H]2OCC[C@@]2(C(=O)N2COc3ncc(C(F)(F)F)cc3C2)C1]

Step A tert-butyl ((3aS,5S,6aR)-3a-((2-(tert-butoxy)-5-(trifluoromethyl)benzyl)carbamoyl)hexahydro-2H-cyclopenta[b]furan-5-yl)carbamate

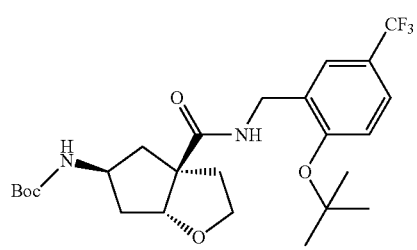 [SMILES: CC(C)(C)OC(=O)N[C@@H]1C[C@H]2OCC[C@@]2(C(=O)NCc2cc(C(F)(F)F)ccc2OC(C)(C)C)C1]

The product of Step A was prepared from the reaction of the product of Example 23, Step E and (2-(tert-butoxy)-5-(trifluoromethyl)phenyl)methanamine prepared according to procedures in ACS Med. Chem. Letters 2010, 1, 14 following the procedure from Example 1, Step C. Calculated for C25H35F3N2O5: 523.2 (M+23). found: 523.2.

Step B (3aS,5S,6aR)-5-amino-N-(2-hydroxy-5-(trifluoromethyl)benzyl)hexahydro-2H-cyclopenta[b]furan-3a-carboxamide dihydrochloride

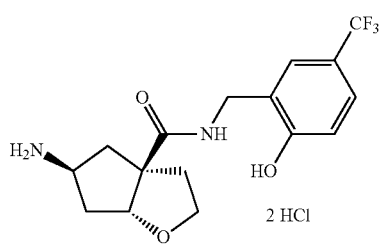 [SMILES: N[C@@H]1C[C@H]2OCC[C@@]2(C(=O)NCc2cc(C(F)(F)F)ccc2O)C1]

A solution of the product of Step A (11.07 g, 20.57 mmol, 1 eq) in methanol (60 mL) and solution of HCl in methanol (82 mL of 1.25 M solution, 103 mmol, 5 eq) was heated to 55° C. for 2.5 days. The solution was concentrated to give the product of step B. Calculated for C16H19F3N2O3: 345.1 (M+1). found: 345.3.

Step C (3aS,5S,6aR)-5-(1,3-dioxoisoindolin-2-yl)-N-(2-hydroxy-5-(trifluoromethyl)benzyl)hexahydro-2H-cyclopenta[b]furan-3a-carboxamide

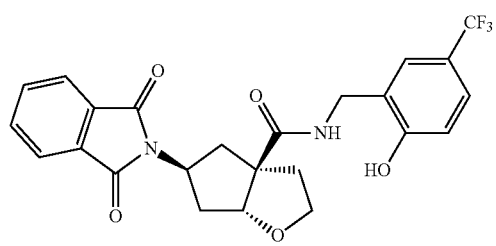 [SMILES: O=C1c2ccccc2C(=O)N1[C@@H]1C[C@H]2OCC[C@@]2(C(=O)NCc2cc(C(F)(F)F)ccc2O)C1]

A solution of the product of Step B (8.58 g, 18.74 mmol, 1 eq), phthalic anhydride (5.55 g, 37.5 mmol, 2 eq) and DIEA (11.3 mL, 55.6 mmol, 3.5 eq) in chloroform (150 mL) was heated to 70° C. for 2 hours. The solution was cooled to rt and carbonyl diimidazole (2.24 g 13.82 mmol, 3 eq) was added and the solution heated to 60° C. for 2 hours. The solution was cooled to rt, 1 N HCl was added, the aqueous extracted with DCM, the organics combined, dried over MgSO4 and concentrated. Purification by chromatography (200 g column) eluting with 30 to 60 to 80% EA/heptane afforded the product of Step C. Calculated for C24H21F3N2O5: 474.1 (M+1). found: 475.1.

Step D 2-((3aS,5S,6aR)-3a-(6-(trifluoromethyl)-3,4-dihydro-2H-benzo[e][1,3]oxazine-3-carbonyl)hexahydro-2H-cyclopenta[b]furan-5-yl)isoindoline-1,3-dione

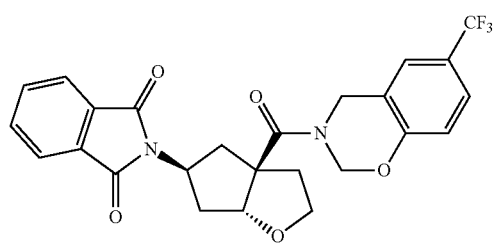 [SMILES: O=C1c2ccccc2C(=O)N1[C@@H]1C[C@H]2OCC[C@@]2(C(=O)N2COc3ccc(C(F)(F)F)cc3C2)C1]

A solution of the product of Step C (7.97 g, 15.5 mmol, 1 eq), paraformaldehyde (9.28 g, 310 mmol, 20 eq) and p-toluenesulfonic acid hydrate (2.94 g, 15.5 mmol, 1 eq) in toluene (300 mL) was heated to 130° C. for 18 hours in a flask equipped with a Dean-Stark trap. The solution was cooled to rt and concentrated. Purification by chromatography (200 g column) eluting with 25 to 60 to 100% ethyl acetate/heptane afforded the product of Step D. Calculated for C25H21F3N2O5: 487.1 (M+1). found: 487.2.

Step E ((3aS,5S,6aR)-5-aminohexahydro-2H-cyclopenta[b]furan-3a-yl)(6-(trifluoromethyl)-2H-benzo[e][1,3]oxazin-3(4H)-yl)methanone

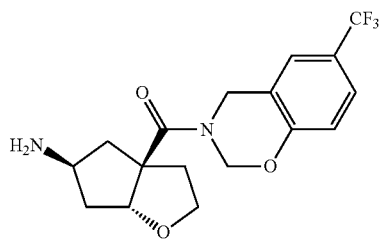 [SMILES: N[C@@H]1C[C@H]2OCC[C@@]2(C(=O)N2COc3ccc(C(F)(F)F)cc3C2)C1]

A solution of the product of Step D (5.39 g, 11.1 mmol, 1 eq) and hydrazine (7.1 mL, 222 mmol, 20 eq) in ethanol (60 mL) was stirred at rt 18 hours. The white solid was filtered, washed with methanol and DCM, and the filtrates concentrated. Saturated NaHCO₃ was added, the aqueous extracted with DCM, the organics combined, dried over MgSO₄ and concentrated to afford the product of Step E. Calculated for C17H19F3N2O3: 357.1 (M+1). found: 357.3.

Step F ((3aS,5S,6aR)-5-(((3S,4S)-3-methoxytetrahydro-2H-pyran-4-yl)amino)hexahydro-2H-cyclopenta[b]furan-3a-yl)(6-(trifluoromethyl)-2H-benzo[e][1,3]oxazin-3(4H)-yl)methanone

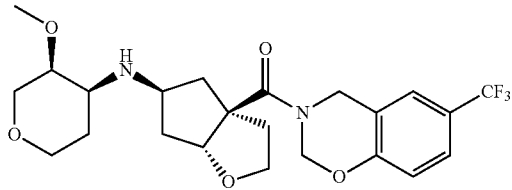 [SMILES: CO[C@@H]1COCC[C@@H]1N[C@@H]1C[C@H]2OCC[C@@]2(C(=O)N2COc3ccc(C(F)(F)F)cc3C2)C1]

The title compound was prepared from the reaction of the product of Step E and (R)-3-methoxydihydro-2H-pyran-4(3H)-one (Intermediate 1) following the procedure described in Example 1, Step H. ¹H NMR (CHLOROFORM-d) δ: 7.42 (d, J=8.6 Hz, 1H), 7.36 (br. s., 1H), 6.95 (d, J=8.1 Hz, 1H), 5.43 (br. s., 2H), 4.96-5.11 (m, 1H), 4.82 (br. s., 2H), 3.84-4.15 (m, 3H), 3.68 (d, J=7.1 Hz, 1H), 3.55 (br. s., 1H), 3.32-3.45 (m, 4H), 3.20-3.32 (m, 2H), 2.69-2.84 (m, 1H), 2.39 (br. s., 1H), 2.12-2.25 (m, 2H), 1.99-2.12 (m, 1H), 1.78-1.99 (m, 1H), 1.46-1.78 (m, 4H). Calculated for C23H29F3N2O5: 471.2 (M+1). found: 471.2.

Example 36

((3aS,5S,6aR)-5-(((3R,4R)-3-methoxytetrahydro-2H-pyran-4-yl)amino)hexahydro-2H-cyclopenta[b]furan-3a-yl)(6-(trifluoromethyl)-2H-benzo[e][1,3]oxazin-3(4H)-yl)methanone

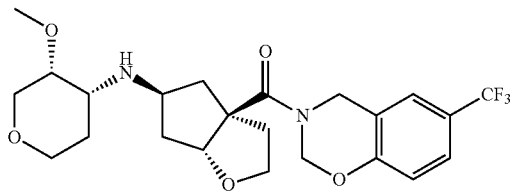 [SMILES: CO[C@H]1COCC[C@H]1N[C@@H]1C[C@H]2OCC[C@@]2(C(=O)N2COc3ccc(C(F)(F)F)cc3C2)C1]

The title compound was prepared from the reaction of the product of Step E and (S)-3-methoxydihydro-2H-pyran-4(3H)-one following the procedure described in Example 1, Step H. ¹H NMR (CHLOROFORM-d) δ: 7.42 (d, J=8.6 Hz, 1H), 7.36 (br. s., 1H), 6.96 (d, J=8.6 Hz, 1H), 5.35-5.49 (m, 2H), 5.05 (d, J=5.1 Hz, 1H), 4.74-4.90 (m, 2H), 4.05 (dd, J=12.6, 3.5 Hz, 1H), 3.94-4.01 (m, 1H), 3.91 (dt, J=11.4, 3.7 Hz, 1H), 3.61-3.71 (m, 1H), 3.48-3.60 (m, 1H), 3.24-3.41 (m, 6H), 2.78 (dd, J=6.3, 3.8 Hz, 1H), 2.39 (br. s., 1H), 2.19 (td, J=12.1, 6.1 Hz, 2H), 2.05 (dt, J=12.3, 8.3 Hz, 1H), 1.89 (br. s., 1H), 1.43-1.75 (m, 4H). Calculated for C23H29F3N2O5: 471.2 (M+1). found: 471.2.

Example 37

3-(1-((3aS,5S,6aR)-3a-(6-(trifluoromethyl)-3,4-dihydro-2H-benzo[e][1,3]oxazine-3-carbonyl)hexahydro-2H-cyclopenta[b]furan-5-yl)piperidin-4-yl)benzoic acid

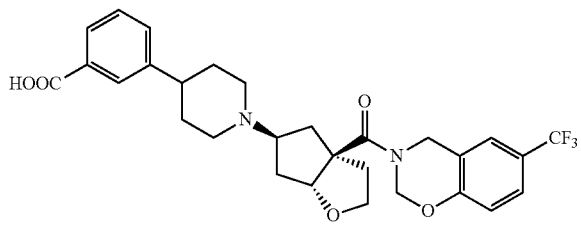 [SMILES: O=C(O)c1cccc(C2CCN([C@@H]3C[C@H]4OCC[C@@]4(C(=O)N4COc5ccc(C(F)(F)F)cc5C4)C3)CC2)c1]

The title compound of Example 37 was made by taking the product of Example 35, Step E following the procedures described in Example 31, Steps A and B, then reacting that product with 3-benzyloxycarbonylphenylboronic acid following the procedure described in Example 31, Step C, then following the procedure described in Example 31, Step D. ¹H NMR (CHLOROFORM-d) δ: 8.04 (s, 1H), 7.78 (d, J=6.8 Hz, 1H), 7.32-7.43 (m, 2H), 7.19-7.32 (m, 2H), 6.93 (d, J=8.3 Hz, 1H), 5.16-5.66 (m, 2H), 5.06 (d, J=4.2 Hz, 1H), 4.96 (d, J=16.9 Hz, 1H), 4.72 (d, J=16.9 Hz, 1H), 3.96-4.11 (m, 1H), 3.55-3.75 (m, 2H), 3.47 (s, 1H), 3.29-3.45 (m, 2H), 2.59-2.80 (m, 2H), 2.35-2.59 (m, 5H), 2.30 (dd, J=12.8, 5.7 Hz, 1H), 2.13-2.24 (m, 1H), 1.99-2.13 (m, 2H), 1.92 (d, J=11.7 Hz, 1H), 1.82 (d, J=13.4 Hz, 1H). Calculated for C29H31F3N2O5: 545.2 (M+1). found: 545.2.

Example 38

((3aS,5S,6aR)-5-(4-phenylpiperidin-1-yl)hexahydro-2H-cyclopenta[b]furan-3a-yl)(6-(trifluoromethyl)-2H-benzo[e][1,3]oxazin-3(4H)-yl)methanone

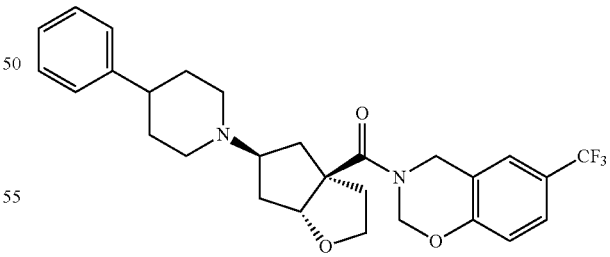

The title compound of Example 38 was made by taking the product of Example 35, Step E following the procedures described in Example 31, Steps A through D. ¹H NMR (CHLOROFORM-d) δ: 7.42 (d, J=8.6 Hz, 1H), 7.37 (br. s., 1H), 7.29 (t, J=7.5 Hz, 2H), 7.15-7.24 (m, 3H), 6.96 (d, J=8.6 Hz, 1H), 5.42 (br. s., 2H), 5.03 (d, J=4.6 Hz, 1H), 4.69-4.95 (m, 2H), 3.95-4.07 (m, 1H), 3.60-3.73 (m, 1H), 3.04 (br. s., 3H), 2.32-2.56 (m, 2H), 2.19-2.31 (m, 2H), 1.89-2.17 (m, 4H), 1.53-1.89 (m, 6H). Calculated for C28H31F3N2O3: 501.2 (M+1). found: 501.2.

Example 39

N,N-dimethyl-3-(1-((3aS,5S,6aR)-3a-(6-(trifluoromethyl)-3,4-dihydro-2H-benzo[e][1,3]oxazine-3-carbonyl)hexahydro-2H-cyclopenta[b]furan-5-yl)piperidin-4-yl)benzamide

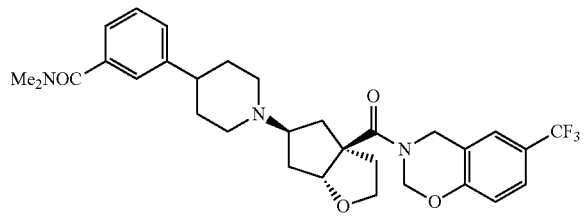

The title compound of Example 39 was made by taking the product of Example 35, Step E following the procedures described in Example 31, Steps A and B, then reacting that product with N,N-dimethylbenzamide-3-boronic acid following the procedure described in Example 31, Step C, then following the procedure described in Example 31, Step D. Calculated for C31H36F3N3O4: 572.3 (M+1). found: 572.3.

Example 40

((3aS,5S,6aR)-5-(((3S,4S)-3-methoxytetrahydro-2H-pyran-4-yl)(methyl)amino)hexahydro-2H-cyclopenta[b]furan-3a-yl)(3-(trifluoromethyl)-7,8-dihydro-1,6-naphthyridin-6(5H)-yl)methanone

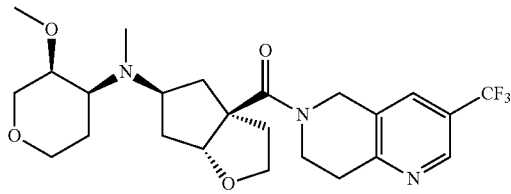 [SMILES: CO[C@@H]1COCC[C@@H]1N(C)[C@@H]1C[C@H]2OCC[C@@]2(C(=O)N2CCc3ncc(C(F)(F)F)cc3C2)C1]

The title compound of Example 40 was made by taking the product of Example 30 and reacting with formaldehyde following the procedures described in Example 1, Step H. $^1$H NMR (CHLOROFORM-d) δ: 8.72 (br. s., 1H), 7.70 (br. s., 1H), 5.03 (d, J=4.6 Hz, 1H), 4.67-4.92 (m, 2H), 4.15 (d, J=12.7 Hz, 1H), 3.97-4.10 (m, 2H), 3.92 (br. s., 2H), 3.55-3.71 (m, 2H), 3.33-3.53 (m, 5H), 3.22 (d, J=12.7 Hz, 1H), 3.14 (br. s., 2H), 2.64 (d, J=11.7 Hz, 1H), 2.22-2.50 (m, 4H), 1.79-2.22 (m, 6H), 1.69 (td, J=12.5, 4.9 Hz, 1H), 1.51 (d, J=12.0 Hz, 1H). Calculated for C24H32F3N3O4: 484.2 (M+1). found: 484.2.

Example 41

((3aS,5S,6aR)-5-((2-methoxyethyl)((3S,4S)-3-methoxytetrahydro-2H-pyran-4-yl)amino)hexahydro-2H-cyclopenta[b]furan-3a-yl)(3-(trifluoromethyl)-7,8-dihydro-1,6-naphthyridin-6(5H)-yl)methanone

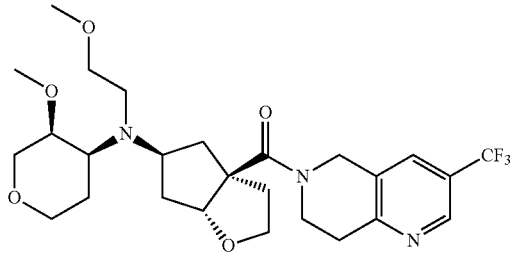 [SMILES: COCCN([C@@H]1C[C@H]2OCC[C@@]2(C(=O)N2CCc3ncc(C(F)(F)F)cc3C2)C1)[C@H]1CCOC[C@H]1OC]

The title compound of Example 41 was made by taking the product of Example 30 and reacting with methoxyacetaldehyde following the procedures described in Example 1, Step H. Calculated for C26H36F3N3O5: 528.3 (M+1). found: 528.3.

Example 42

((3aS,5S,6aR)-5-(((3S,4S)-3-methoxytetrahydro-2H-pyran-4-yl)(2,5,8,11-tetraoxatetradecan-14-yl)amino)hexahydro-2H-cyclopenta[b]furan-3a-yl)(3-(trifluoromethyl)-7,8-dihydro-1,6-naphthyridin-6(5H)-yl)methanone

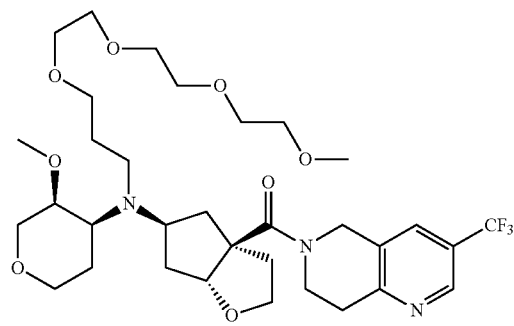 [SMILES: COCCOCCOCCOCCCN([C@@H]1C[C@H]2OCC[C@@]2(C(=O)N2CCc3ncc(C(F)(F)F)cc3C2)C1)[C@H]1CCOC[C@H]1OC]

The title compound of Example 42 was made by taking the product of Example 30 and reacting with 4,7,10,13-tetraoxatetradecanal following the procedures described in Example 1, Step H. Calculated for C33H50F3N3O8: 674.4 (M+1). found: 674.4.

Example 43

((3aS,5S,6aR)-5-((2-hydroxyethyl)((3S,4S)-3-methoxytetrahydro-2H-pyran-4-yl)amino)hexahydro-2H-cyclopenta[b]furan-3a-yl)(3-(trifluoromethyl)-7,8-dihydro-1,6-naphthyridin-6(5H)-yl)methanone

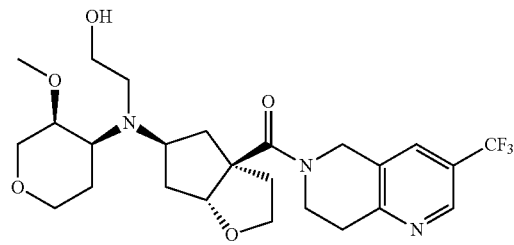 [SMILES: CO[C@@H]1COCC[C@@H]1N(CCO)[C@@H]1C[C@H]2OCC[C@@]2(C(=O)N2CCc3ncc(C(F)(F)F)cc3C2)C1]

Step A ((3aS,5S,6aR)-5-((2-((tert-butyldimethylsilyl)oxy)ethyl)((3S,4S)-3-methoxytetrahydro-2H-pyran-4-yl)amino)hexahydro-2H-cyclopenta[b]furan-3a-yl)(3-(trifluoromethyl)-7,8-dihydro-1,6-naphthyridin-6(5H)-yl)methanone

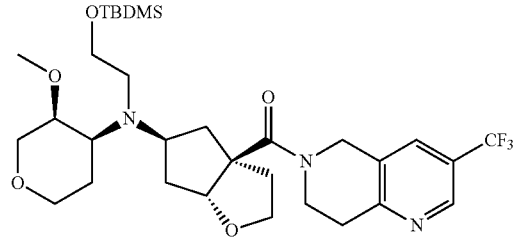 [SMILES: CO[C@@H]1COCC[C@@H]1N(CCO[Si](C)(C)C(C)(C)C)[C@@H]1C[C@H]2OCC[C@@]2(C(=O)N2CCc3ncc(C(F)(F)F)cc3C2)C1]

The title compound of Step A was made by taking the product of Example 30 and reacting with t-butyldimethylsiloxyacetaldehyde following the procedures described in Example 1, Step H. Calculated for C31H48F3N3O5Si: 628.3 (M+1). found: 628.2.

Step B ((3 aS,5S,6aR)-5-((2-hydroxyethyl)((3S,4S)-3-methoxytetrahydro-2H-pyran-4-yl)amino)hexahydro-2H-cyclopenta[b]furan-3a-yl)(3-(trifluoromethyl)-7,8-dihydro-1,6-naphthyridin-6(5H)-yl)methanone

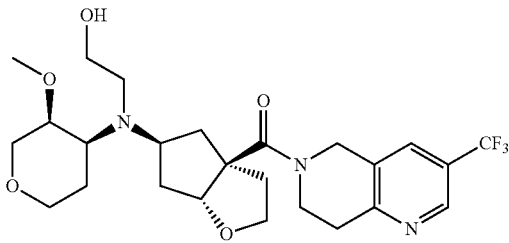 [SMILES: CO[C@@H]1COCC[C@@H]1N(CCO)[C@@H]1C[C@H]2OCC[C@@]2(C(=O)N2CCc3ncc(C(F)(F)F)cc3C2)C1]

A solution of the product of Step A (210 mg, 0.33 mmol, 1 eq) in 1 N HCl (0.25 mL) and dioxane (5 mL) was heated to 90° C. for 18 hrs, then cooled to rt. Saturated NaHCO$_3$ was added, the aqueous extracted with CH$_2$Cl$_2$, dried over MgSO$_4$ and concentrated. Purification by chromatography (12 g) eluting with 3 to 8% MeOH/DCM afforded the title of compound of Example 43 (67 mg, 38%). $^1$H NMR (CHLOROFORM-d) δ: 8.72 (br. s., 1H), 7.71 (br. s., 1H), 4.96 (d, J=4.4 Hz, 1H), 4.80 (br. s., 2H), 4.15 (d, J=12.7 Hz, 1H), 3.77-4.10 (m, 5H), 3.56-3.70 (m, 1H), 3.30-3.52 (m, 7H), 3.23 (d, J=12.7 Hz, 1H), 3.14 (br. s., 2H), 2.66-2.90 (m, 3H), 2.39 (br. s., 1H), 2.13-2.27 (m, 1H), 2.05 (dd, J=12.7, 5.6 Hz, 3H), 1.82 (br. s., 1H), 1.68 (td, J=12.6, 4.9 Hz, 1H), 1.42 (br. s., 1H). Calculated for C25H34F3N3O5: 514.3 (M+1). found: 514.3.

Example 44

((3aS,5S,6aR)-5-((3-hydroxypropyl)((3S,4S)-3-methoxytetrahydro-2H-pyran-4-yl)amino)hexahydro-2H-cyclopenta[b]furan-3a-yl)(3-(trifluoromethyl)-7,8-dihydro-1,6-naphthyridin-6(5H)-yl)methanone

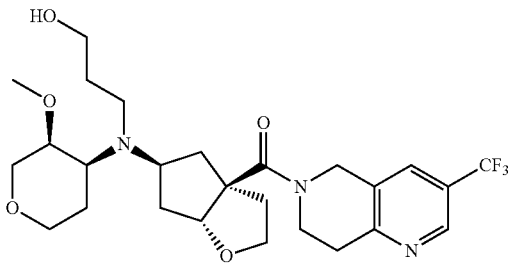 [SMILES: CO[C@@H]1COCC[C@@H]1N(CCCO)[C@@H]1C[C@H]2OCC[C@@]2(C(=O)N2CCc3ncc(C(F)(F)F)cc3C2)C1]

The title compound of Example 44 was made by taking the product of Example 30 and reacting with 3-((tert-butyldimethylsilyl)oxy)propanal following the procedures described in Example 43 Steps A and B. $^1$H NMR (CHLOROFORM-d) δ: 8.72 (s, 1H), 7.72 (s, 1H), 4.97 (d, J=4.5 Hz, 1H), 4.69-4.91 (m, 2H), 4.15 (d, J=12.6 Hz, 1H), 3.83-4.10 (m, 5H), 3.58-3.82 (m, 3H), 3.33-3.47 (m, 5H), 3.25 (d, J=12.6 Hz, 1H), 3.14 (br. s., 2H), 2.70-2.93 (m, 3H), 2.36 (br. s., 1H), 2.15-2.30 (m, 1H), 1.97-2.15 (m, 3H), 1.78-1.96 (m, 1H), 1.35-1.77 (m, 4H). Calculated for C26H36F3N3O5: 528.3 (M+1). found: 528.3.

Example 45

In Vitro Biological Data

Compounds of the invention were subjected to various representative biological tests. The results of these tests are intended to illustrate the invention in a non-limiting fashion.
MCP-1 Receptor Binding Assay in THP-1 Cells Human monocytic cell line THP-1 cells were obtained from American Type Culture Collection (Manassas, Va., USA). The THP-1 cells were grown in RPMI-1640 (RPMI: Roswell Park Memorial Institute Medium-cell culture growth media) supplemented with 10% fetal bovine serum in a humidified 5% CO$_2$ atmosphere at 37° C. The cell density was maintained between 0.5×10$^6$ cells/mL.

THP-1 (cells were incubated with 0.5 nM $^{125}$I labeled MCP-1 (Perkin-Elmer Life Sciences, Inc. Boston, Mass.) in the presence of varying concentrations of either unlabeled MCP-1 (R & D Systems, Minneapolis, Minn.) or test compound for 2 hours at 30° C. in a 96 well plate. Cells were then harvested onto a filter plate, dried, and 20 μL of Microscint 20 was added to each well. Plates were counted in a TopCount NXT, Microplate Scintillation & Luminescence Counter (Perkin-Elmer Life Sciences, Inc. Boston, Mass.). Blank values (buffer only) were subtracted from all values and drug treated values were compared to vehicle treated values. 1 μM cold MCP-1 was used for nonspecific binding.

Table 1 lists IC$_{50}$ values for inhibition of MCP-1 binding to CCR2 obtained for test compounds of the invention. Where an IC$_{50}$ value was not obtained for a particular compound, the percent inhibition is provided at a test concentration of 25 μM.

TABLE 1

| Inhibition of MCP-1 Binding IC$_{50}$ | |
|---|---|
| Example | CCR2 Binding (nM) |
| 1 | 16 |
| 2 | 7 |
| 3 | 11 |
| 4 | 93 |
| 5 | 170 |
| 6 | 62 |
| 7 | 2 |
| 8 | 3 |
| 9 | 9 |
| 10 | 16 |
| 11 | 4 |
| 12 | 24 |
| 13 | 20 |
| 16 | 14 |
| 21 | 120 |

The compounds of Examples 15, 29-31, 33, 35-37, 39, and 40 are believed to have CCR2 binding of less than about 50 nM, those of Examples 14, 20, 22, and 25 are believed to have CCR2 binding of about 50-100 nM, those of Examples 17, 26, 38, and 43-44 are believed to have CCR2 binding of about 100-200 nM, and those of Examples 18, 19, 23, 24, 27, 28, 32, 34, 41 and 42 are believed to have CCR2 binding of greater than about 200 nM.

Example 46

Animals

Mouse CCR2 knock-out/human CCR2 knock-in mice are generated using targeted 129Sv/Evbrd embryonic stem cell clones injected into C57BL/6 mice. Expression of the hCCR2 transcript is confirmed by quantitative reverse transcription-polymerase chain reaction performed on spleen and blood total RNA from homozygous hCCR2 knock-in mice. Backcrossing into C57BL/6 genetic background continued to the eighth generation. Transgenic mice are housed in a specific-pathogen-free, temperature-controlled facility that maintained a 12-hour light/12-hour dark cycle. Mice have free access to water and food. Experimental procedures are carried out in accordance with institutional standards for animal care and are approved by the institute's animal care and use committee.

Example 47

Murine In Vivo Cell Migration Assay

Animals are orally dosed with vehicle or CCR2 antagonists at 3, 10 and 30 mg/kg bid. Animals undergo anesthesia and laparotomy. A distal loop of small bowel (5 cm in length) is gently eventrated onto moist sterile gauze. Synthetic human MCP-1 (1 mg/100 ml sterile PBS) or PBS alone is administered drop-wise onto the serosa of the eventrated loop. A suture knot is placed into the mesentery to mark the terminus of the treated area. Twenty-four hours later, the animal is sacrificed and the segment of bowel plus the adjacent region is removed. The tissue is opened along the mesenteric border, pinned flat and the mucosa removed. The remaining muscle layer is fixed briefly in 100% EtOH and then stained using Hanker-Yates reagent to detect myeloperoxidase-containing immune cells. At 10 mpk, P.O. bid, a compound is deemed efficacious if the inhibition of cell migration reaches 30% compared with vehicle-treated animals.

Example 48

Thioglycollate-Induced Peritonitis in Mice

Animals were orally dosed with vehicle or the compound of Example 30 at 0, 1, 3, and 10 mg/kg bid). One hour later, the animals were intraperiponeally injected with sterile thioglycollate (25 mL/kg, ip, Sigma) for induction of peritonitis. Animals were orally treated twice daily with vehicle or Example 30. At the 72-hour time point, perinoteal cavities were lavaged with 10 mL of sterile saline. Total cell counts in the peritoneal lavage fluid were performed using a microscope and cell differentiation is performed using cytospin analysis after Giemsa staining (Hema Tek 2000). Percent inhibition of the thioglycollate-induced peritonitis was calculated by comparing the change in number of leukocytes of CCR2 antagonist treated mice to the vehicle-treated mice. When the compound of Example 30 was administered at 1, 3 and 10 mg/kg p.o bid, the thioglycollate induced cellular infiltrate in hCCR2KI mice at 72 hr was inhibited by 51%, 67% and 95%, respectively. The effect of Example 30 was demonstrated to be dose-dependent with an $ED_{50}$ of 1 mg/kg p.o. bid, and a cmax $EC_{50}$ of 97 nM in plasma (0.5 hour post the last dose).

Example 49

MCP-1-Induced Monocyte Recruitment to Airway of Mice

Animals are orally treated with vehicle or CCR2 antagonists at 3, 10, and 30 mg/kg po bid). One hour later, the animals are intranasally dosed with 4 µg of MCP-1 in sterile saline. The animals are orally treated twice daily with vehicle or CCR2 antagonists. After 48 h, mice are euthanized by intraperitoneal injection of anesthesia solution (Sleepaway-Sodium pentobarbital). Whole bronchoalveolar lavage (BAL) is performed using 1.4 ml of ice-cold PBS containing 3 mM EDTA. Total cell counts in the BAL lavage fluid are performed using a microscope and cell differentiation is performed using cytospin analysis after Giemsa staining (Hema Tek 2000). Percent inhibition is calculated by comparing the change in number of total leukocyte counts (including monocytes/macrophages and lymphocytes) of compound-treated mice to the vehicle-treated mice. Compounds are deemed efficacious if percent inhibition reaches 30%.

Example 50

High-Fat Diet Induced Obesity and Insulin Resistance in Mice

Obesity was induced by a high-fat diet that derived approximately 60% calories from fat (D-12492; Research Diets Inc.) in animals for 10-12 weeks at age of 7 weeks. Prior to age 7 weeks, animals were fed a standard pellet diet, in which 5% of calories were provided as fat. Obese animals were randomized by body weight. The obese animals were orally treated with vehicle or the compound of Example 30 at 1, 3, and 10 mg/kg, po bid. Body weight and food intake and fasting blood glucose levels were monitored. Body mass was determined by a NMR analyzer (Bruker MiniSpec). Insulin tolerance test was carried out in animals that fasted for 3 hours. After an intraperitoneal bolus injection of recombinant human insulin (0.5 U/kg), blood glucose concentrations were measured using a Glucometer before and 15, 30, 45, 60, 90 and 120 minutes after injection. Glucose tolerance tests were performed after an overnight (17-hour) fast. Blood glucose concentrations were measured before and after 15, 30, 60, 90, 120 minutes after an oral dose of glucose dissolved in water (2.5 g/kg). Energy expenditure analysis was monitored by a complete laboratory animal monitor system. After 50 days treatment with vehicle or CCR2 antagonists, the animals were sacrificed by $CO_2$ asphyxiation. Percent of weight loss was calculated by comparing the body weight changes of the compound-treated mice with the vehicle-treated mice. After 32-days treatment, the compound of Example 30 reduced the high fat-diet induced body weight by 4.94% ($p>0.05$), 10.94% ($p<0.01$) and 15.7% ($p<0.01$) when administered at 1, 3 and 10 mg/kg p.o. bid, respectively.

Example 51

Mouse Model of Allergic Asthma

Animals are sensitized by intraperitoneal injection of 10 µg chicken egg albumin (OVA) absorbed to 1 mg Imject® in 100 µL phosphate-buffered saline (PBS) on days 0 and 5. Control animals received PBS ip. OVA-immunized animals are challenged by inhalation of 0.5% OVA aerosol for 10 minutes by an ultrasonic nebulizer on days 12, 16 and 20. Control animals are challenged with PBS in similar fashion. The OVA-sensitized animals receive vehicle (0.5% Methocel) or CCR2 antagonists orally at 3, 10, 30 mg/kg twice daily from days 9-20 and once daily on Day 21, 2 hours before sacrifice. Dexamethason (5 mg/kg) and Montelukast (1 mg/kg) are given orally once a day. On day 21, 2 hours post the last dose of CCR2 compounds, bronchial reactivity to aerosolized methacholine is measured using a Buxco whole body plethysmograpgh. On day 21, the animals are sacrificed. Bronchoalveolar lavage fluid is collected (1 mL) and total cells counted. The numbers of eosinophils, lymphocytes, monocytes and neutrophils are determined using cytospin analysis after Giemsa staining (Hema Tek 2000). Percent inhibition of total BAL leukocyte count (and eosinophil count) is calculated by comparing the compound-treated mice with vehicle-treated mice. Compounds are deemed efficacious if the inhibition reaches 30%.

Example 52
Preparation of Crystalline Succinate Salt of Compound of Formula (I-S)

The crystalline succinate salt of the compound of formula (I) was prepared by heating amorphous succinate salt (the amorphous succinate salt is the foam described in Example 30, Step M) of the compound of formula (I) in an open DSC aluminum pan to about 140° C. with a heating rate of 10° C./min, then cooling to about 30° C. with a cooling rate of 10° C./min.

Figure 5:
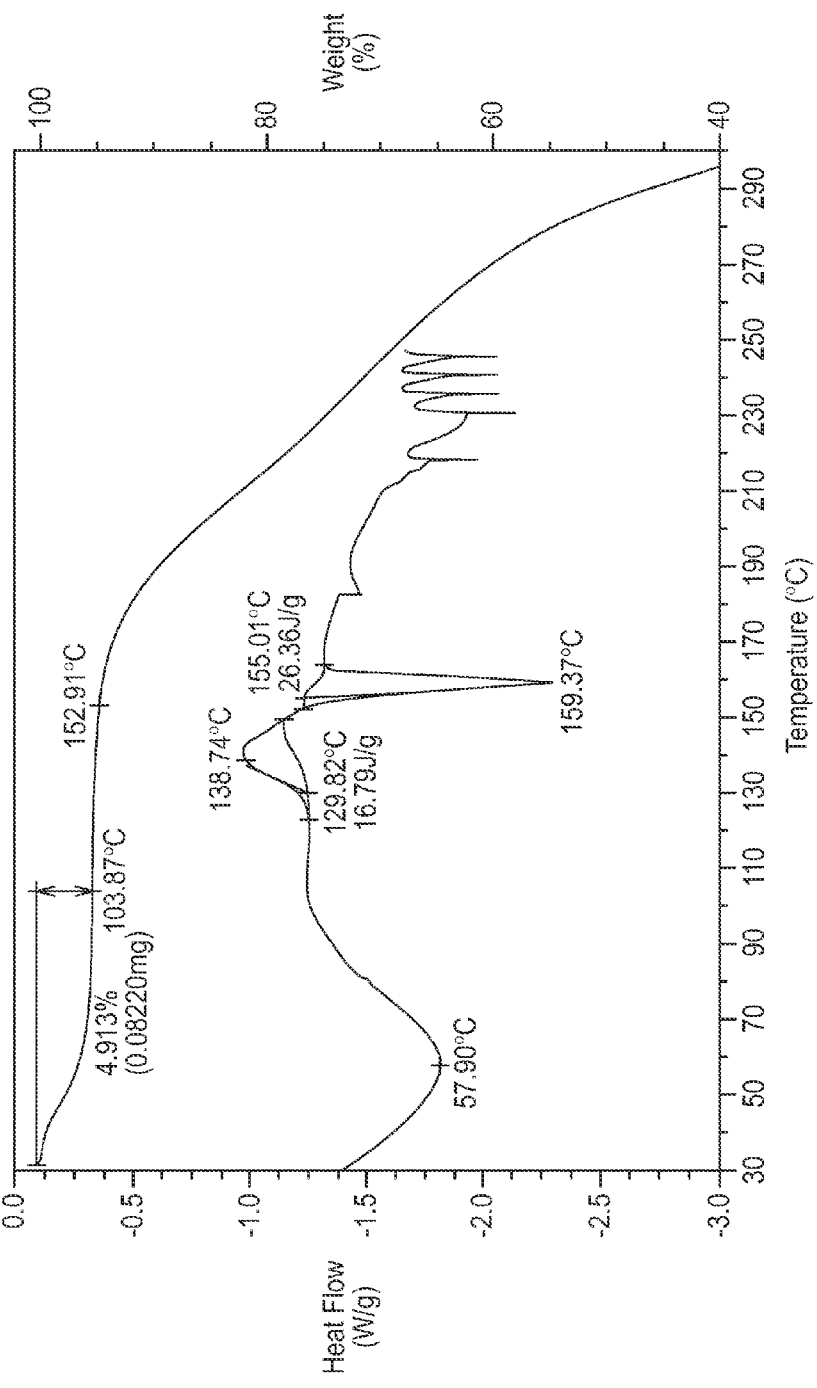
FIG. 5 illustrates a DSC thermogram showing conversion of a representative sample of the amorphous succinate salt of the compound of formula (I-S) to a crystalline succinate salt of the compound of formula (I-S); and a TGA thermogram for a representative sample of amorphous succinate salt of the compound of formula (I-S).

FIG. 5 illustrates a DSC thermogram measured during the experiment described above. The DSC thermogram shows a first endothermic event at about 50° C. (theorized to be the result of desolvation of the amorphous form); an exothermic event with a maximum at about 138° C., indicative of crystallization; and a subsequent endothermic event at 155° C., indicative of the melting of the crystalline solid.

FIG. 5 further includes a TGA thermogram for the amorphous succinate salt of the compound of formula (I-S) used in the example described above, which shows about 4.8% weight loss between room temperature and about 80° C.; and decomposition starting at about 172° C.

Example 53
Preparation of Crystalline Succinate Salt of Compound of Formula (I-S)

The following general procedure was applied in a screening study for identifying solvents suitable for crystallization of the crystalline succinate salt of the compound of formula (I-S). Crystalline succinate salt of the compound of formula (I-S) was prepared from the amorphous succinate salt (the amorphous succinate salt is the foam described in Example 30, Step M) of the compound of formula (I-S), crystallizing from methyl isobutyl ketone. (Note: Water, methanol ethanol, acetone, acetonitrile, isopropyl acetate, nitromethane, tetrahydrofuran, methyl ethyl ketone, dichloromethane, and toluene did not induce crystallization.)

Amorphous succinate salt of the compound of formula (I-S) (5-10 mg) was suspended in 1-2 mL of methyl-isobutyl ketone (MIBK). The resulting suspension was heated in an oil bath and at reflux conditions, the suspension formed a clear solution, which upon cooling to room temperature under ambient conditions yielded crystalline solids.

The solids isolated from MIBK were allowed to dry under ambient condition and then analyzed by X-ray. The pXRD pattern of the solid isolated from MIBK was similar to the pXRD pattern of the heat treated sample (prepared as in Example 52 above), indicating the same crystalline form was produced in both cases.

Example 54
Oral Formulation—Prophetic Example

As a specific embodiment of an oral composition, 100 mg of the compound prepared as in Example 53 is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of Formula (I):

Formula (I)

wherein:
A is O, or S;
$R^0$ is H, or $C_{(1-4)}$alkyl;
wherein said $C_{(1-4)}$alkyl is optionally substituted with OH, $C_{(1-4)}$alkyl-$(OCH_2CH_2)_n$—$OCH_3$, $OCH_3$, $CO_2H$, $C(O)NH_2$, $SO_2NH_2$, or $CO_2C_{(1-4)}$alkyl;
n is 1, 2, or 3;
$R^1$ is cyclohexyl, or tetrahydropyranyl;
wherein said cyclohexyl or tetrahydropyranyl may be optionally substituted with one substituent selected from the group consisting of: $OCH_3$, OH, $CH_2CH_3$, —CN, $NH_2$, $NH(CH_3)$, $N(CH_3)_2$, or $OCF_3$;
alternatively, $R^0$ and $R^1$ are taken together with their attached nitrogen to form a ring selected from the group consisting of $R^a$ is phenyl;
wherein the phenyl is optionally substituted with C(O)NH$_2$, C(O)NHC$_{(1-4)}$alkyl, SO$_2$NH$_2$, C(O)N(C$_{(1-4)}$alkyl)$_2$, OCH$_3$, CO$_2$CH$_3$, or CO$_2$H;
$R^b$ is C$_{(1-4)}$alkyl, or OC$_{(1-4)}$alkyl;
$R^2$ is selected from the group consisting of H, C$_{(1-4)}$alkyl, cyclopropyl, cyclohexyl, phenyl, pyridyl, pyrimidyl, pyrazyl, pyrazolyl, imidazolyl, isoxazolyl, thiazolyl, furyl, and thiophenyl;
wherein said phenyl, pyridyl, pyrimidyl, pyrazyl, pyrazolyl, imidazolyl, oxazolyl, isoxazolyl, thiazolyl, furyl, or thiophenyl is optionally substituted with one substituent selected from the group consisting of NH$_2$, NHC$_{(1-3)}$alkyl, N(C$_{(1-3)}$alkyl)$_2$, C$_{(1-3)}$alkyl, —CN, —CH=CH$_2$, —CONH$_2$, —CO$_2$H, —NO$_2$, —CONHC$_{(1-4)}$alkyl, CON(C$_{(1-4)}$alkyl)$_2$, C$_{(1-4)}$alkyl-CONH$_2$, —NHCOC$_{(1-4)}$alkyl, —CO$_2$C$_{(1-4)}$alkyl, CF$_3$, SO$_2$C$_{(1-4)}$alkyl, —SO$_2$NH$_2$, —SO$_2$NH(C$_{(1-4)}$alkyl), and —SO$_2$N(C$_{(1-4)}$alkyl)$_2$;
$R^3$ is H, or CH$_3$;
alternatively, $R^3$ and $R^2$ are taken together with their attached carbon to form

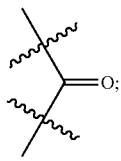 [SMILES: *C(*)=O]

$R^4$ is

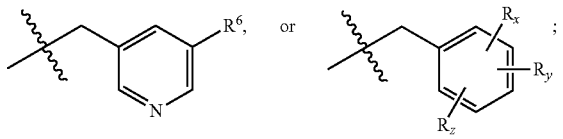

$R^5$ is H, or CH$_3$;
alternatively, $R^4$ and $R^5$ are taken together with their attached nitrogen to form a ring selected from the group consisting of:

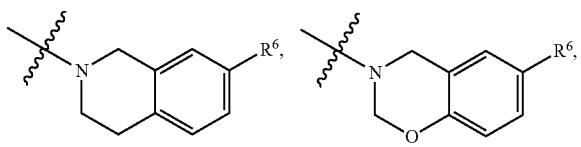

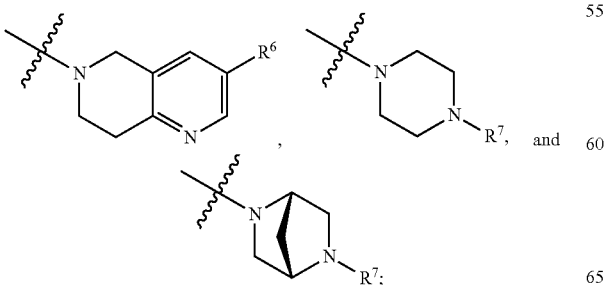

$R^6$ is CF$_3$, or OCF$_3$;
$R^7$ is a CF$_3$ substituted heteroaryl, provided that $R^7$ is not

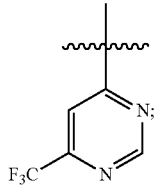

$R_x$ is CF$_3$, F, Cl, CN, or OCH$_3$;
$R_y$ is H, F, Cl, or CF$_3$;
$R_z$ is H, or F;
or a pharmaceutically acceptable salt thereof.

2. A compound of claim 1, wherein:
A is O, or S;
$R^0$ is H, or C$_{(1-4)}$alkyl, wherein said C$_{(1-4)}$alkyl is optionally substituted with OH, C$_{(1-4)}$alkyl(OCH$_2$CH$_2$)$_n$OCH$_3$, or OCH$_3$;
n is 1, 2, or 3;
$R^1$ is cyclohexyl, 1-methoxy cyclohex-2-yl, tetrahydropyran-4-yl, or 3-methoxy tetrahydropyran-4-yl;
alternatively, $R^0$ and $R^1$ are taken together with their attached nitrogen to form a ring selected from the group consisting of

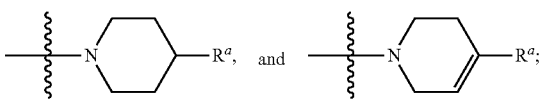

$R^a$ is phenyl;
wherein said phenyl is optionally substituted with C(O)NH$_2$, C(O)NHCH$_3$, SO$_2$NH$_2$, C(O)N(CH$_3$)$_2$, OCH$_3$, CO$_2$CH$_3$, or CO$_2$H;
$R^2$ is H, C$_{(1-4)}$alkyl, cyclopropyl, cyclohexyl, thiazol-2-yl, 1-methyl-imidazol-2-yl, 1-methyl-pyrazol-5-yl, or phenyl;
$R^4$ and $R^5$ are taken together with their attached nitrogen to form a ring selected from the group consisting of:

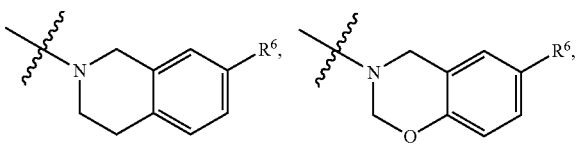

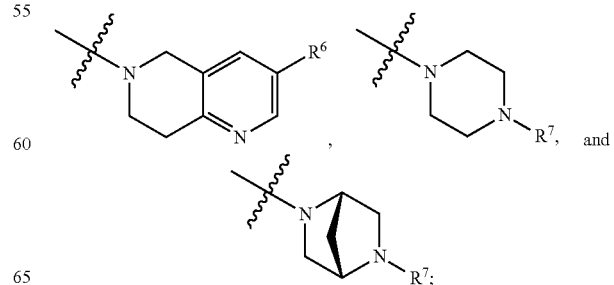

R⁶ is CF₃, or OCF₃;
R⁷ is

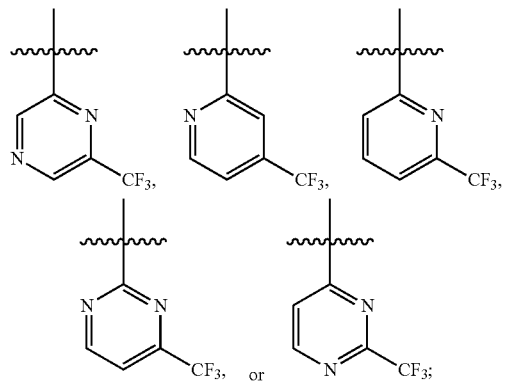

or a pharmaceutically acceptable salt thereof.

3. A compound of claim 2, wherein:

A is O, or S;

R⁰ is H, CH₃, CH₂CH₂CH₂OH, CH₂CH₂OH, CH₂CH₂CH₂—(OCH₂CH₂)₃—OCH₃, or CH₂CH₂OCH₃;

R¹ is tetrahydropyran-4-yl, or 3-methoxy tetrahydropyran-4-yl;

alternatively, R⁰ and R¹ are taken together with their attached nitrogen to form a ring selected from the group consisting of

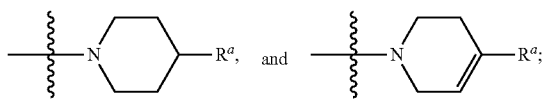

Rᵃ is phenyl;

wherein said phenyl is optionally substituted with C(O)N(CH₃)₂, OCH₃, or CO₂H;

R⁴ and R⁵ are taken together with their attached nitrogen to form a ring selected from the group consisting of:

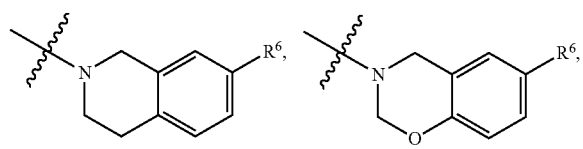

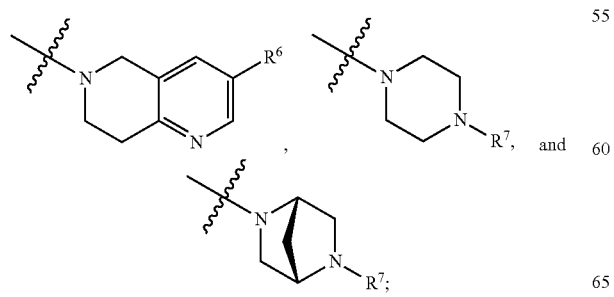

R⁶ is CF₃, or OCF₃;
R⁷ is

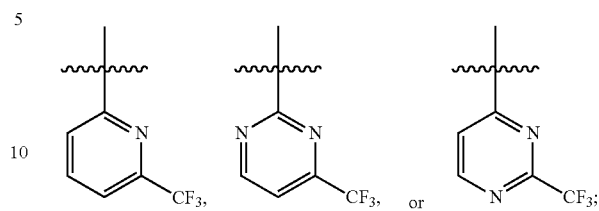

or a pharmaceutically acceptable salt thereof.

4. A compound of claim 3, wherein:

A is O;

or a pharmaceutically acceptable salt thereof.

5. A compound of claim 1 selected from the group consisting of:

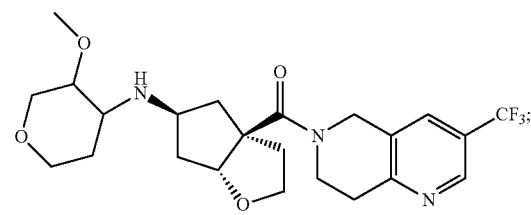

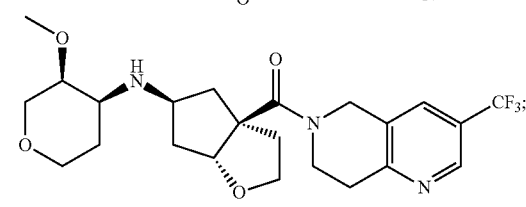

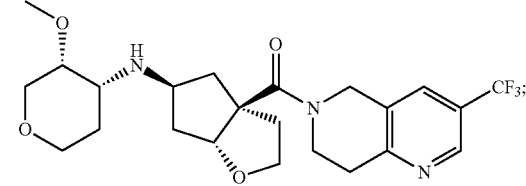

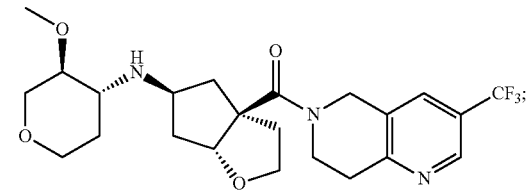

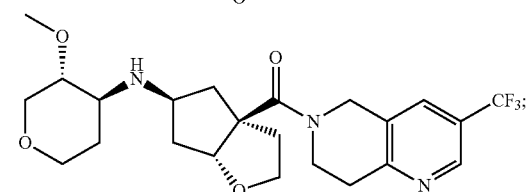

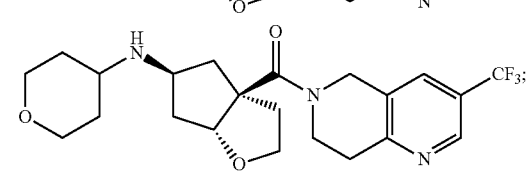

97
-continued
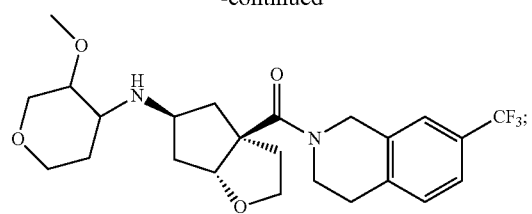
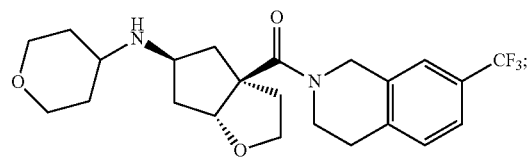
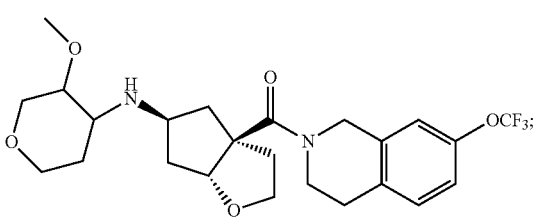
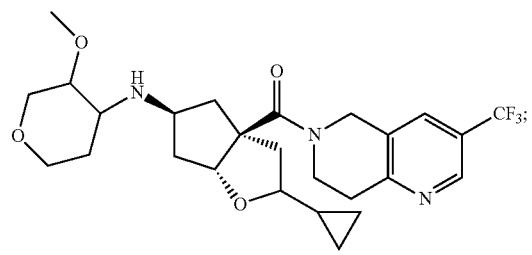
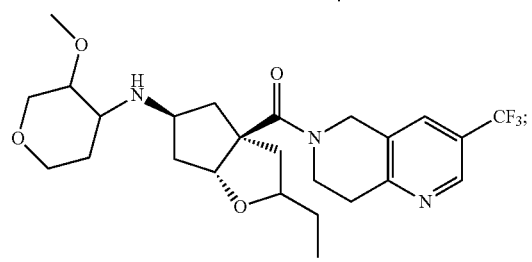
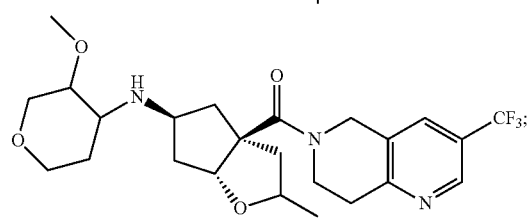
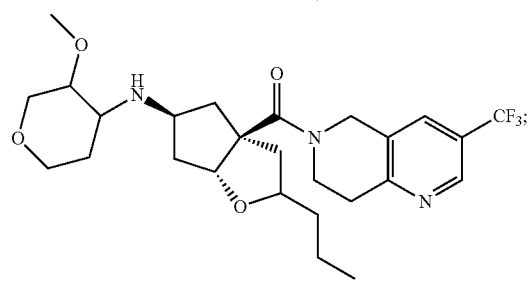
98
-continued
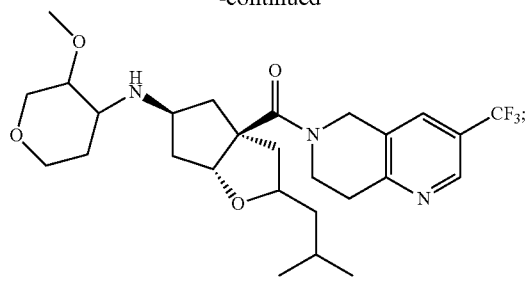
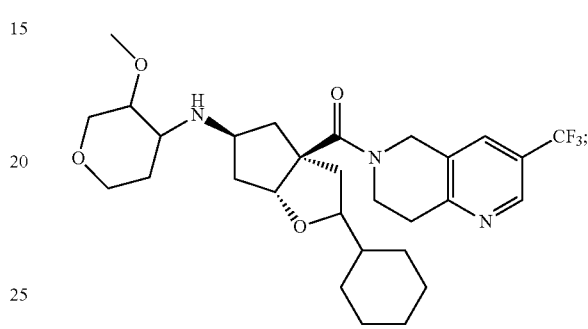
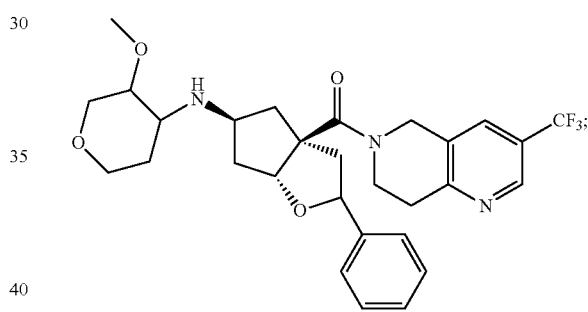
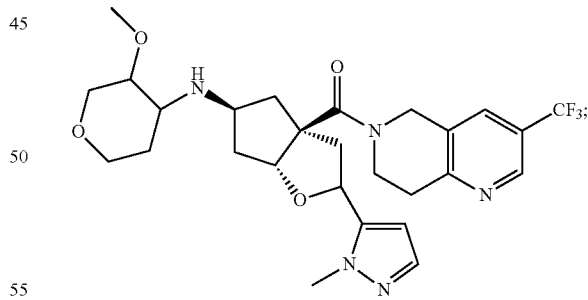
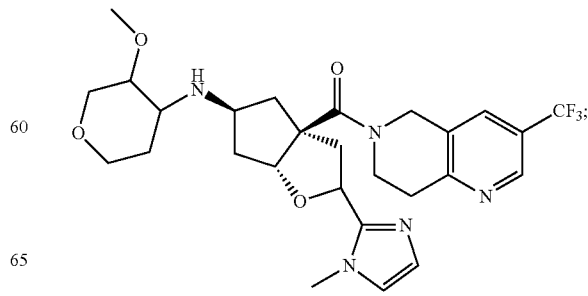

99
-continued
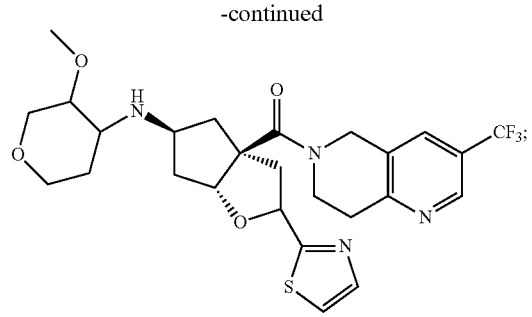
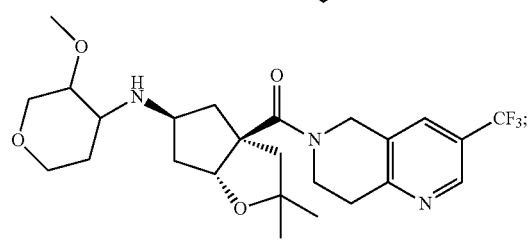
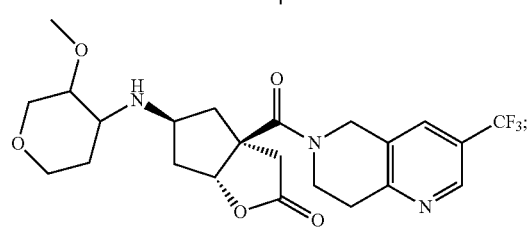
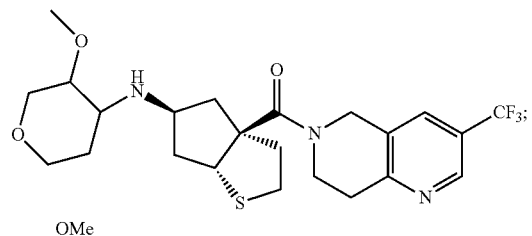
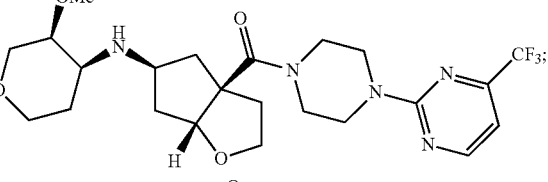
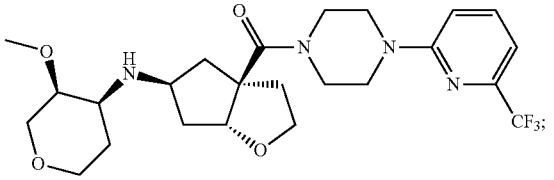
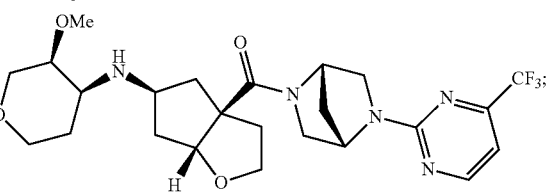
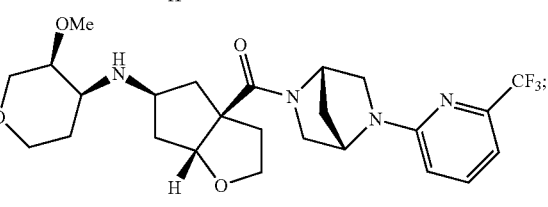
100
-continued
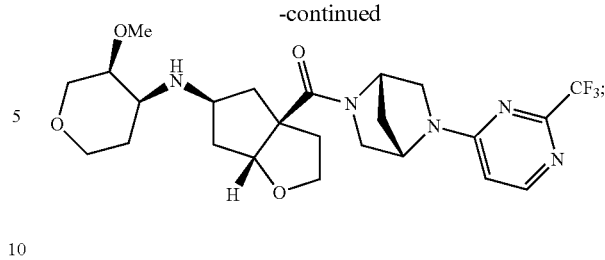
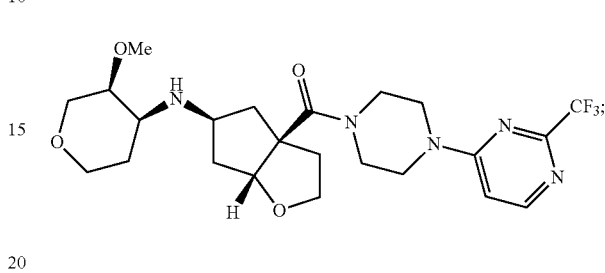
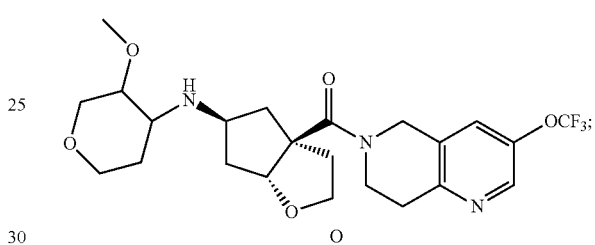
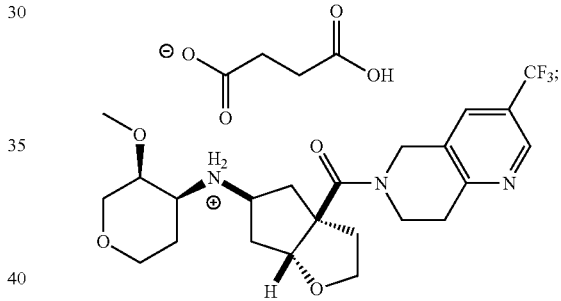
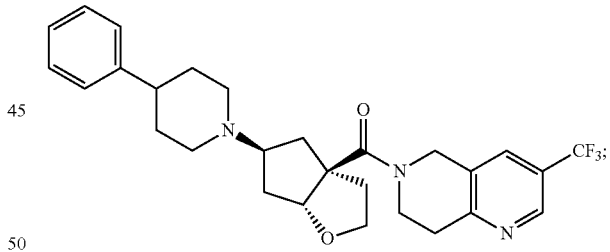
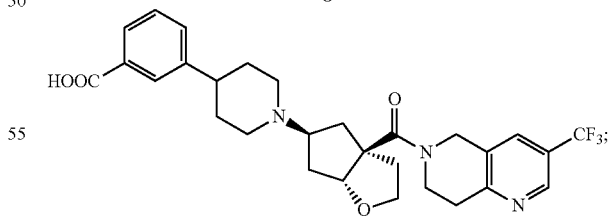
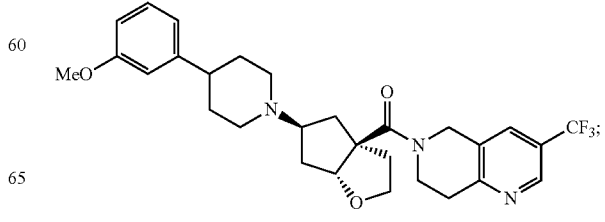

101
-continued
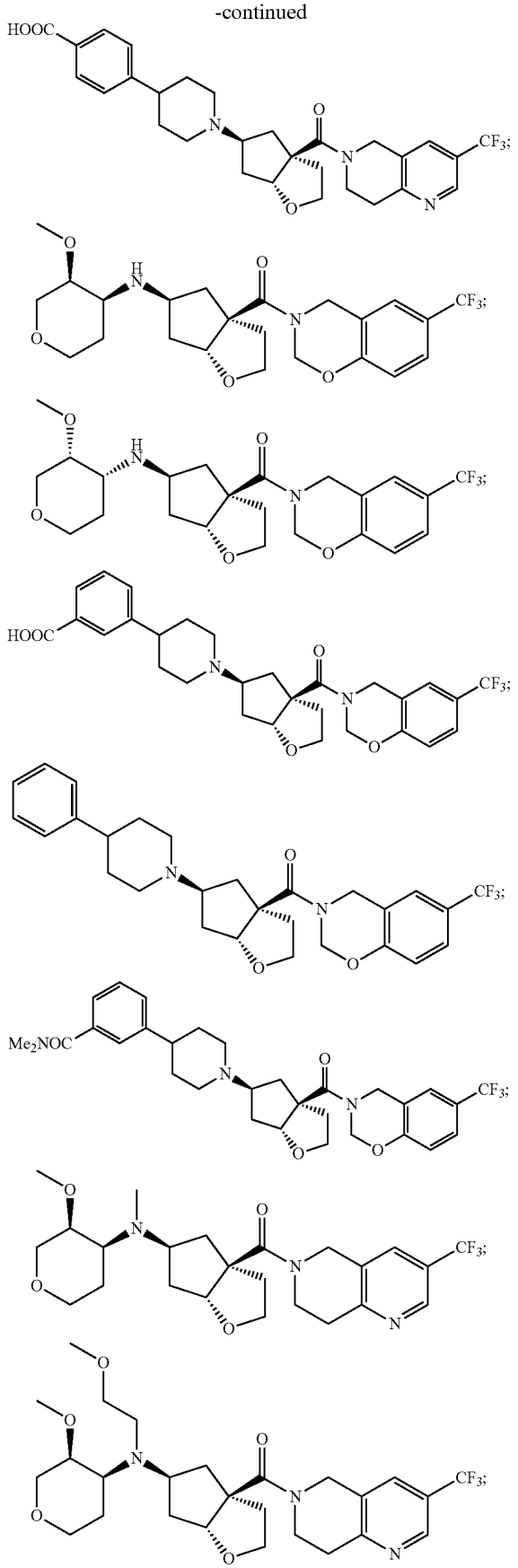
102
-continued
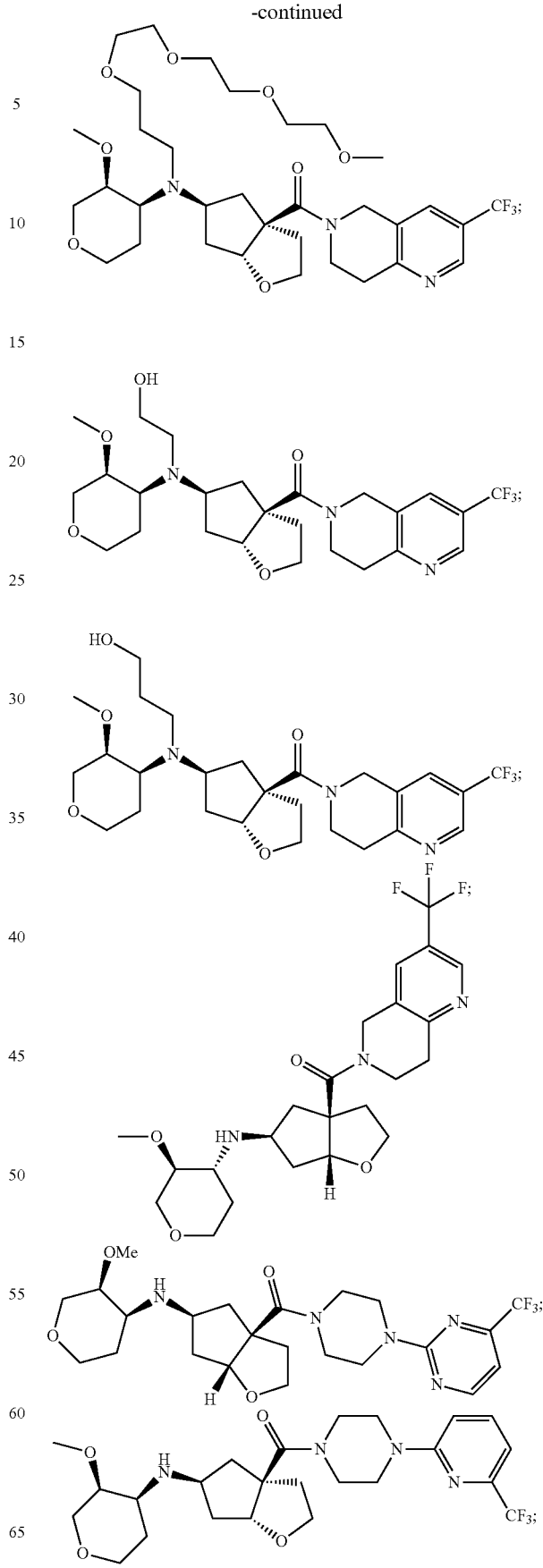

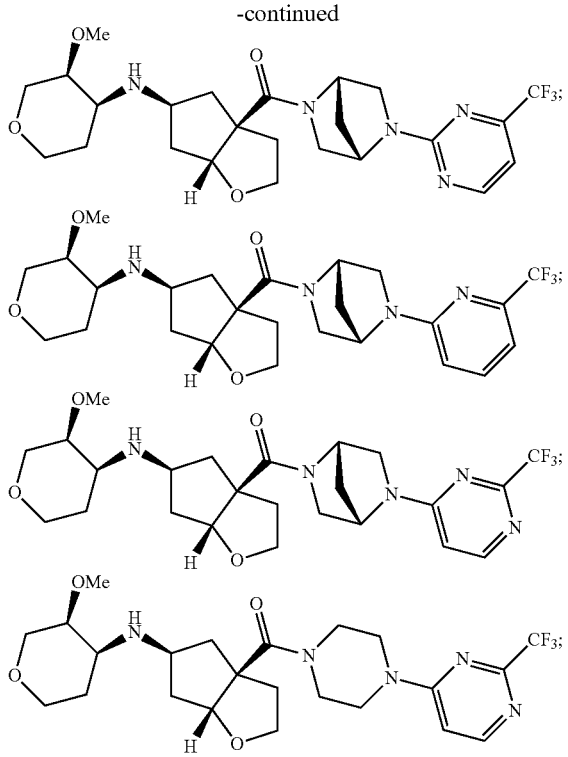

and pharmaceutically acceptable salts thereof.

6. A compound which is

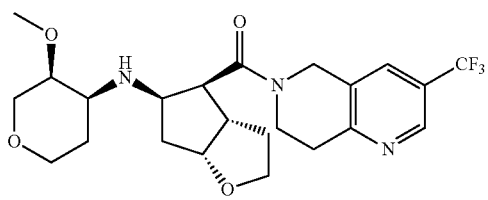 [SMILES: CO[C@@H]1COCC[C@@H]1N[C@@H]1C[C@H]2OCC[C@H]2[C@@H]1C(=O)N1CCc2ncc(C(F)(F)F)cc2C1]

and pharmaceutically acceptable salts thereof.

7. A succinate salt of a compound of formula (I-S)

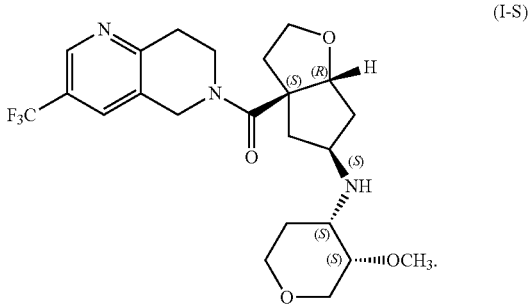

8. A salt as in claim 7, wherein the salt is crystalline.

9. A salt as in claim 7, wherein the salt is a crystalline hydrate; and wherein the hydrate contains about 0.6 moles water per mole of the compound of formula (I-S).

10. A salt as in claim 7, wherein the salt is a crystalline hydrate; and wherein the salt is hygroscopic.

11. A salt as in claim 7, wherein the salt is crystalline and exhibits a peak temperature of melting, as measured by DSC, of about 158° C.

12. A crystalline succinate salt of a compound of formula (I-S)

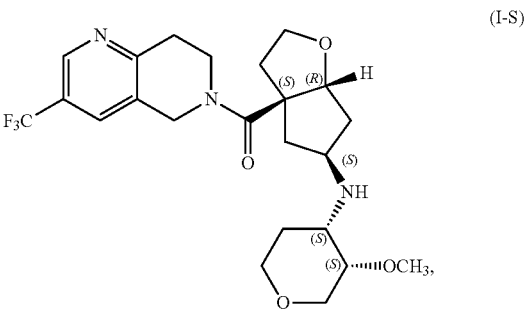

comprising powder X-ray diffraction peaks of 11.27, 13.87, 19.22 and 22.01° 2θ.

13. A pharmaceutical composition, comprising a compound of claim 1 and a pharmaceutically acceptable carrier.

14. A pharmaceutical composition made by mixing a compound of claim 1 and a pharmaceutically acceptable carrier.

15. A process for making a pharmaceutical composition comprising mixing a compound of claim 1 and a pharmaceutically acceptable carrier.

16. A method of treating a disorder selected from the group consisting of: chronic obstructive pulmonary disorder (COPD), ophthalmic disorders, uveitis, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, type-I diabetes, type II diabetes, diabetic complications, diabetic nephropathy, diabetic retinopathy, diabetic retinitis, diabetic microangiopathy, overweight, obesity, obesity-associated insulin resistance, metabolic syndrome, tuberculosis, sarcoidosis, invasive staphyloccocia, inflammation after cataract surgery, allergic rhinitis, allergic conjunctivitis, chronic urticaria, asthma, allergic asthma, periodontal diseases, periodontitis, gingivitis, gum disease, diastolic cardiomyopathies, cardiac infarction, myocarditis, chronic heart failure, angiostenosis, restenosis, reperfusion disorders, aortic abdominal aneurism, glomerulonephritis, solid tumors and cancers, chronic lymphocytic leukemia, chronic myelocytic leukemia, multiple myeloma, malignant myeloma, Hodgkin's disease, carcinomas of the bladder, breast, cervix, colon, lung, prostate, or stomach, and a chronic neuroinflammatory disorder selected from the group consisting of Alzheimer's disease, ischemic stroke, spinal cord injury, nerve crush injury and traumatic brain injury, comprising administering to a subject in need thereof an effective amount of a compound of claim 1.

17. A method of treating a disorder selected from the group consisting of: type I diabetes, type II diabetes, diabetic complications, diabetic nephropathy, diabetic retinopathy, diabetic retinitis, diabetic microangiopathy, obesity, obesity-associated insulin resistance, metabolic syndrome, asthma, and allergic asthma, comprising administering to a subject in need thereof a therapeutically effective amount of a compound of claim 1.

18. A method of treating a disorder selected from the group consisting of type II diabetes, obesity and asthma comprising administering to a subject in need thereof a therapeutically effective amount of a compound of claim 1.

* * * * *